(12) United States Patent
McAllister et al.

(10) Patent No.: US 9,254,272 B2
(45) Date of Patent: Feb. 9, 2016

(54) RESORCINOL DERIVATIVES

(71) Applicant: Sutter West Bay Hospitals, San Francisco, CA (US)

(72) Inventors: Sean D. McAllister, Daly City, CA (US); Pierre-Yves Desprez, Richmond, CA (US); Anuradha Mahadevan, Westford, MA (US)

(73) Assignee: Sutter West Bay Hospitals, San Francisco, CA (US)

( * ) Notice: Subject to any disclaimer, the term of this patent is extended or adjusted under 35 U.S.C. 154(b) by 238 days.

(21) Appl. No.: 13/690,920

(22) Filed: Nov. 30, 2012

(65) Prior Publication Data

US 2013/0209483 A1    Aug. 15, 2013

Related U.S. Application Data

(60) Provisional application No. 61/565,438, filed on Nov. 30, 2011.

(51) Int. Cl.

| | | |
|---|---|---|
| *C07C 39/10* | (2006.01) |
| *A61K 31/085* | (2006.01) |
| *A61K 31/05* | (2006.01) |
| *C07C 43/21* | (2006.01) |
| *C07D 295/096* | (2006.01) |
| *A61K 31/495* | (2006.01) |
| *C07D 295/30* | (2006.01) |
| *C07C 69/017* | (2006.01) |
| *C07C 271/44* | (2006.01) |
| *C07D 213/80* | (2006.01) |
| *C07F 9/09* | (2006.01) |
| *C07C 309/17* | (2006.01) |
| *A61K 31/352* | (2006.01) |
| *A61K 45/06* | (2006.01) |
| *C07F 9/12* | (2006.01) |
| *A61K 31/337* | (2006.01) |
| *A61K 31/4188* | (2006.01) |
| *C07C 69/16* | (2006.01) |
| *C07C 69/40* | (2006.01) |
| *C07C 39/17* | (2006.01) |
| *C07C 39/23* | (2006.01) |
| *C07C 43/23* | (2006.01) |

(52) U.S. Cl.
CPC ............... *A61K 31/05* (2013.01); *A61K 31/085* (2013.01); *A61K 31/337* (2013.01); *A61K 31/352* (2013.01); *A61K 31/4188* (2013.01); *A61K 31/495* (2013.01); *A61K 45/06* (2013.01); *C07C 39/10* (2013.01); *C07C 39/17* (2013.01); *C07C 39/23* (2013.01); *C07C 43/21* (2013.01); *C07C 43/23* (2013.01); *C07C 69/017* (2013.01); *C07C 69/16* (2013.01); *C07C 69/40* (2013.01); *C07C 271/44* (2013.01); *C07C 309/17* (2013.01); *C07D 213/80* (2013.01); *C07D 295/096* (2013.01); *C07D 295/30* (2013.01); *C07F 9/09* (2013.01); *C07F 9/12* (2013.01); *C07C 2101/14* (2013.01); *C07C 2101/16* (2013.01)

(58) Field of Classification Search
None
See application file for complete search history.

(56) References Cited

U.S. PATENT DOCUMENTS

| | | |
|---|---|---|
| 2002/0137064 A1 | 9/2002 | Desprez et al. |
| 2003/0158191 A1 | 8/2003 | Travis |
| 2004/0039048 A1 | 2/2004 | Guzman et al. |
| 2005/0165259 A1 | 7/2005 | Martin et al. |
| 2006/0234273 A1 | 10/2006 | Desprez et al. |
| 2006/0247304 A1 | 11/2006 | Guy et al. |

OTHER PUBLICATIONS

Wiley et al. (Resorcinol Derivatives: A Novel Template for the Development of Cannabinoid CB1/CB2-Selective Agonists, The Journal of Pharmacology and Experimental Therapeutics, vol. 301, No. 2, Jan. 2002, pp. 679-689).*
Guzman, Manuel, "Cannabinoids: Potential Cancer Agents." Nature Reviews Cancer, Oct. 2003, pp. 745-755, vol. 3.
Nickitas-Etienne, Athina, International Preliminary Report on Patentability and Written Opinion, Date of Issuance of Report: Nov. 17, 2009, International Application No. PCT/US08/63837.
Strasser et al., "Comparison of Orally Administered Cannabis Extract and Delta-9-Tetrahydrocannabinol in Treating Patients with Cancer-Related Anorexia-Cachexia Syndrome: A Multicenter, Phase III, Randomized, Double-Blind, Placebo-Controlled Clinical Trial From the Cannabis-In-Cachexia-Study-Group," Journal of Clinical Oncology, vol. 24, No. 21, Jul. 20, 2006, pp. 3394-3400.
Ben-Shabat et al., "New Cannabidiol Derivatives: Synthesis, Binding to Cannabinoid Receptor, and Evaluation of Their Antiinflammatory Activity," J. Med. Chem., 2006, 49, pp. 113-117 (published online Jan. 6, 2006).
Velasco et al., "Hypothesis: cannabinoid therapy for the treatment of gliomas?", Neuropharmacology, 2004, vol. 47, pp. 315-323.
Ligresti et al., "Antitumor Activity of Plant Cannabinoids with Emphasis on the Effect of Cannabidiol on Human Breast Carcinoma," The Journal of Pharmacology and Experimental Therapeutics, 2006, vol. 318, No. 3, pp. 1375-1387.
Kogan et al., "Synthesis and Antitumor Activity of Quinonoid Derivatives of Cannabinoids", J. Med.Chem., 2004, 47, 3800-3806.

* cited by examiner

*Primary Examiner* — Rosalynd Keys
(74) *Attorney, Agent, or Firm* — Joseph R. Baker, Jr.; Gavrilovich, Dodd & Lindsey LLP

(57) ABSTRACT

The disclosure relates to cannabinoid derivative compounds, pharmaceutical compositions made thereof, and methods for treating various diseases and disorders including cancer.

21 Claims, 24 Drawing Sheets

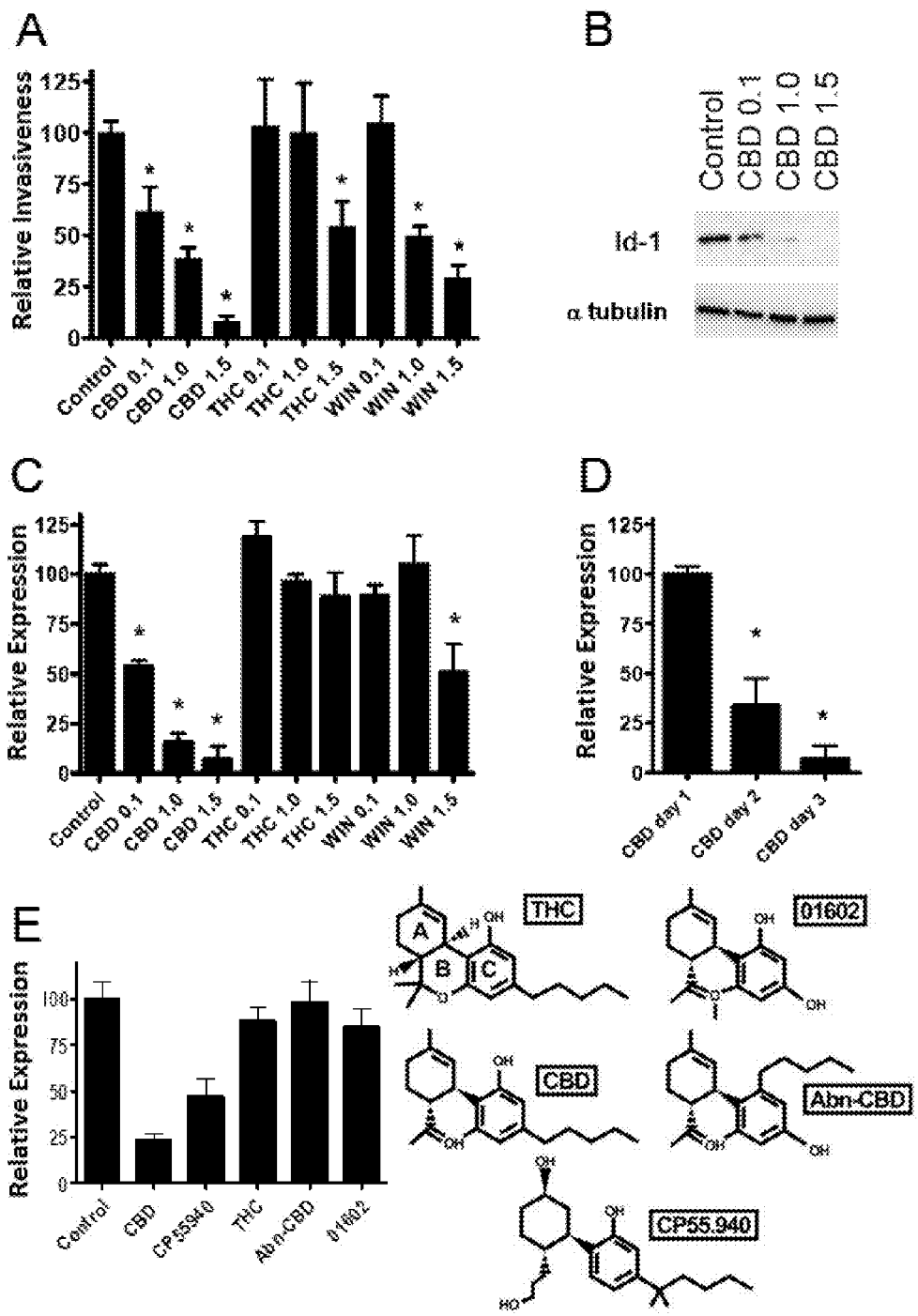
FIGURE 1A-E

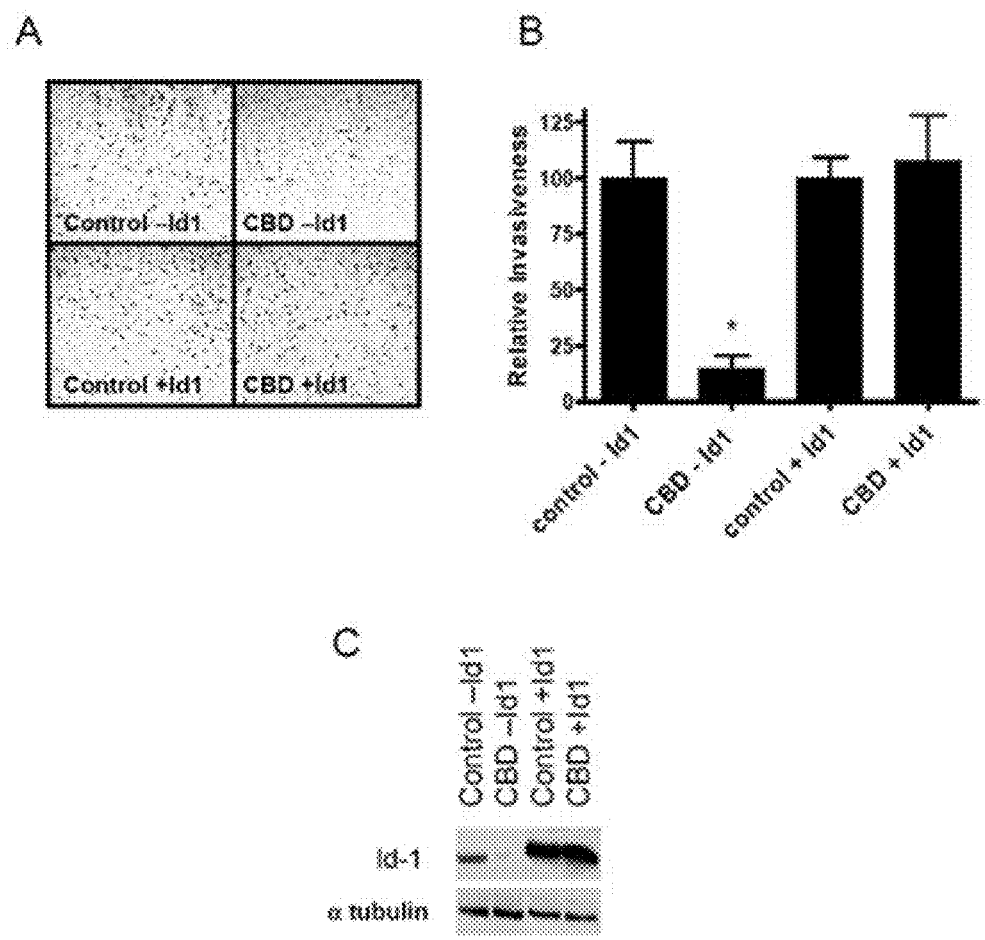
FIGURE 2A-C

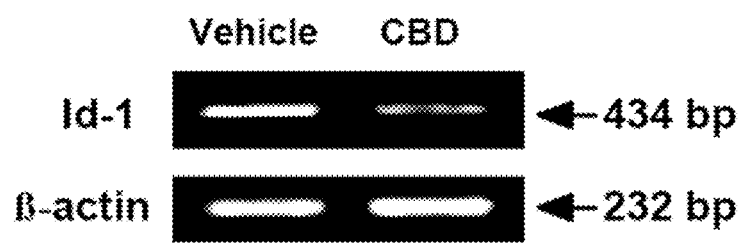
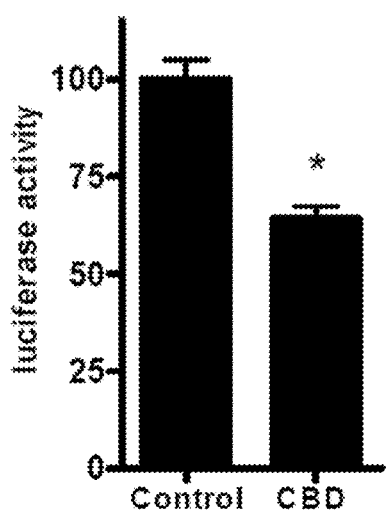
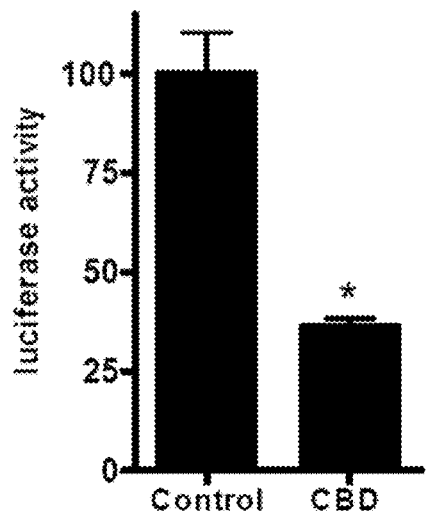
FIGURE 3A-C

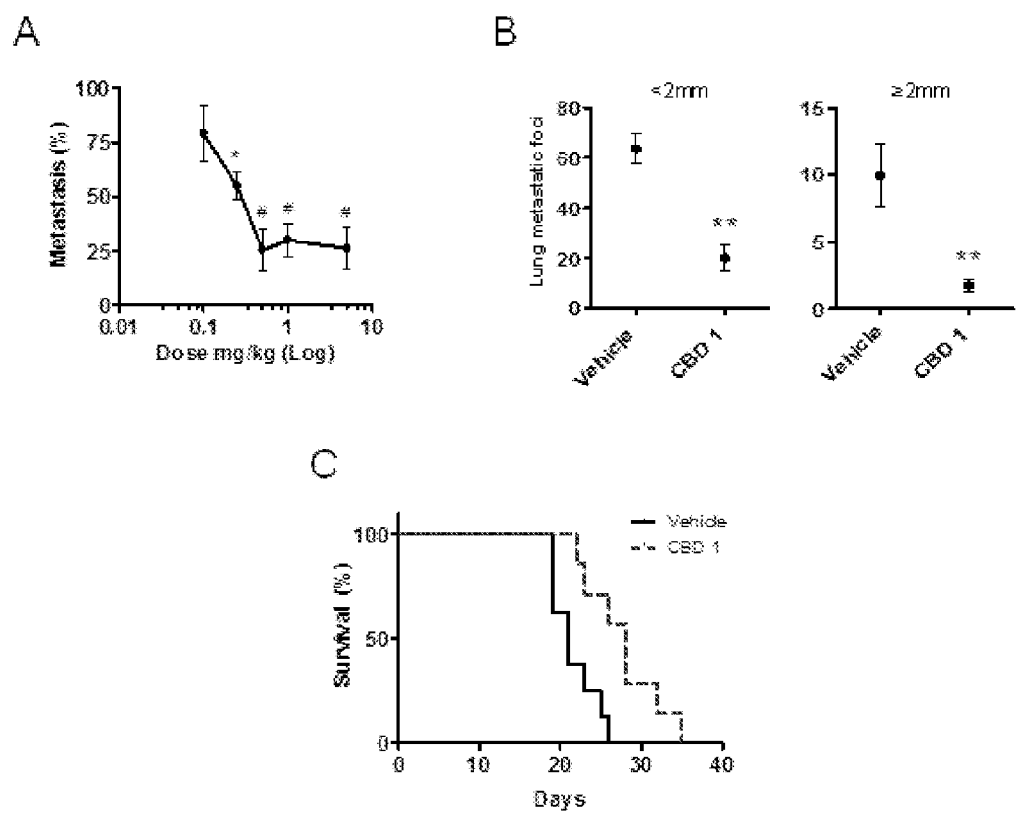
FIGURE 4A-C

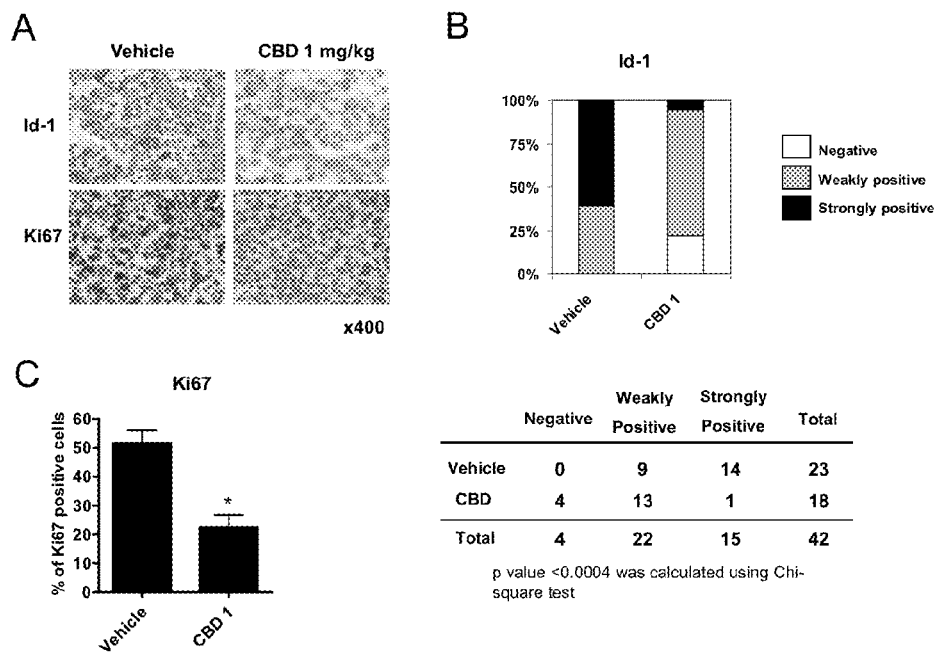
FIGURE 5A-C
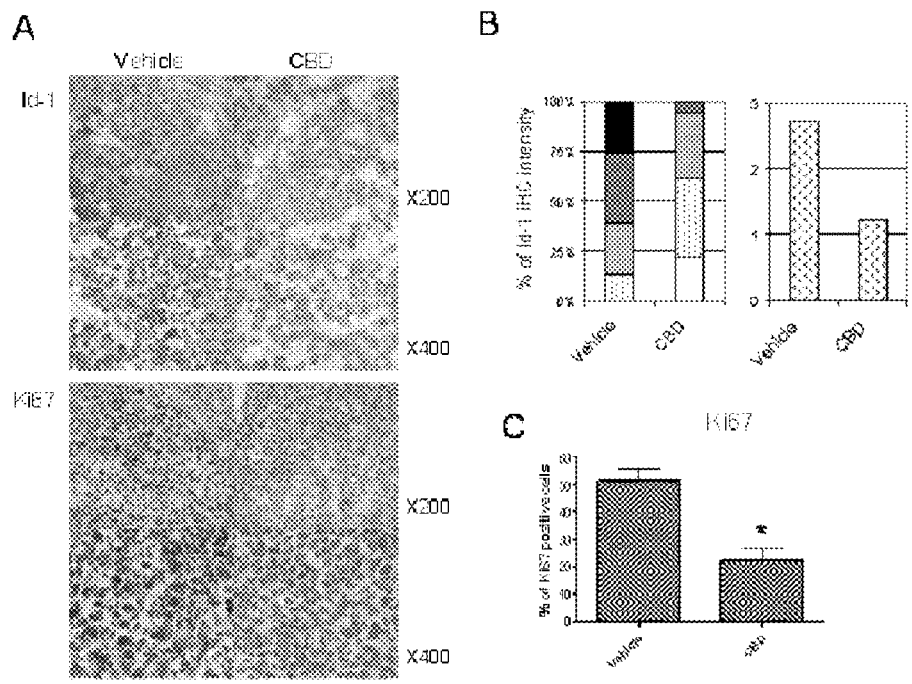
FIGURE 6A-C

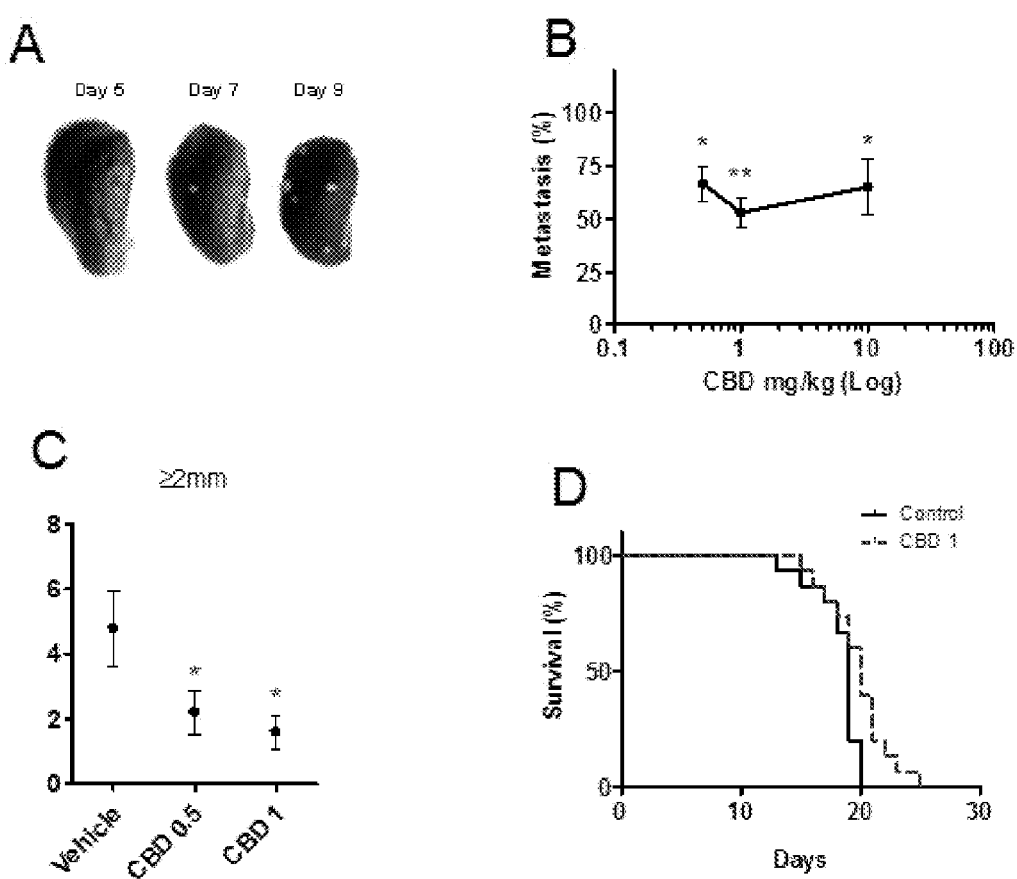
FIGURE 7A-D

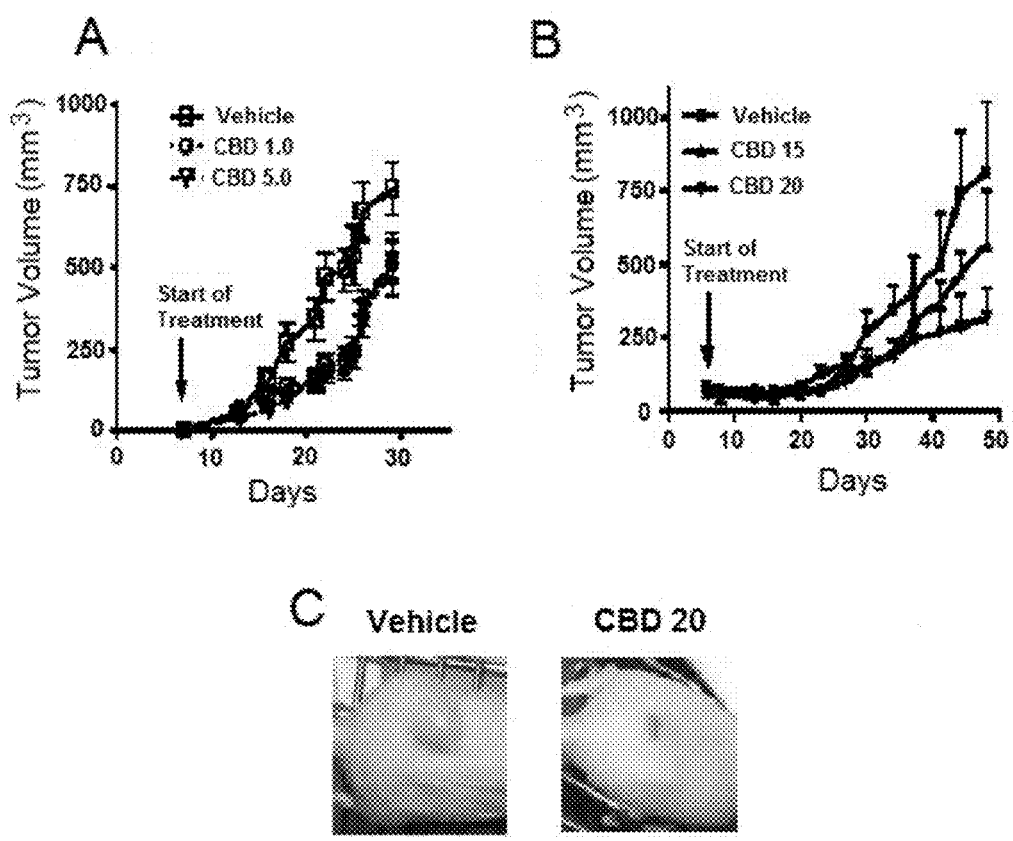
FIGURE 8A-C

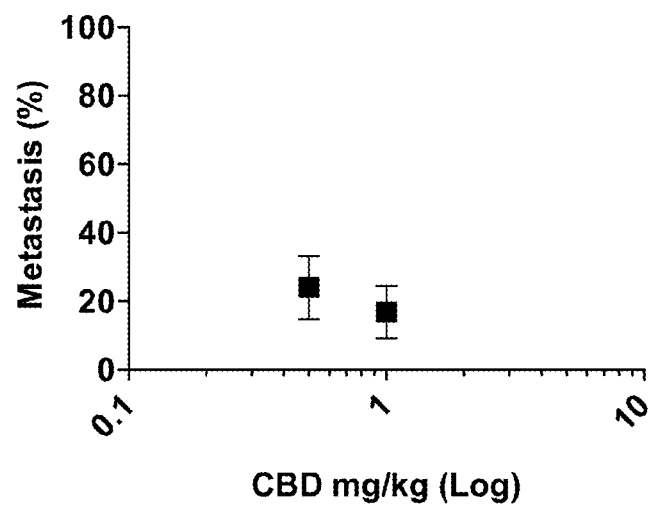
FIGURE 9
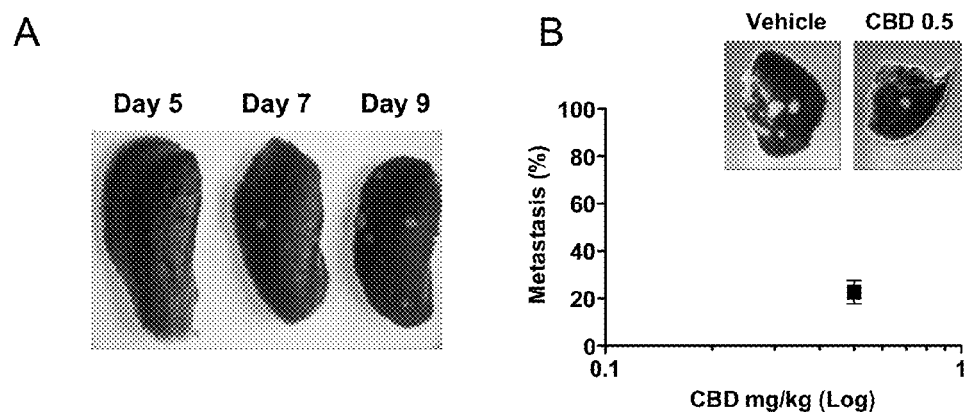
FIGURE 10A-B

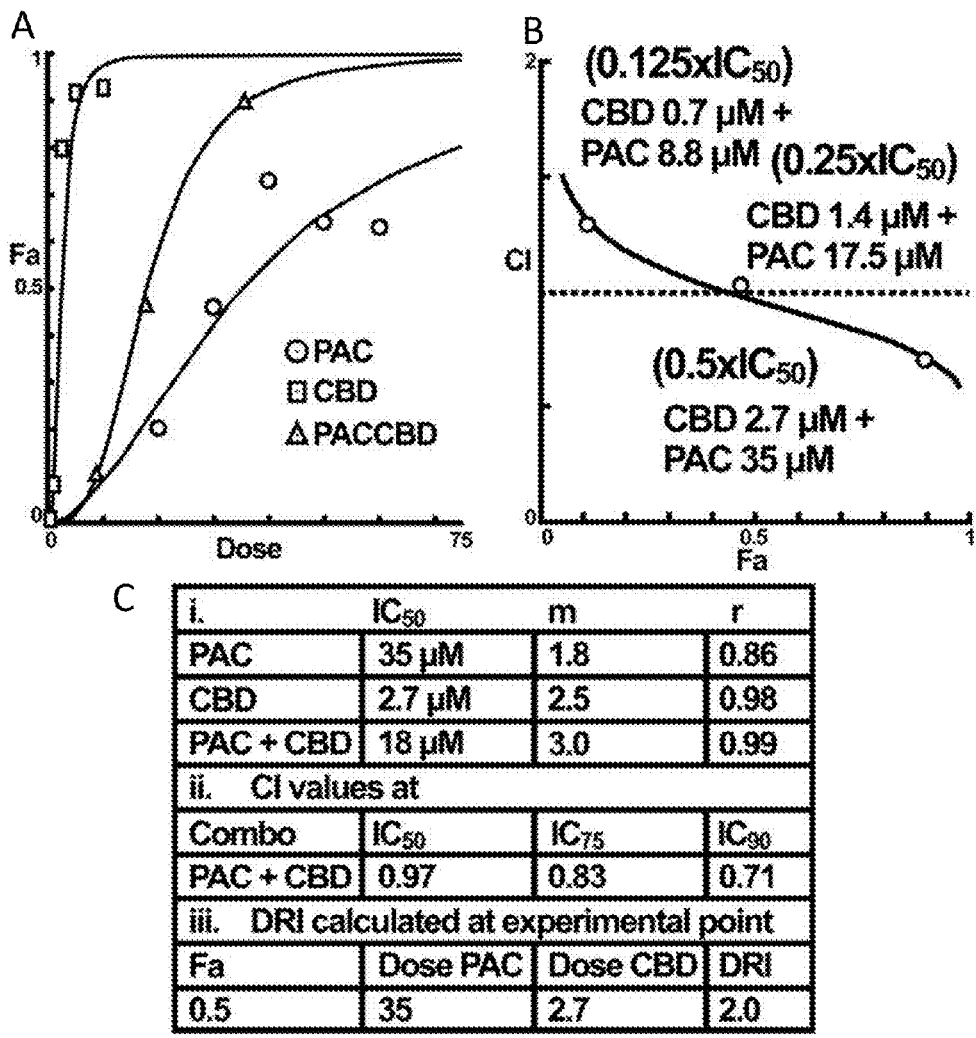
FIGURE 11A-C
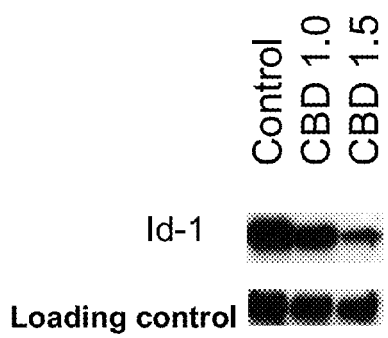
FIGURE 12

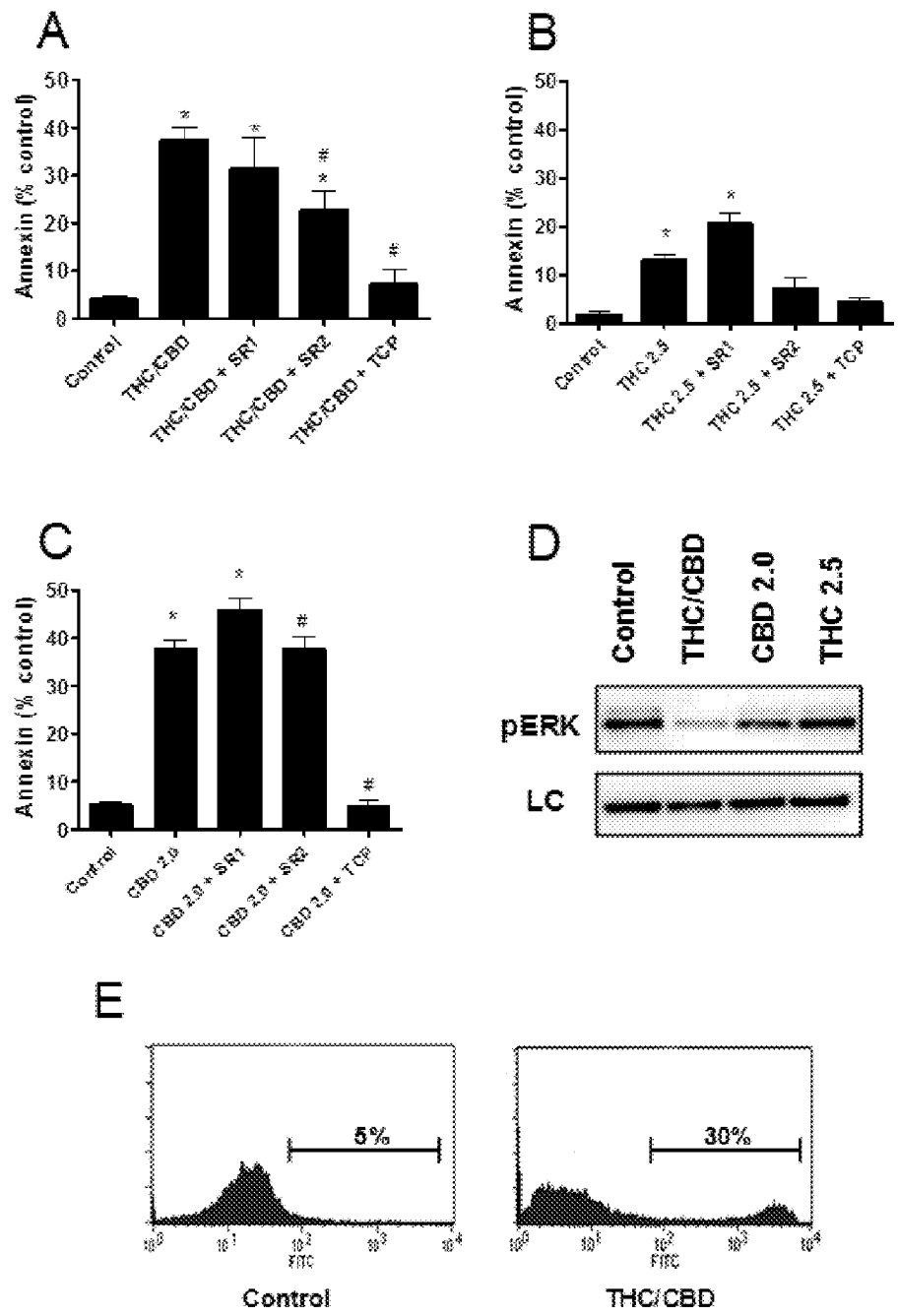
FIGURE 23A-E

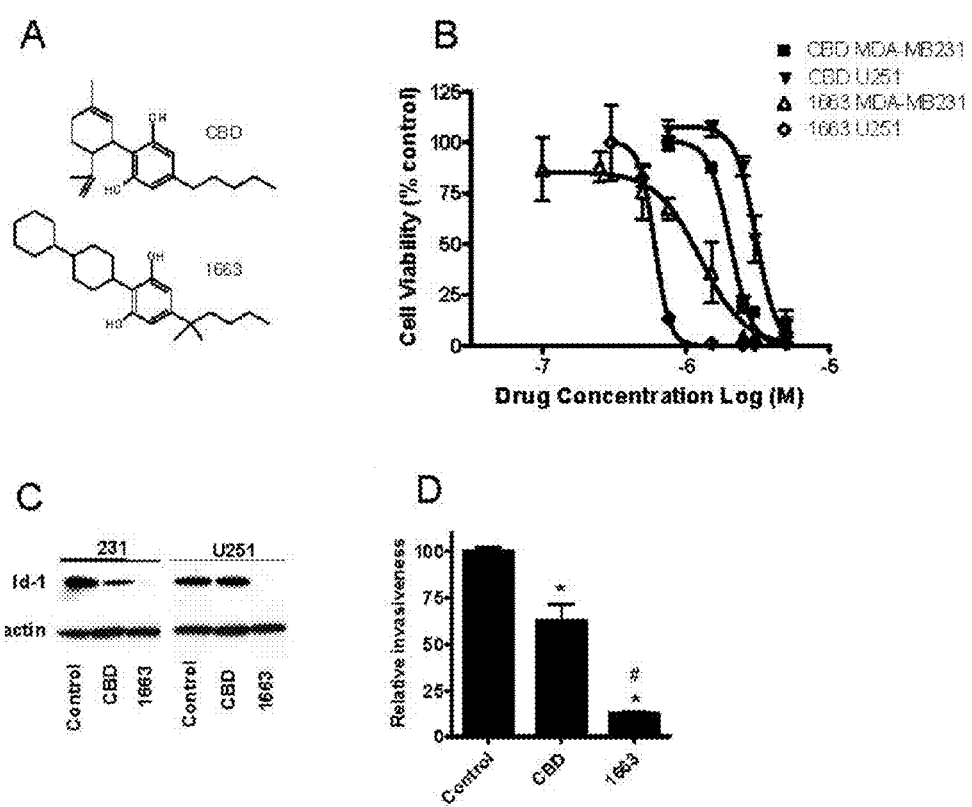
FIGURE 24A-D

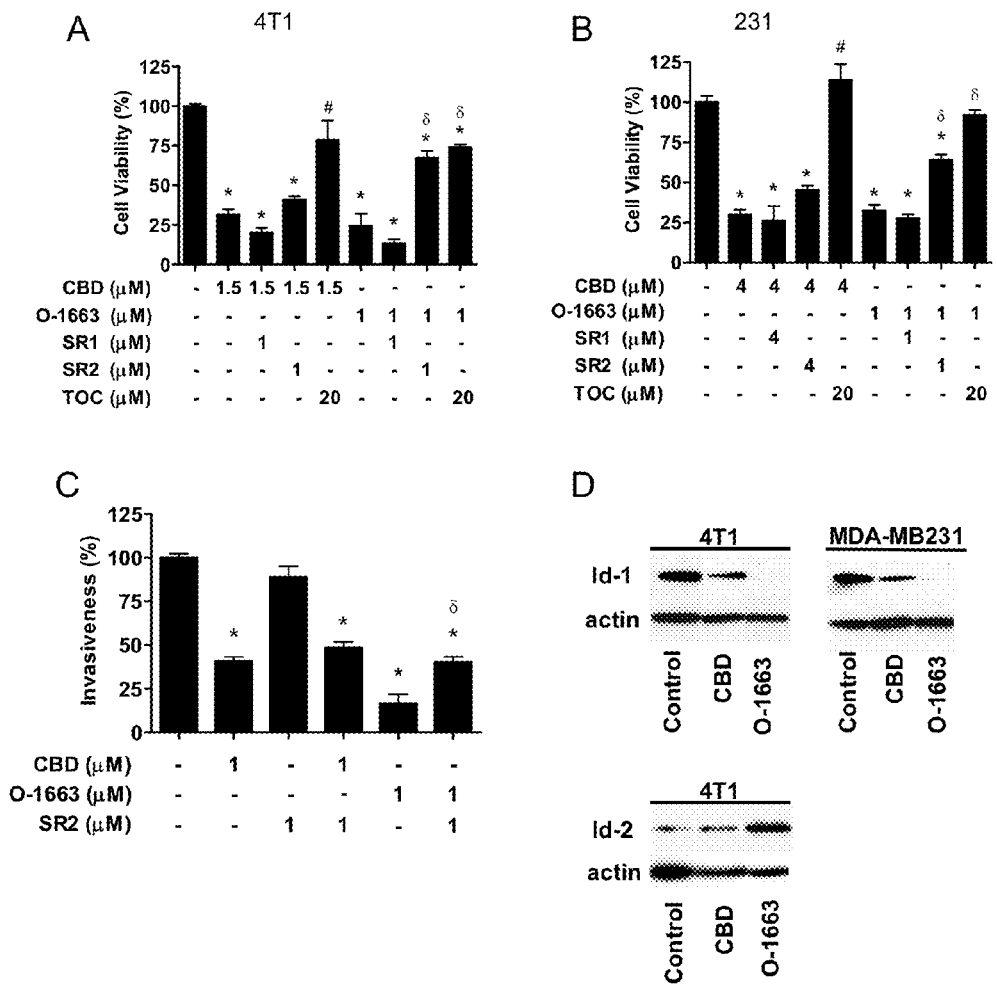
FIGURE 25A-D

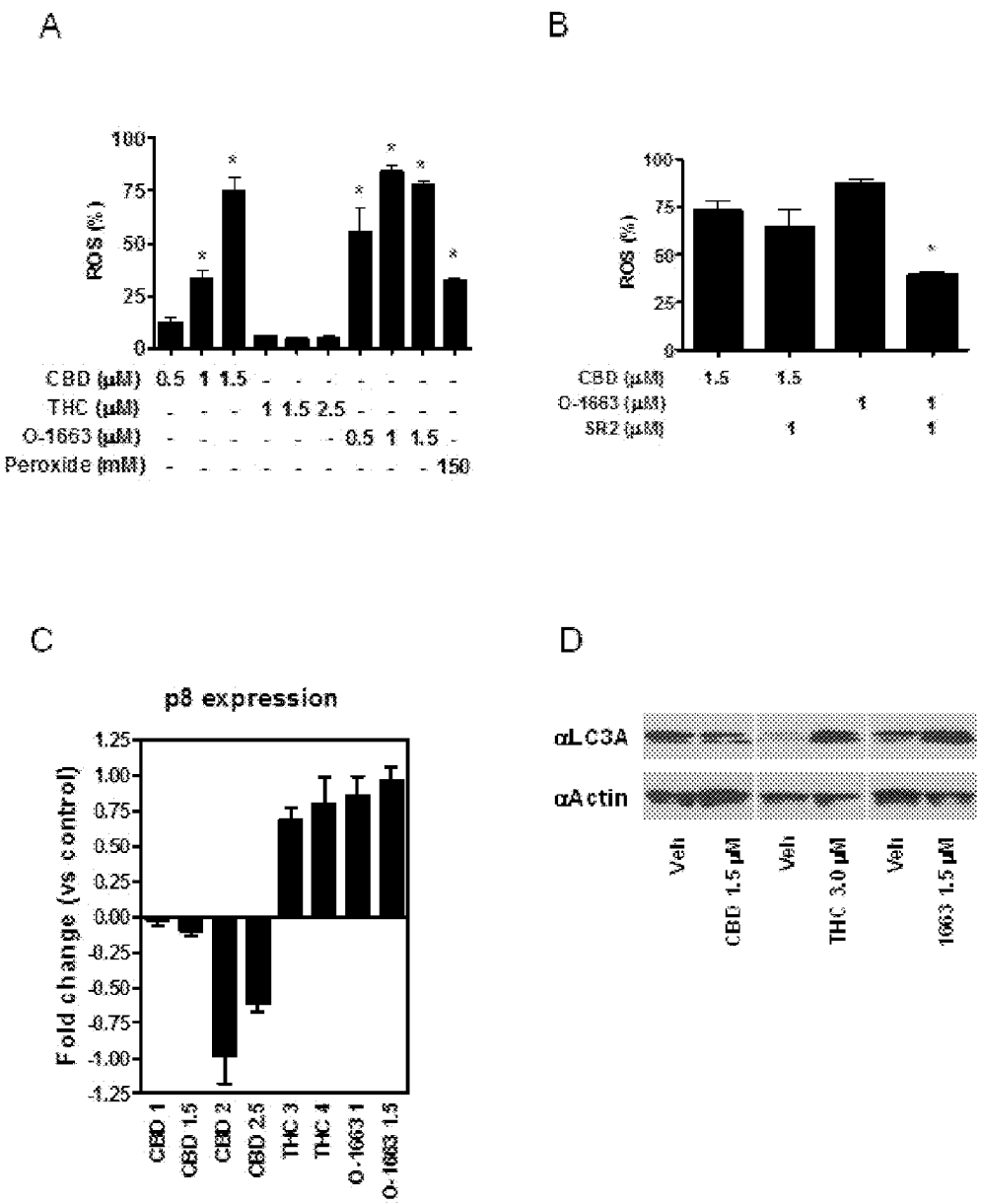
FIGURE 26A-D

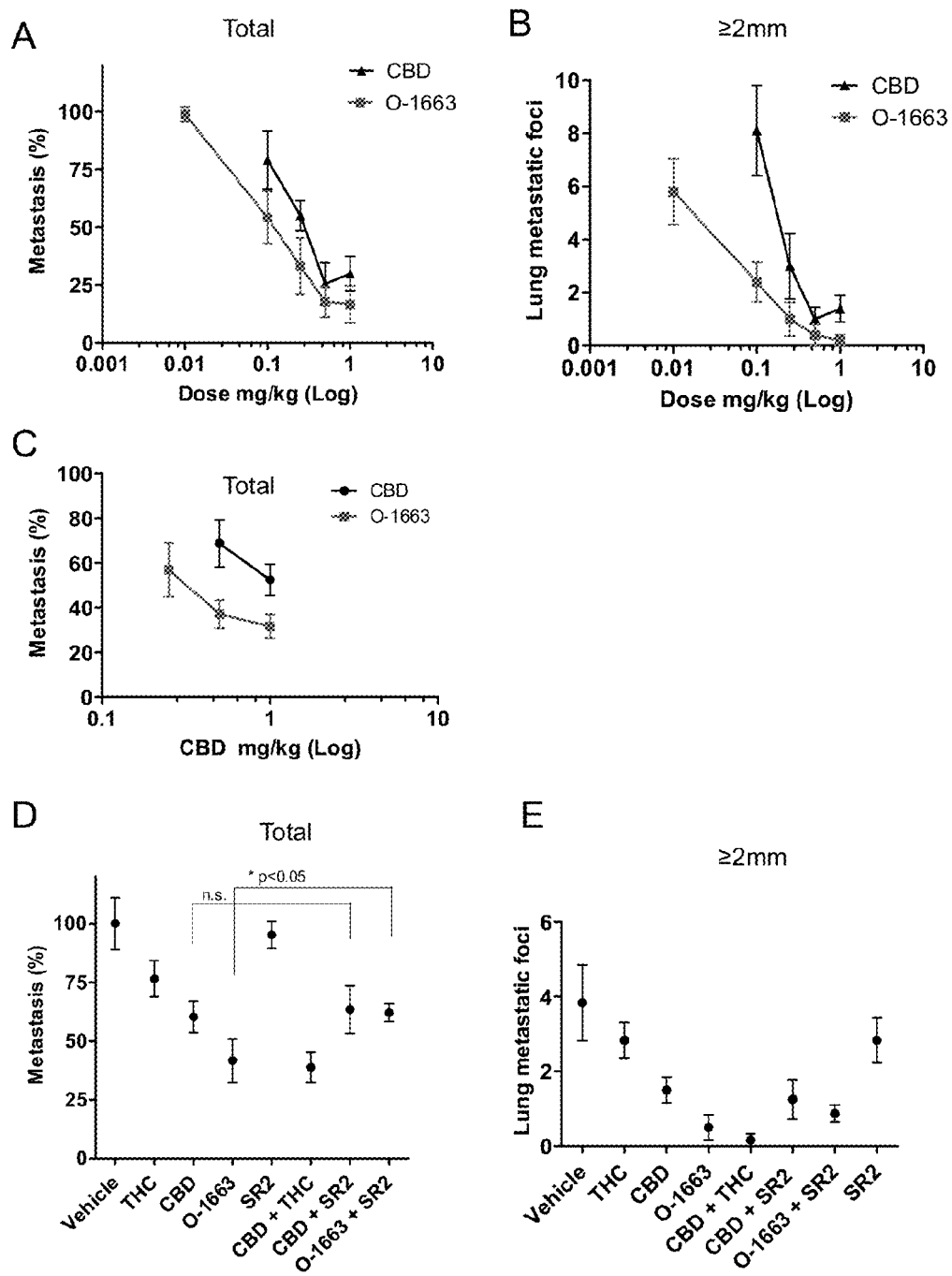
FIGURE 27A-E

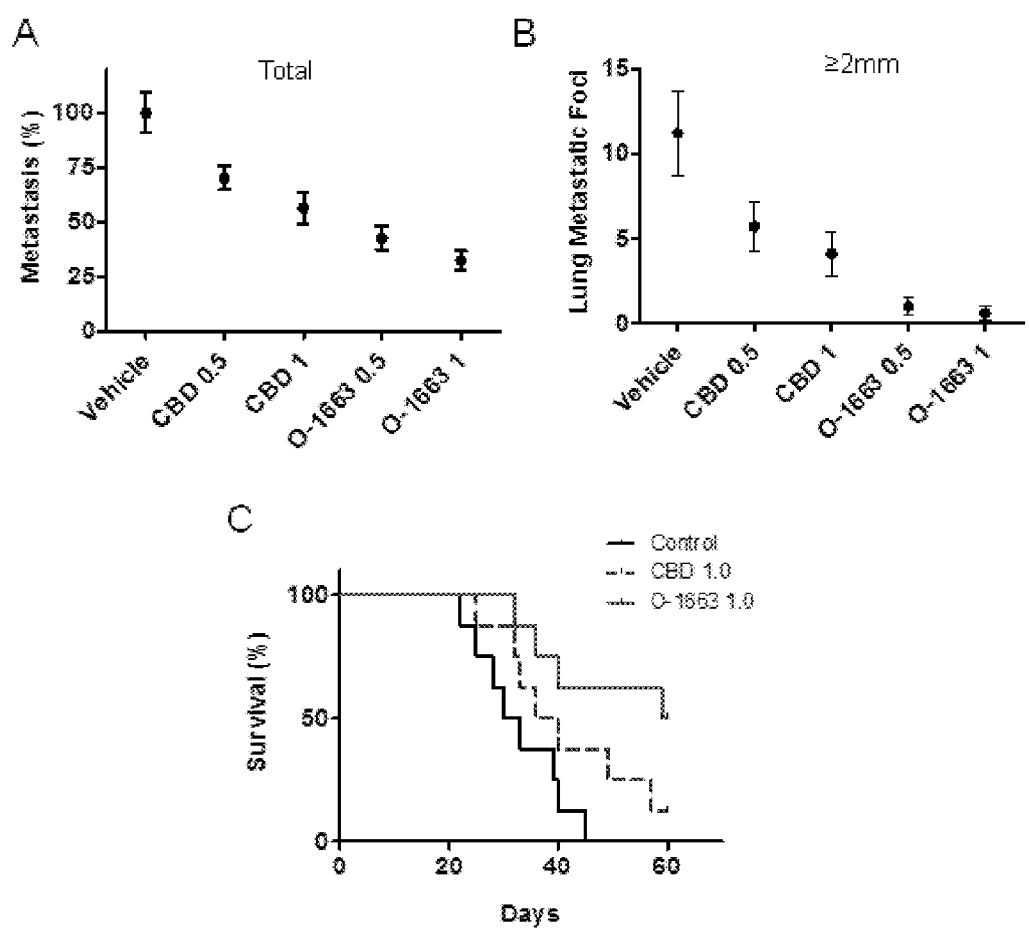
FIGURE 28A-C

RESORCINOL DERIVATIVES

CROSS REFERENCE TO RELATED APPLICATIONS

This application claims priority to U.S. Provisional Application Ser. No. 61/565,438, filed on Nov. 30, 2011, the disclosure of which is incorporated herein by reference.

STATEMENT REGARDING FEDERALLY SPONSORED RESEARCH

This invention was funded by Grant Nos. CA 102412 and CA111723 awarded by the National Institutes of Health. The government has certain rights in the invention.

TECHNICAL FIELD

This invention relates to cannabidiol and derivatives thereof, pharmaceutical compositions made therefrom, and methods of treatment for various disorders, including neoplastic disorders.

BACKGROUND

The hemp plant *Cannabis sativa*, commonly referred to as marijuana, has been used to ameliorate symptoms of diseases and disorders for thousands of years. Currently an oral formulation of $\Delta^9$-tetrahydrocannabinol, the primary active cannabinoid constituent of marijuana, is approved as an antiemetic agent for treating cancer patients undergoing chemotherapy. Additional studies suggest that cannabinoids may increase appetite and alleviate pain in the same patient population.

SUMMARY

In a particular embodiment, the disclosure provides for a compound having the structure of Formula II:

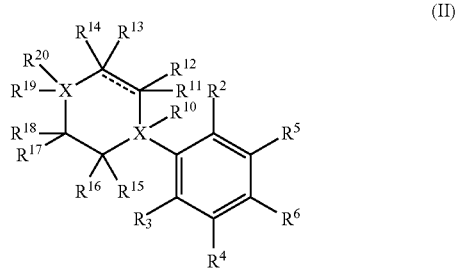

(II)

or a pharmaceutically acceptable salt, or prodrug thereof, wherein:

X is independently a C or N;

$R^2$-$R^3$ are each independently selected from the group consisting of hydroxyl, $(C_1$-$C_2)$alkoxy, carboxylic acid, amine, halo, cyano, and $(C_1$-$C_3)$ ester;

$R^4$-$R^5$ are each independently selected from the group consisting of hydrogen, deuterium, hydroxyl, $(C_1$-$C_2)$alkoxy, carboxylic acid, amine, halo, cyano, and $(C_1$-$C_3)$ester;

$R^6$ is selected from the group consisting of an unsubstituted $(C_1$-$C_{12})$ alkyl, an unsubstituted hetero $(C_1$-$C_{11})$ alkyl, an unsubstituted $(C_1$-$C_{12})$ alkenyl, an unsubstituted hetero $(C_1$-$C_{11})$ alkenyl, an unsubstituted $(C_1$-$C_{12})$alkynyl, and an unsubstituted hetero$(C_1$-$C_{11})$alkynyl;

$R^{10}$-$R^{19}$ are each independently selected from the group consisting of hydrogen, deuterium, functional group ("FG"), optionally substituted $(C_1$-$C_8)$alkyl, optionally substituted hetero$(C_1$-$C_8)$alkyl, optionally substituted $(C_1$-$C_8)$alkenyl, optionally substituted hetero$(C_1$-$C_8)$alkenyl, optionally substituted $(C_1$-$C_8)$alkynyl, optionally substituted hetero$(C_1$-$C_8)$ alkynyl, optionally substituted $(C_5$-$C_{12})$cycloalkyl, optionally substituted $(C_5$-$C_{12})$cycloalkenyl, optionally substituted $(C_5$-$C_{12})$cycloalkynyl, optionally substituted $(C_4$-$C_{11})$heterocycle, optionally substituted aryl, and optionally substituted extended mixed ring system; and $R^{20}$ is selected from the group consisting of optionally substituted $(C_5$-$C_{12})$cycloalkyl, optionally substituted $(C_5$-$C_{12})$cycloalkenyl, optionally substituted $(C_5$-$C_{12})$cycloalkynyl, optionally substituted $(C_4$-$C_{11})$heterocycle, substituted aryl, optionally substituted aryl having two or more rings, and optionally substituted extended mixed ring system.

In a further embodiment, $R^6$ is selected from the group consisting of methyl, ethyl, n-propyl, n-butyl, n-pentyl, n-hexyl, n-heptyl, isopropyl, sec-butyl, (1-methyl)butyl, (1-methyl)pentyl, (1-methyl)hexyl, (1-methyl)heptyl, (1,1-dimethyl)propyl, (1,1-dimethyl)butyl, (1,1-dimethyl)pentyl, (1,1-dimethyl)hexyl, (1,1-dimethyl)heptyl, (1,2-dimethyl)propyl, (1,2-dimethyl)butyl, (1,2-dimethyl)pentyl, (1,2-dimethyl)hexyl, (1,2-dimethyl)heptyl, (1,3-dimethyl)butyl, (1,3-dimethyl)pentyl, (1,3-dimethyl)hexyl, (1,3-dimethyl)heptyl, (1,4-dimethyl)pentyl, (1,4-dimethyl)hexyl, (1,4-dimethyl)heptyl, (1,5-dimethyl)hexyl, (1,5-dimethyl)heptyl, (1,6-dimethyl)heptyl, (1,2-diethyl)butyl, (1,2-diethyl)pentyl, (1,2-diethyl)hexyl, (1,2-diethyl)heptyl, (1,2-diethyl)pentyl, (1,3-diethyl)pentyl, (1,3-diethyl)hexyl, (1,3-diethyl)heptyl, (1,4-diethyl)pentyl, (1,4-diethyl)hexyl, (1,4-diethyl)heptyl, (1,5-diethyl)hexyl, (1,5-diethyl)heptyl, (1,6-diethyl)heptyl, (1,2,3-trimethyl)butyl, (1,1,2-trimethyl)butyl, (1,1,3-trimethyl)butyl, (1,2,3-trimethyl)pentyl, (1,1,2-trimethyl)pentyl, (1,1,3-trimethyl)pentyl, (1,2,4-trimethyl)pentyl, (1,3,4-trimethyl)pentyl, (1,1,4-trimethyl)pentyl, (1,2,3-trimethyl)hexyl, (1,1,2-trimethyl)hexyl, (1,1,3-trimethyl)hexyl, (1,2,4-trimethyl)hexyl, (1,2,5-trimethyl)hexyl, (1,1,4-trimethyl)hexyl, (2,3,4-trimethyl)hexyl, (2,3,5-trimethyl)hexyl, (1,1,5-trimethyl)hexyl, (1,2,3-trimethyl)heptyl, (1,1,2-trimethyl)heptyl, (1,1,3-trimethyl)heptyl, (1,2,4-trimethyl)heptyl, (1,1,5-trimethyl)heptyl, (1,1,6-trimethyl)heptyl, (1,2,5-trimethyl)heptyl, (1,2,6-trimethyl)heptyl, (2,3,4-trimethyl)heptyl, (2,3,5-trimethyl)heptyl, (2,3,6-trimethyl)heptyl, (2,4,5-trimethyl)heptyl, (2,4,6-trimethyl)heptyl, (3,4,5-trimethyl)heptyl, (3,4,6-trimethyl)heptyl, and (4,5,6-trimethyl)heptyl.

In yet a further embodiment, $R^{20}$ is selected from the group consisting of an optionally substituted $(C_5$-$C_7)$cycloalkyl, an optionally substituted $(C_5$-$C_7)$cycloalkenyl, a substituted aryl, an optionally substituted aryl having two or more rings, and an optionally substituted heterocycle containing 4, 5, or 6 ring atoms.

Examples of optionally substituted heterocycles containing 4, 5, or 6 ring atoms include:

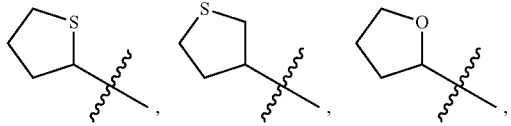

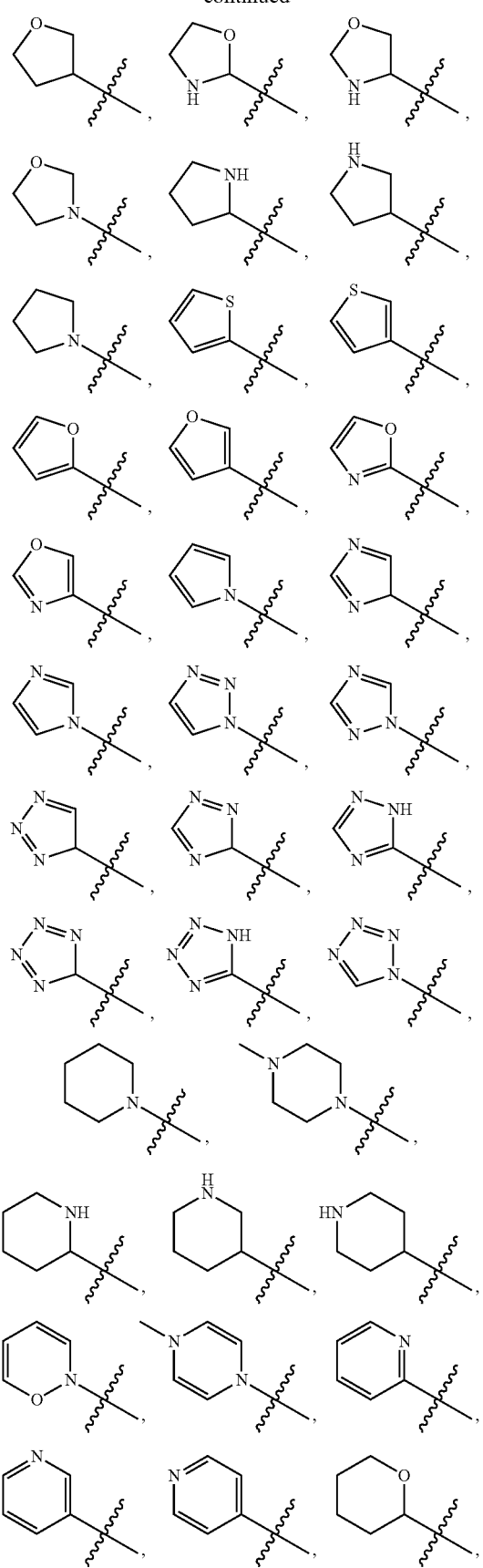
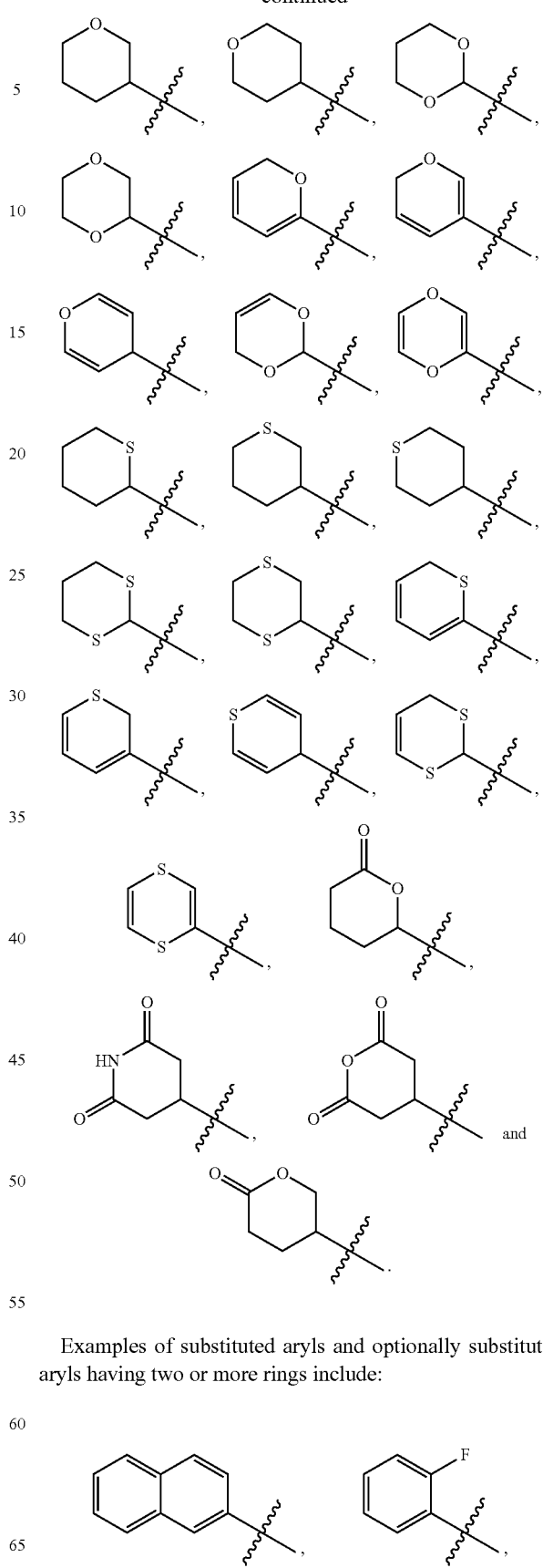
Examples of substituted aryls and optionally substituted aryls having two or more rings include:
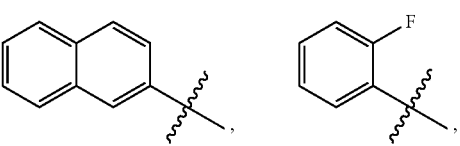

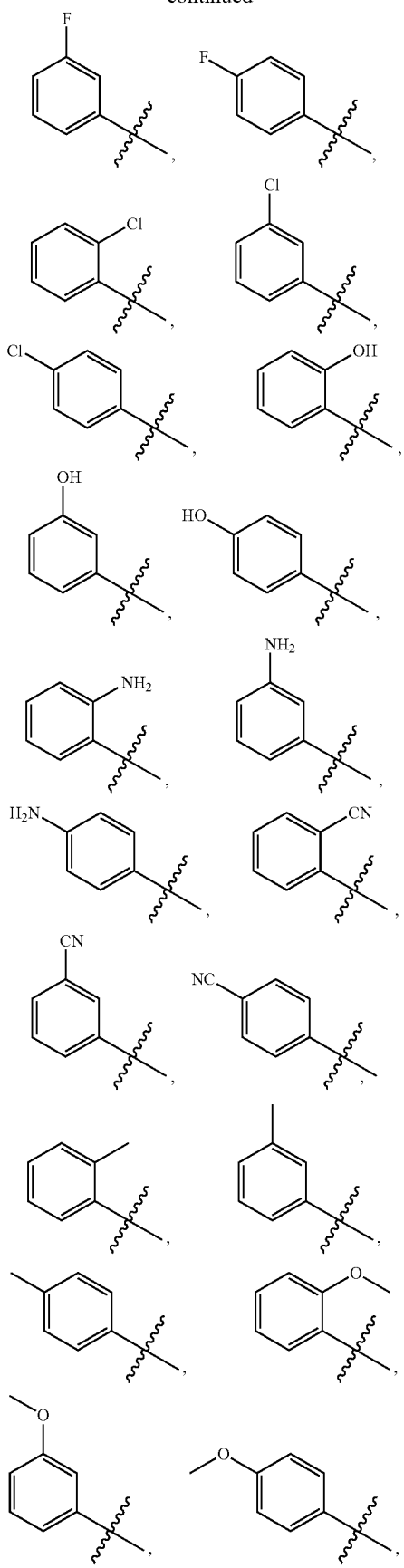
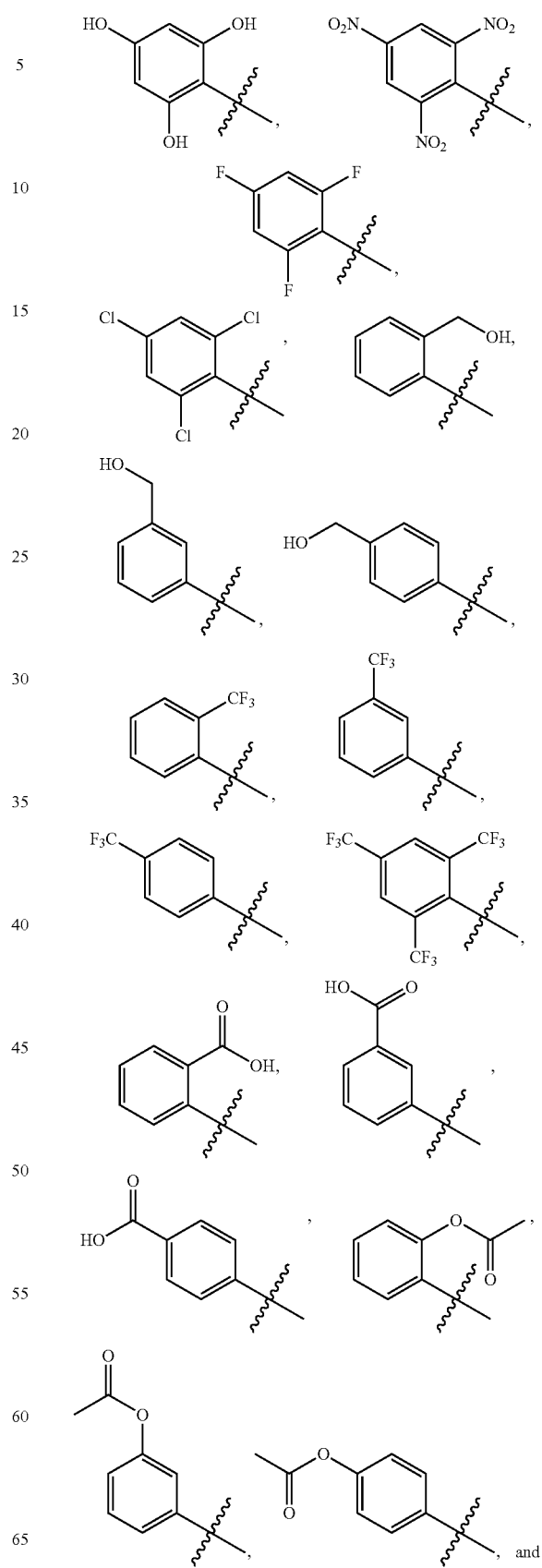

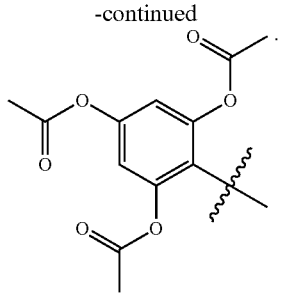
Examples of optionally substituted (C$_5$-C$_7$)cycloalkyls include:
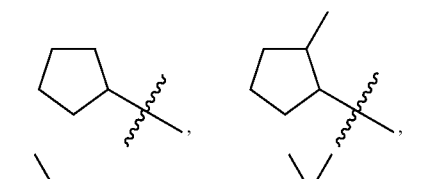
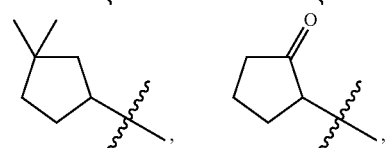
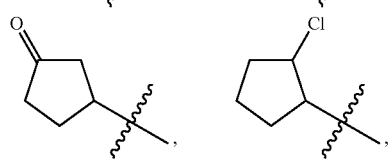
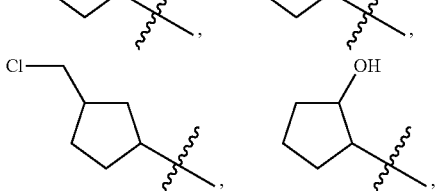
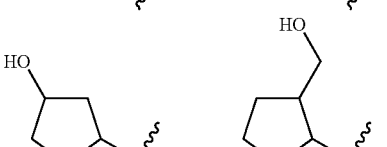
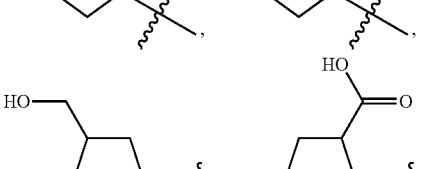
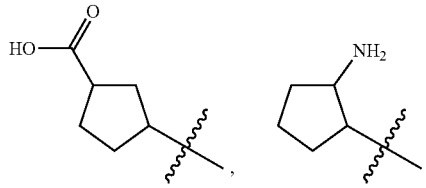
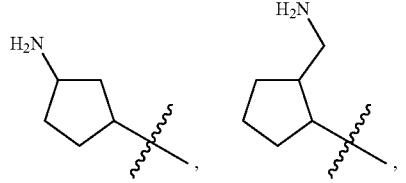
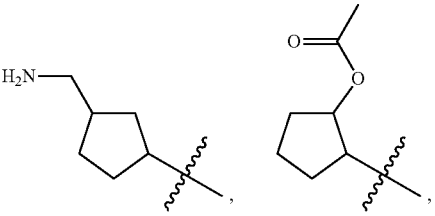
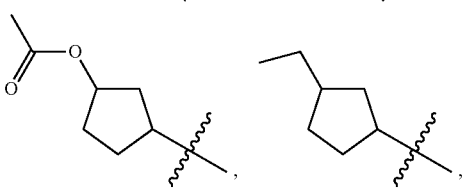
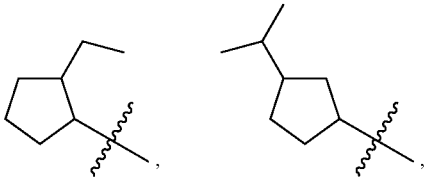
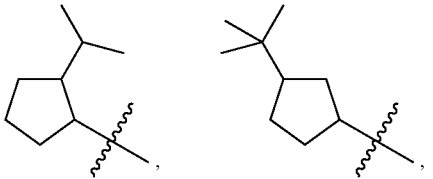
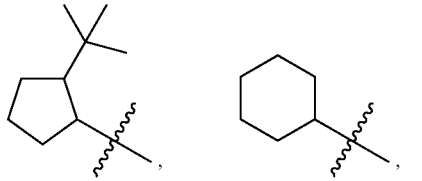
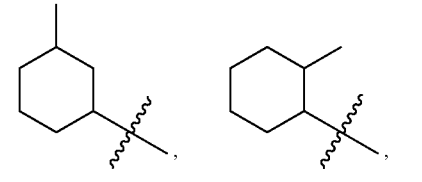
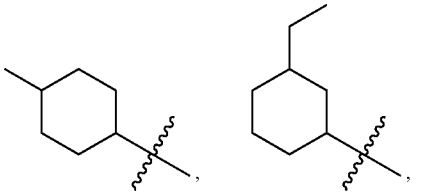

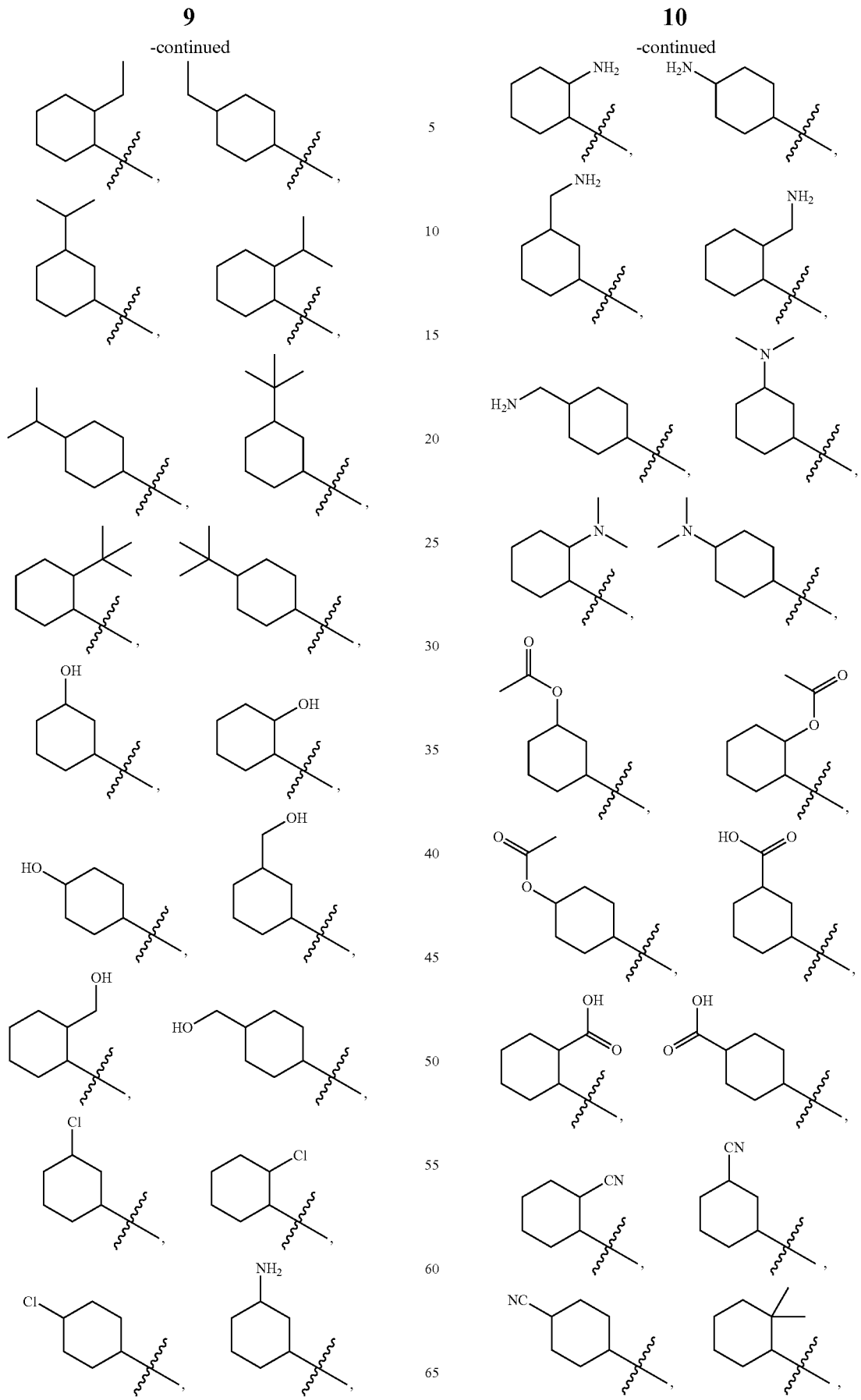

-continued

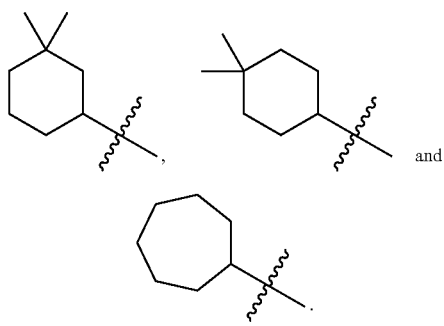

and

In a certain embodiment, a compound of Formula II, may further have a structure of Formula III:

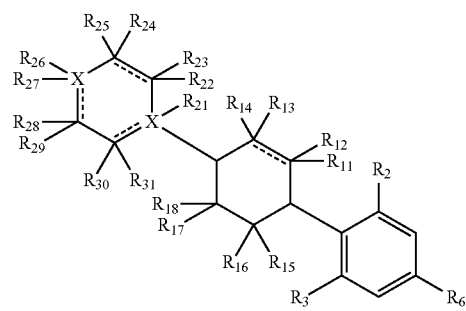

(III)

or a pharmaceutically acceptable salt, or prodrug thereof, wherein:

X is independently either a C or N;

$R^2$-$R^3$ are each independently a hydroxyl or ($C_1$-$C_2$) alkoxy;

$R^6$ is selected from the group consisting of an unsubstituted ($C_1$-$C_{12}$) alkyl, an unsubstituted hetero ($C_1$-$C_{11}$) alkyl, an unsubstituted ($C_1$-$C_{12}$) alkenyl, an unsubstituted hetero ($C_1$-$C_{11}$) alkenyl, an unsubstituted ($C_1$-$C_{12}$)alkynyl, and an unsubstituted hetero($C_1$-$C_{11}$)alkynyl;

$R^{11}$-$R^{18}$ are each independently selected from the group consisting of hydrogen, deuterium, FG, optionally substituted ($C_1$-$C_8$)alkyl, optionally substituted hetero($C_1$-$C_8$) alkyl, optionally substituted ($C_1$-$C_8$)alkenyl, optionally substituted hetero($C_1$-$C_8$)alkenyl, optionally substituted ($C_1$-$C_8$) alkynyl, optionally substituted hetero ($C_1$-$C_8$) alkynyl; and $R^{21}$-$R^{31}$ are each independently selected from the group consisting of hydrogen, deuterium, FG, optionally substituted ($C_1$-$C_8$)alkyl, hetero ($C_1$-$C_8$) alkyl, optionally substituted ($C_1$-$C_8$)alkenyl, optionally substituted hetero($C_1$-$C_8$) alkenyl, optionally substituted ($C_1$-$C_8$) alkynyl, optionally substituted hetero ($C_1$-$C_8$) alkynyl, optionally substituted ($C_5$-$C_8$)cycloalkyl, optionally substituted ($C_5$-$C_8$)cycloalkenyl, optionally substituted ($C_5$-$C_8$)cycloalkynyl, optionally substituted ($C_4$-$C_8$)heterocycle, optionally substituted aryl, and optionally substituted extended mixed ring system.

In a further embodiment, a compound of Formula II or of Formula III has the structure of:

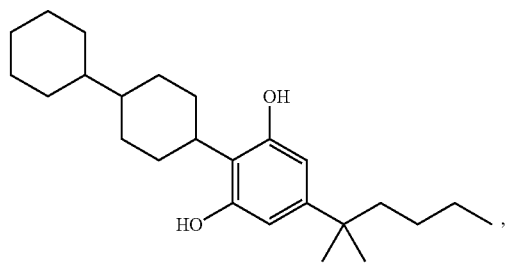 [SMILES: CCCCC(C)(C)c1cc(O)c(C2CCC(C3CCCCC3)CC2)c(O)c1]

or a pharmaceutically acceptable salt, or prodrug thereof. Examples of prodrugs for a compound of:

include:

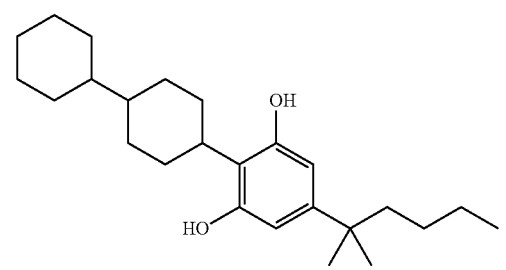

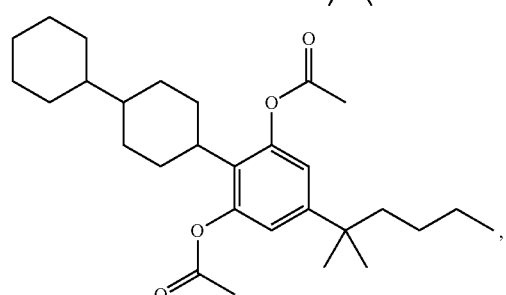

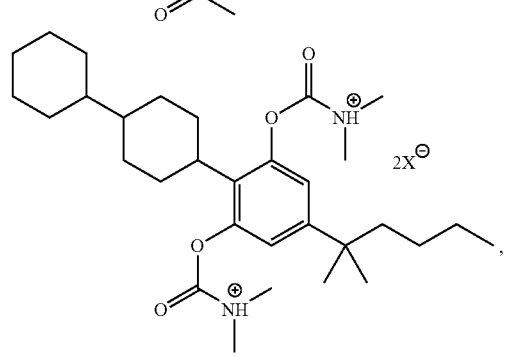

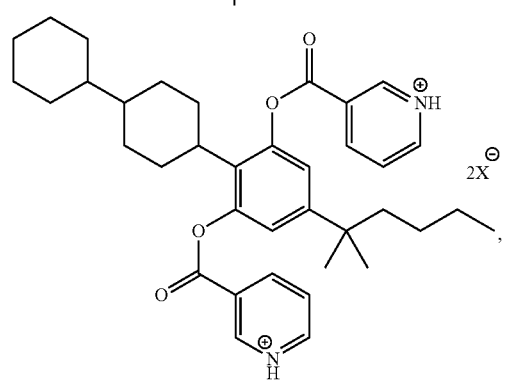

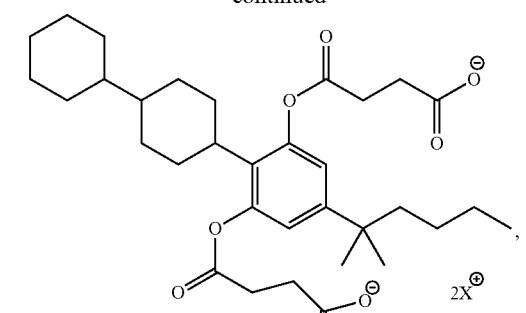
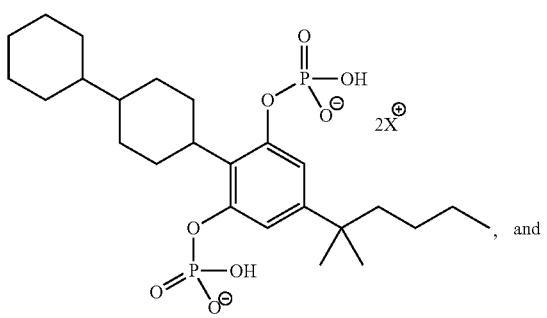
, and
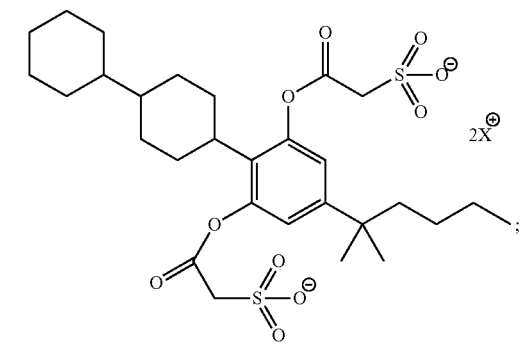
;
wherein, X is a pharmaceutically acceptable counter ion.
In another embodiment, a compound of Formula II or of Formula III has the structure selected from the group of:
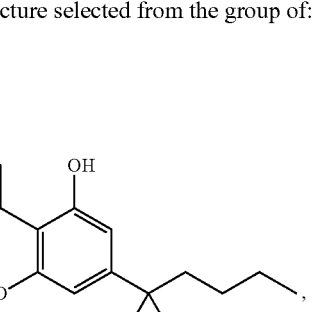
,
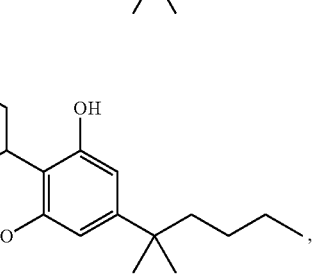
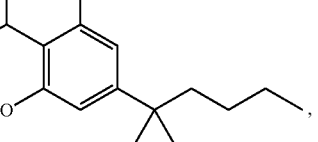
,
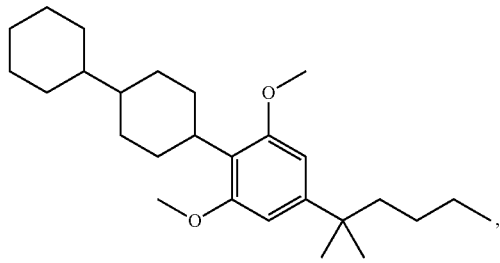
,
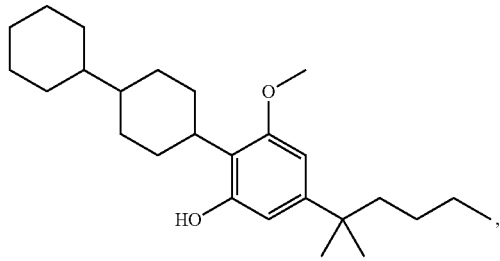
,
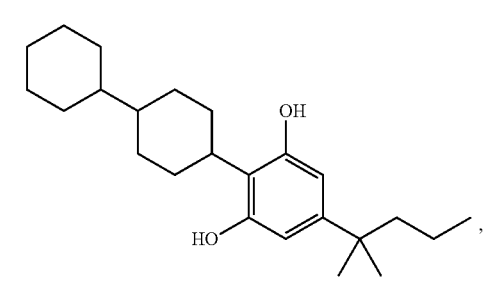
,
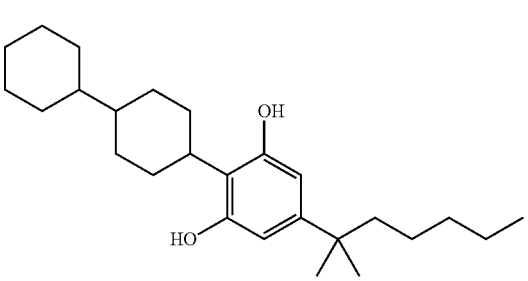
,
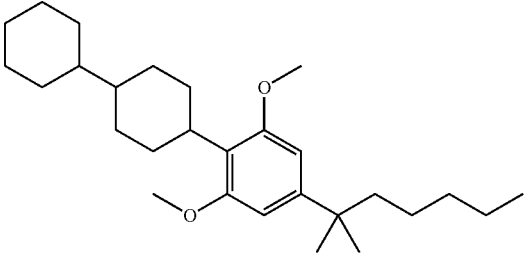
,
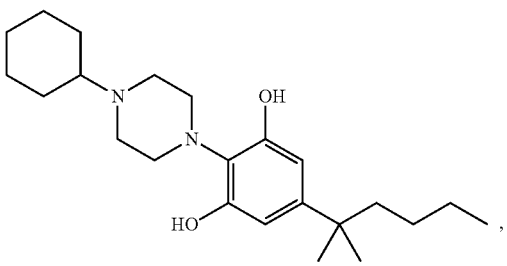
, -continued

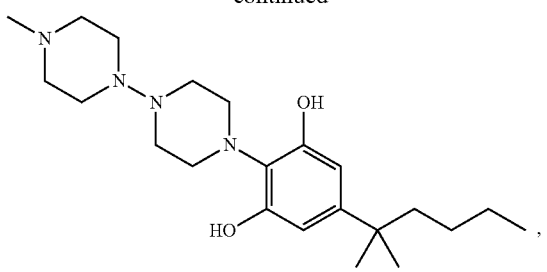

,

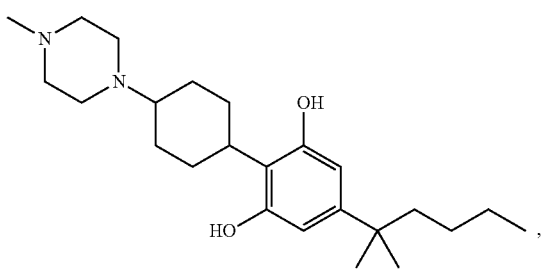

,

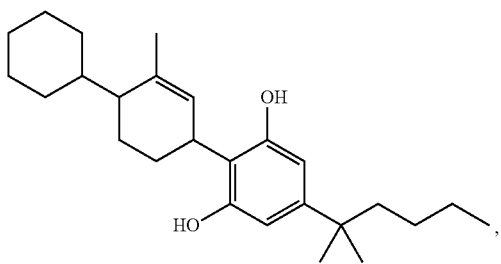

,

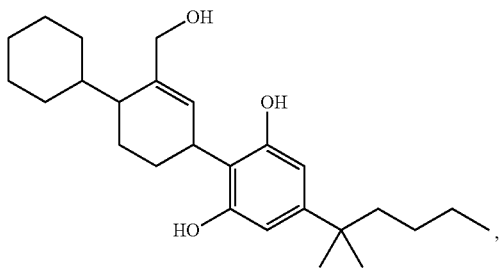

,

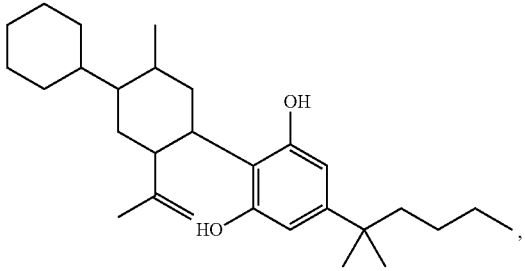

,

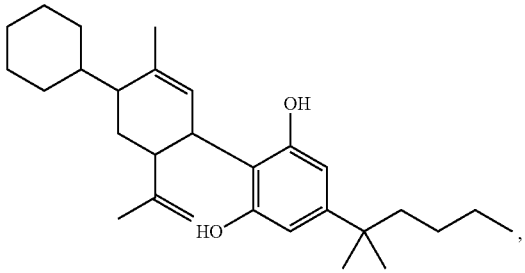

,

-continued

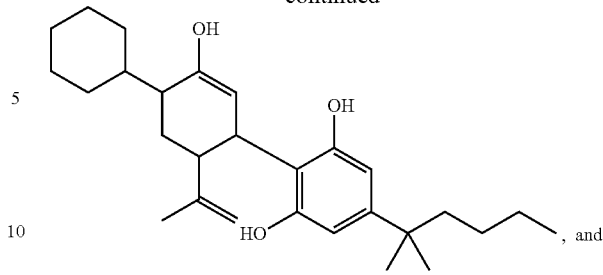

, and

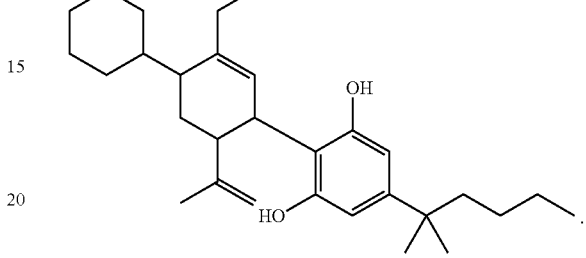

.

In a particular embodiment, the disclosure provides for pharmaceutical compositions comprising a pharmaceutically acceptable carrier together with a compound of the disclosure. In a further embodiment, the pharmaceutical composition may further comprise an additional therapeutic agent, such as $\Delta^9$-tetrahydrocannabinol ("THC") or a THC derivative. Examples of derivatives of THC include $\Delta^9$-tetrahydrocannabinol-$C_4$, $\Delta^9$-tetrahydrocannabivarin, tetrahydrocannabiorcol, $\Delta^9$-tetrahydro-cannabinolic acid A, $\Delta^9$-tetrahydro-cannabinolic acid B, $\Delta^9$-tetrahydro-cannabinolic acid-$C_4$ A, $\Delta^9$-tetrahydro-cannabinolic acid-$C_4$, $\Delta^9$-tetrahydro-cannabivarinic acid A, $\Delta^9$-tetrahydro-cannabiorcolic acid A, $\Delta^9$-tetrahydro-cannabiorcolic acid B, (−)-$\Delta^8$-trans-(6aR,10aR)-$\Delta^8$-tetrahydrocannabinol, (−)-$\Delta^8$-trans-(6aR,10aR)-tetrahydrocannabinolic acid A, and (−)-(6aS,10aR)-$\Delta^9$-tetrahydrocannabinol. In yet a further embodiment, an additional therapeutic agent is selected from alkylating agents, cancer immunotherapy monoclonal antibodies, anti-metabolites, mitotic inhibitors, anti-tumor antibiotics, topisomerase inhibitors, photosensitizers, tyrosine kinase inhibitors, anti-cancer agents, chemotherapeutic agents, anti-migraine treatments, anti-tussives, mucolytics, decongestants, anti-allergic non-steroidals, expectorants, anti-histamine treatments, anti-retroviral agents, CYP3A inhibitors, CYP3A inducers, protease inhibitors, adrenergic agonists, anti-cholinergics, mast cell stabilizers, xanthines, leukotriene antagonists, glucocorticoid treatments, antibacterial agents, antifungal agents, sepsis treatments, steroidals, local or general anesthetics, NSAIDS, NRIs, DARIs, SNRIs, sedatives, NDRIs, SNDRIs, monoamine oxidase inhibitors, hypothalamic phoshpholipids, anti-emetics, ECE inhibitors, opioids, thromboxane receptor antagonists, potassium channel openers, thrombin inhibitors, growth factor inhibitors, anti-platelet agents, P2Y(AC) antagonists, anti-coagulants, low molecular weight heparins, Factor VIa inhibitors, Factor Xa inhibitors, renin inhibitors, NEP inhibitors, vasopepsidase inhibitors, squalene synthetase inhibitors, anti-atherosclerotic agents, MTP inhibitors, calcium channel blockers, potassium channel activators, alpha-muscarinic agents, beta-muscarinic agents, anti-arrhythmic agents, diuretics, thrombolytic agents, anti-diabetic agents, mineralocorticoid receptor antagonists, growth hormone secretagogues, aP2 inhibitors, phophodiesterase inhibitors, anti-inflammatories, anti-proliferatives, antibiotics, farnesyl-protein transferase inhibitors, hormonal agents, plant-derived products, epipodophyllotoxins, taxanes, prenyl-protein transferase inhibitors, anti-TNF antibodies and soluble TNF receptors, and Cyclooxygenase-2 inhibitors. In another embodiment, the additional therapeutic agent is selected from alkylating agents, cancer immunotherapy monoclonal antibodies, antimetabolites, mitotic inhibitors, anti-tumor antibiotics, topisomerase inhibitors, photosensitizers, tyrosine kinase inhibitors, anti-cancer agents, and chemotherapeutic agents. In yet another embodiment, the additional therapeutic agent is an anti-cancer agent, such as paclitaxel and/or temozolomide.

In a particular embodiment, the disclosure provides a method for inhibiting Id-1 expression, cell proliferation, cell invasion, metastasis or a combination thereof in vivo and/or in vitro by administering a compound disclosed herein.

In a certain embodiment, the disclosure provides a method for treating a disease or disorder in a subject, comprising administering to a subject a therapeutically effective amount of a compound disclosed herein, wherein the disease or disorder can be ameliorated by inhibiting the expression of an Id polypeptide, by agonizing cannabinoid type 2 ("$CB_2$") receptors or a combination thereof. In a further embodiment, the disease or disorder is selected from the group of cancer, chronic pancreatitis, psoriasis, neoplasms, angiomas, endometriosis, obesity, age-related macular degeneration, retinopathies, restenosis, scaring, fibrogenesis, fibrosis, cardiac remodeling, pulmonary fibrosis, scleroderma, failure associated with myocardial infarction, keloids, fibroid tumors, stenting, Alzheimer's Disease, Parkinson's Disease, age related dementia, Huntington's Disease, and amyotrophic lateral sclerosis. Examples of cancer which can be treated with a compound disclosed herein include leukemia, melanoma, squamous cell carcinoma (SCC), hepatocellular carcinoma, colorectal adenocarcinoma, pancreatic cancer, lung cancer, kidney cancer, medullary thyroid cancer, papillary thyroid cancer, astrocytic tumor, neuroblastoma, Ewing's sarcoma, ovarian tumor, cervical cancer, endometrial carcinoma, breast cancer, prostate cancer, and malignant seminoma. In a certain embodiment, the cancer to be treated is a breast cancer or a brain cancer, such as glioblastoma multiforme. In another embodiment, the disclosure provides methods of treating chronic pain, neuropathic pain and neuropathies, spinal cord and head injuries, and radiation injury (e.g., following cancer treatment).

In a particular embodiment, a method of treating a disease or disorder in a subject comprises administering to a subject a therapeutically effective amount of a compound having the structure of:

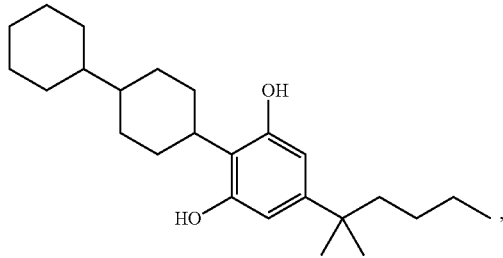 [SMILES: CCCCC(C)(C)c1cc(O)c(C2CCC(C3CCCCC3)CC2)c(O)c1]

or a pharmaceutically acceptable salt, or prodrug thereof, wherein the disease or disorder can be ameliorated by inhibiting the expression of an Id polypeptide, by activating $CB_2$ receptors or a combination thereof. In a further embodiment, the disease or disorder is selected from the group of leukemia, melanoma, SCC, hepatocellular carcinoma, colorectal adenocarcinoma, pancreatic cancer, lung cancer, kidney cancer, medullary thyroid cancer, papillary thyroid cancer, astrocytic tumor, neuroblastoma, Ewing's sarcoma, ovarian tumor, cervical cancer, endometrial carcinoma, breast cancer, prostate cancer, and malignant seminoma. In yet a further embodiment, the disease or disorder is a breast cancer or a brain cancer, such as glioblastoma multiforme. In another embodiment, the method of treating a disease or disorder with a compound disclosed herein further comprises administering to the subject one or more alkylating agents, cancer immunotherapy monoclonal antibodies, anti-metabolites, mitotic inhibitors, anti-tumor antibiotics, topoisomerase inhibitors, photosensitizers, tyrosine kinase inhibitors, anti-cancer agents, chemotherapeutic agents, or a combination thereof.

The details of one or more embodiments of the disclosure are set forth in the accompanying drawings and the description below. Other features, objects, and advantages will be apparent from the description and drawings, and from the claims.

BRIEF DESCRIPTION OF DRAWINGS

The accompanying drawings, which are incorporated into and constitute a part of this specification, illustrate one or more embodiments of the disclosure and, together with the detailed description, serve to explain the principles and implementations of the disclosure.

FIG. 1A-E provides data indicating that cannabidiol ("CBD") is an effective inhibitor of Id-1 expression, and thereby inhibits proliferation and invasiveness of MDA-MD231 breast cancer cells. (A) Depicts the results of a Boyden chamber invasion assay used to determine the effects of cannabinoids on the invasiveness of aggressive human breast cancer MDA-MB231 cells. Compounds were added at concentrations of 0.1 µM, 1.0 µM, or 1.5 µM. Data are presented as relative invasiveness of the cells through the Matrigel, where the respective controls are set as 100%. (B) Depicts Western blot analysis of proteins from MDA-MB231 cells treated with vehicle (control), 0.1 µM, 1.0 µM, or 1.5 µM of CBD for three days and analyzed as described below. (C) Provides a graph depicting the relative expression of Id-1 in treated cells/vehicle cells. Proteins from MDA-MB231 cells treated with additional cannabinoids for three days were extracted and analyzed for Id-1 expression by Western blot analysis. Normalization was carried out by stripping the blots and re-probing with a monoclonal anti-tubulin antibody. (D) Presents a graph depicting the inhibitory effect of 1.5 µM CBD on Id-1 expression compared over a time course of one-, two-, and three-days. (E) Presents data depicting the structure activity relationship of cannabinoids and the regulation of Id-1 protein expression. Proteins from MDA-MB231 cells treated with vehicle (control) or 1.5 µM of various cannabinoid compounds for two days were then analyzed for Id-1 expression by Western blot analysis. A high molecular weight non-specific band was used as a loading control (LC). Data are the mean of at least three replicates, bars±SE. Data were compared using a one-way ANOVA with a corresponding Dunnett's post-hoc test. (*) indicates statistically significant differences from control ($p<0.05$).

FIG. 2A-C presents data indicating that ectopic expression of Id-1 blocks the effect of CBD on MDA-MB231 invasiveness. (A) Provides representative light microscope images of control MDA-MB231 cells ((−)Id-1 cells, upper panels) and of MDA-MB231 cells that ectopically express Id-1 ((+)Id-1 cells, lower panels) that were treated with vehicle (control) or CBD (1.5 µM CBD) for two days, followed by an invasion assay performed overnight. (B) Provides data showing the relative invasiveness of the cells through the Matrigel, where the respective controls are set as 100%, and are the mean of at least three replicates, bars±SE. Data were compared using the unpaired Student's t-test. (*) indicates statistically significant differences from control (p<0.05). (C) Presents a Western blot showing the inhibitory effect of CBD on Id-1 expression in (−)Id-1 MDA-MB231 cells in comparison to (+)Id-1 MDA-MB231 cells.

FIG. 3A-C provides data indicating that CBD inhibits the expression of Id-1 gene at the mRNA and promoter levels in MDA-MB231 cells. (A) Presents the inhibition of the Id-1 gene product (434 bp) by CBD. Expression of the β-actin gene product (232 bp) was used as a control. (B) Provides luciferase activity in MDA-MB231 cells transiently transfected with Id-1-sbsluc as determined in the presence of vehicle (control) or CBD (1.5 µM). Cells were treated for 2 days and luciferase activity was measured. (C) Presents data for cells treated for 3 days. For both (B) and (C), all values were normalized for the amount of β-gal activity present in the cell extracts. Data are the mean of at least three replicates, bars±SE. The data are represented as percentage of activity of the treated cells/vehicle cells×100. Data were compared using the unpaired Student's t-test. (*) indicates statistically significant differences from control (p<0.05).

FIG. 4A-C provides that CBD produced a dose-dependent reduction of metastatic spread to the lung and increased the survival rate of mice. Lung metastases were generated in BALB/c mice by tail vein injection of $2\times10^4$ 4T1 cells. (A) One day after the injection, the tumor bearing mice were injected i.p. once a day with vehicle or CBD (0.1 to 5 mg/kg) for 14 days and percent metastasis was evaluated. Percent metastasis=total tumor number of lung metastatic foci in drug treated group/total number of lung metastatic foci in vehicle treated group where the respective controls (vehicle treated cells) were set as 100%. (B) Lung metastases measured in mice treated with vehicle or CBD 1 mg kg$^{-1}$ included those <2 mm and 2 mm. (C) Mice treated with vehicle or 1 mg kg$^{-1}$ CBD, starting a day after tail vein injection of $2\times10^4$ 4T1 cells, were observed until they demonstrated signs of disease progression that necessitated euthanasia. Survival between groups was compared using Kaplan-Meier analysis. **p<0.01 (unpaired Student't-test) and p<0.0001 (one-way ANOVA; *p<0.05, #p<0.001 Dunnett's post-hoc test).

FIG. 5A-C demonstrates that CBD decreases Id-1 expression and Ki-67 staining in lung metastatic foci. (A) Immunohistochemical detection of Id-1 and Ki67 was performed in lung tissues of vehicle (left) and CBD (right) treated 4T1-derived tumors. Nuclei are visible in blue (hematoxylin staining). Pictures are ×400 magnification. (B) The intensity of Id-1 expression is shown as follows: □, Negative; ▨, Weakly positive; ■, Strongly positive. The data are presented as a statistical analysis (lower panel). (C) The percentage of Ki67 positive cells per lung metastatic foci was also evaluated. *p<0.002 (unpaired Student's t-test).

FIG. 6A-C provides that CBD inhibited Id-1 and Ki67 expression in lung metastatic foci. (A) Immunohistochemical detection of Id-1 and Ki67 was performed in lung tissues of Vehicle (left) and CBD (right) treated mice. Nuclei are visible in blue (hematoxylin staining). Pictures of upper panels are ×200 magnification, and lower panels are ×400. (B) The intensity of the immunohistochemical (IHC) detection of Id-1 was graded from 0 to 4, and the percentage of cells per foci for each intensity level is shown as follows: □, grade 0; ▨, grade 1; ▨, grade 2; ▨, grade 3; ■, grade 4. (Right), the data are presented as a statistical analysis. (C) The percentage of Ki67 positive cells per lung metastatic foci was evaluated.

FIG. 7A-D provides that CBD reduced the formation of metastatic foci and increased the survival rate of mice in advanced stages of metastatic progression. Lung metastases were generated in BALB/c mice after tail vein injection of $2\times10^4$ 4T1 cells. (A) The pictures are representative of tumor formation observed at day five, seven, and nine. (B) Seven days after the injection of tumor cells, mice were injected i.p. once a day with vehicle, 0.5, 1 or 10 mg/kg CBD for seven days. % metastasis and (C) the number of lung metastatic foci±2 mm were compared between vehicle and CBD treated groups. p<0.05 (one-way ANOVA; *p<0.05, **p<0.01 Dunnett's post-hoc test). (D) Mice treated with vehicle or 1 mg/kg CBD, starting seven days after tail vein injection of $2\times10^4$ 4T1 cells, were observed until they demonstrated signs of disease progression that necessitated euthanasia. Survival between groups was compared using Kaplan-Meier analysis.

FIG. 8A-C presents data showing CDB produces a dose-dependent inhibition of tumor proliferation in-vivo. Tumors were generated by (A) injection of $5\times10^5$ 4T1 cells in the mammary fat pad of BALBc mice, or (B) by subcutaneous injection of $2\times10^6$ U251 cells into the flank of Nude mice. Daily treatment (systemic in (A) and peritumoral in (B) with CBD (mg/kg) was initiated one week after the initial injection of the cancer cells. The primary tumor volume was calculated by measuring the perpendicular largest diameters of the tumor with a caliper and using the formula (L×W$^2$/2). Representative samples show (C) that CBD eradicated a tumor in one of the NUDE mice.

FIG. 9 provides data showing the anti-metastatic activity of CBD against human breast cancer in a xenograph mouse model. Lung metastases were generated in Nude mice after tail vein injection of $1\times10^6$ MDA-MB231-luc-D3H2LN cells. One day after the injection, the tumor bearing mice were injected i.p. once a day with vehicle or 0.5 mg/kg and 1 mg/kg CBD for three weeks. Visible lung metastases were counted and measured by using a dissecting microscope. Data are represented as percent metastasis compared to control (vehicle) where the control has 100% metastasis.

FIG. 10A-B presents that CBD inhibited the formation of metastatic foci in later stages of metastatic progression. (A) Lung metastases were generated in BALB/c mice after tail vein injection of $20\times10^5$ mouse 4T1 cells. 1 mm$^3$ tumors could be visuallized through a dissecting scope on day 7, therefore, this was chosen as the time point to innitiate treatments. (B) One week after the tail vein injection of $20\times10^5$ mouse 4T1 cells, the tumor bearing mice were injected i.p. once a day with vehicle or 1 mg/kg and 10 mg/kg CBD for seven days. Visible lung metastases were counted and measured by using a dissecting microscope. Data are represented as percent metastasis compared to control (vehicle) where the control has 100% metastasis.

FIG. 11A-C presents data showing that at optimal combined ratios, CBD can enhance the ability of Paclitaxel to inhibit the viability of 4T1 breast cancer cells. (A) Concentration response curves were generated for Paclitaxel (PAC) and CBD alone and in combination. (B) The inhibitory values from the concentration response curves were used to calculate combination index (CI) values at multiple combination ratios. (C) These data were also used to calculate IC$_{50}$ values, the slope of the curve (m) and a goodness of fit value (r). Methods: Multiple viability assays in a 96 well format were run for each compound and the average percent inhibition of cell viability was calculated and transformed to fraction affected (Fa) e.g., percent inhibitory effect. Additional CI values and a dose reduction index (DRI) were also calculated using Compusyn software W. After determining the ($IC_{50}$/$Fa_{0.5}$) values of the drugs individually (C), components were then combined (B) at the following concentration ranges: controls, $0.125 \times IC_{50}$, $0.25 \times IC_{50}$, $0.5 \times IC_{50}$ and a combination index was calculated where CI<1, =1, and >1 indicate synergism, additive effect, and antagonism, respectively.

FIG. 12 provides a blot showing that treatment of U251 cells with CBD led to a concentration-dependent inhibition of Id-1 protein expression.

Figure 13:
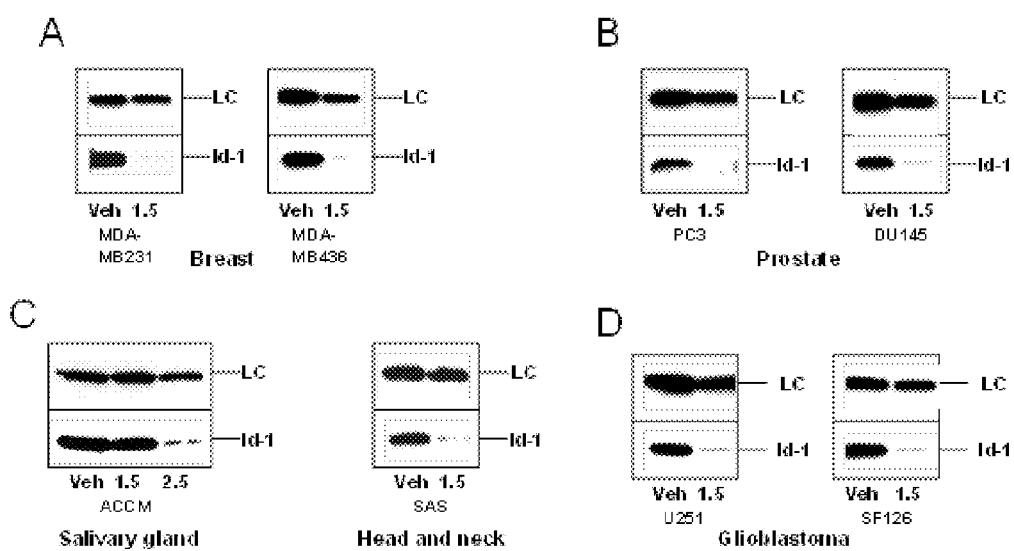
FIG. 13A-D provides data demonstrating that Id-1 protein expression is down-regulated by CBD in breast, prostate, salivary gland, head and neck cancer cells as well as in glioblastoma cells. (A) Effect of CBD on Id-1 protein expression in breast cancer cell lines, MDA-MB231 and MDA-MB436. (B) Effect of CBD on Id-1 protein expression in prostate cancer cell lines, PC3 and DU145. (C) Effect of CBD on Id-1 protein expression in salivary gland and head and neck cancer cell lines, ACCM and SAS, respectively. (D) Effect of CBD on Id-1 protein expression in gliobastoma cancer cell lines, U251 and SF126. LC: loading control; Veh: cells treated with vehicle control; 1.5: cells treated with 1.5 μM CBD; and 2.5: cells treated with 2.5 μM CBD.

μM). Proteins were extracted and analyzed for cleaved caspase 3, 7, 9 and PARP. Blots are representative of at least 3 independent experiments.

FIG. 23A-E presents that $CB_2$ activation and corresponding increases in oxygen radical formation are involved in the inhibitory effects of the cannabinoid combination treatment. The number of U251 cells staining positive for annexin (apoptosis) after 3 days treatment were measured using FACS analysis. Cells were treated with (A) a 4:1 combination of THC (1.7 μM) and CBD (0.4 μM), (B) 2.5 μM $\Delta^9$-THC, or (C) 2.0 μM CBD in the presence of 0.5 μM of the $CB_1$ antagonist, SR141716A ("SR1"), 0.5 μM of the $CB_2$ antagonist, SR144528 ("SR2") or 20 μM α-tocopherol ("TCP"). Percent control was calculated as positive annexin staining of the treated cells minus control cells. (D) The effects of cannabinoids on pERK activity were analyzed using Western analysis. α-tubulin was used as a loading control (LC). U251 cells were treated with vehicle or the indicated drugs for three days. (E) The production of cellular radical oxygen species (ROS)/$H_2O_2$ was measured using 2,7-dichlorodihydrofluorescein and FACS analysis. U251 cells were treated with vehicle or a 4:1 combination of $\Delta^9$-THC (1.7 μM) and CBD (0.4 μM). Data are the mean of at least 3 independent experiments, bars±SE. Data were compared using a one-way ANOVA with a Bonferroni's multiple comparison post-hoc analyses. (*) indicates statistically significant differences from control ($p<0.05$). (#) indicates statistically significant differences from the combination treatment of THC/CBD ($p<0.05$).

FIG. 24A-D demonstrates that the O-1663 CBD analog is more potent than CBD at inhibiting cancer cell growth and invasion, and Id-1 expression. (A) Provides the chemical structure of CBD and the O-1663 CBD analog. (B) CBD inhibition of MDA MB231 and U251 cancer cell growth as assessed by a MTT assay. (C) Cancer cells were treated with 1.0 μM of cannabinoid for two days and then analyzed for Id-1 protein expression. Normalization was carried out by stripping the blots and re-probing with a monoclonal anti-tubulin antibody. (D) MDA-MB231 breast cancer cells were treated with CBD (1.0 μM) or the O-1663 CBD analog (1.0 μM) for two days and then assessed for their ability to invade through a reconstituted extracellular matrix using the Boyden chamber assay; (*) indicates statistically significant difference from control ($p<0.05$); and (#) indicates statistically significant differences from CBD ($p<0.05$).

FIG. 25A-D provides a comparison of the O-1663 CBD analog and CBD for the inhibition of breast cancer cell proliferation/viability, invasion and Id-1 expression. (A) Mouse 4T1 and (B) human MDA-MB231 breast cancer cells were treated with vehicle, CBD or the O-1663 CBD analog for 2 days alone or in the presence of α-tocopherol ("TOC"), the CB1 receptor antagonist (SR141716A "SR1"), or the CB2 receptor antagonist (SR144528 "SR2"). Cell proliferation/viability was then evaluated using the MTT assay. (C) MDA-MB231 breast cancer cells were treated with CBD or the O-1663 CBD analog for 3 days alone or in the presence of TOC, SR1, or SR2. The ability of the cells to migrate and invade in modified Boyden chambers was then determined. The percentage relative proliferation/viability and invasion were calculated as the effect on treated cells/vehicle cells× 100. Respective controls (vehicle treated cells) were set as 100%. (D) Proteins from MDA-MB231 cells treated with vehicle (control), CBD (1.0 μM), or the O-1663 CBD analog (1.0 μM) for three days and were extracted and analyzed for Id-1 and Id-2 (marker of good prognosis and specificity for targeting Id-1) immunostaining using Western blot analysis. Data were compared using a one-way ANOVA with a corresponding Dunnett's post-hoc test. (*), (#), (δ) indicate statistically significant differences from control, CBD and O-1663 analog respectively ($p<0.01$).

FIG. 26A-D provides data showing that the O-1663 CBD analog targeted anti-tumor pathways unique to both CBD and THC and is more potent than CBD at generating ROS. (A) MDA-MB231 cells were treated with vehicle, CBD, THC or O-1663 CBD analog for two days. The production of ROS was then measured using 2'-7' dichloro-dihydrofluorescein and cell flow cytometry. (B) MDA-MB231 cells were treated with CBD or O-1663 CBD analog for two days in the presence or absence of SR2. (C) MDA-MB231 breast cancer cells were treated with vehicle, CBD, THC or O-1663 CBD analog for 2 days alone. The relative change in p8 mRNA expression (stress associated gene up-stream of autophagy) was evaluated. (D) Proteins from MDA-MB231 cells treated with vehicle, CBD, THC or O-1663 CBD analog for two days were extracted and analyzed for LC3 immunostaining (an autophagosome/autophagy marker) using Western blot analysis. Data are the mean of at least 3 independent experiments, bars±SE. Data were compared using a one-way ANOVA with a corresponding Dunnett's post-hoc test. (*) indicates statistically significant differences from control ($p<0.05$).

FIG. 27A-E demonstrates that the O-1663 CBD analog is more potent than CBD in inhibiting breast cancer metastasis. Lung metastases were generated in BALB/c mice by tail vein injection of $2\times10^4$ 4T1 cells. One day after the injection, the tumor bearing mice were injected i.p. once a day with vehicle, CBD or O-1663 CBD analog for 14 days. (A) Percent metastasis (total metastastic foci in treated/vehicle×100) and (B) the number of lung metastatic foci±2 mm were evaluated. (C) Lung metastases were generated in athymic nu/nu mice after tail vein injection of $5\times10^5$ MDA-MB231. One day after the injection, the tumor bearing mice were injected i.p. once a day with vehicle, CBD or O-1663 CBD analog for six weeks and the percent metastasis was compared. (D) Lung metastases were generated in BALB/c mice by tail vein injection of $2\times10^4$ 4T1 cells. One day after the injection, the tumor bearing mice were injected i.p. once a day with vehicle or 1 mg/kg of cannabinoids for 14 days. Percent metastasis and (E) the number of lung metastatic foci±2 mm were compared. $p<0.0001$ (one-way ANOVA; *$p<0.05$, Tukey's post-hoc test). n.s.=not significant.

FIG. 28A-C provides that the O-1663 CBD analog produced robust inhibition of advanced stage breast metastasis. Lung metastases were generated in BALB/c mice by tail vein injection of $2\times10^4$ 4T1 cells. One week after the injection, the tumor bearing mice were injected i.p. once a day with vehicle, CBD, or O-1663 CBD analog (0.5 and 1 mg/kg) for 14 days. (A) Percent metastasis (total metastastic foci in treated/vehicle×100) and (B) lung metastatic foci±2 mm were evaluated. (C) Mice treated with vehicle, CBD or O-1663 CBD analog (mg/kg) starting one week after tail vein injection of $2\times10^4$ 4T1 cells were observed until they demonstrated signs of disease progression that necessitated euthanasia. Survival between groups was compared using Kaplan-Meier analysis.

DETAILED DESCRIPTION

As used herein and in the appended claims, the singular forms "a," "and," and "the" include plural referents unless the context clearly dictates otherwise. Thus, for example, reference to "a compound" includes a plurality of such compounds and reference to "the cancer" includes reference to one or more cancers, and so forth.

Also, the use of "or" means "and/or" unless stated otherwise. Similarly, "comprise," "comprises," "comprising,"

"include," "includes," "including," "have," "haves," and "having" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of:"

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

For purposes of this disclosure, the term "alkyl" refers to an alkyl group that contains 1 to 30 carbon atoms. Where if the alkyl group contains more than 1 carbon, the carbons may be connected in a linear manner, or alternatively if there are more than 2 carbons then the carbons may also be linked in a branched fashion so that the parent chain contains one or more secondary, tertiary, or quaternary carbons. An alkyl may be substituted or unsubstituted, unless stated otherwise. Specific substituted alkyl groups include haloalkyl groups, particularly trihalomethyl groups, such as trifluoromethyl groups.

For purposes of this disclosure, the term "alkenyl" refers to an alkenyl group that contains 1 to 30 carbon atoms. While a $C_1$-alkenyl can form a double covalent bond to a carbon of a parent chain, an alkenyl group of three or more carbons can contain more than one double covalent bond. It certain instances the alkenyl group will be conjugated, in other cases an alkenyl group will not be conjugated, and yet other cases the alkenyl group may have stretches of conjugation and stretches of nonconjugation. Additionally, if there is more than 1 carbon, the carbons may be connected in a linear manner, or alternatively if there are more than 2 carbons then the carbons may also be linked in a branched fashion so that the parent chain contains one or more secondary, tertiary, or quaternary carbons. An alkenyl may be substituted or unsubstituted, unless stated otherwise.

For purposes of this disclosure, the term "alkynyl" refers to an alkynyl group that contains 1 to 30 carbon atoms. While a $C_1$-alkynyl can form a triple covalent bond to a carbon of a parent chain, an alkynyl group of three or more carbons can contain more than one triple covalent bond. Where if there is more than 1 carbon, the carbons may be connected in a linear manner, or alternatively if there are more than 3 carbons then the carbons may also be linked in a branched fashion so that the parent chain contains one or more secondary, tertiary, or quaternary carbons. An alkynyl may be substituted or unsubstituted, unless stated otherwise.

For purposes of this disclosure, the term "cylcloalkyl" refers to an alkyl that contains at least 3 carbon atoms but no more than 12 carbon atoms connected so that it forms a ring. A "cycloalkyl" for the purposes of this disclosure encompasses from 1 to 7 cycloalkyl rings, wherein when the cycloalkyl is greater than 1 ring, then the cycloalkyl rings are joined so that they are linked, fused, or a combination thereof. A cycloalkyl may be substituted or unsubstituted, or in the case of more than one cycloalkyl ring, one or more rings may be unsubstituted, one or more rings may be substituted, or a combination thereof. A "cycloalkyl group" can include bicyclic and tricyclic alkyl groups.

For purposes of this disclosure, the term "aryl" refers to a conjugated planar ring system with delocalized pi electron clouds that contain only carbon as ring atoms. An "aryl" for the purposes of this disclosure encompasses from 1 to 7 aryl rings wherein when the aryl is greater than 1 ring the aryl rings are joined so that they are linked, fused, or a combination thereof. An aryl may be substituted or unsubstituted, or in the case of more than one aryl ring, one or more rings may be unsubstituted, one or more rings may be substituted, or a combination thereof. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups.

For purposes of this disclosure, the term "heterocycle" refers to ring structures that contain at least 1 noncarbon ring atom. A "heterocycle," as used herein, encompasses from 1 to 7 heterocycle rings wherein when the heterocycle is greater than 1 ring the heterocycle rings are joined so that they are linked, fused, or a combination thereof. A heterocycle may be aromatic or nonaromatic, or in the case of more than one heterocycle ring, one or more rings may be nonaromatic, one or more rings may be aromatic, or a combination thereof. A heterocycle may be substituted or unsubstituted, or in the case of more than one heterocycle ring one or more rings may be unsubstituted, one or more rings may be substituted, or a combination thereof. Typically, the noncarbon ring atom is N, O, S, Si, Al, B, or P. In case where there is more than one noncarbon ring atom, these noncarbon ring atoms can either be the same element, or combination of different elements, such as N and O. Examples of heterocycles include, but are not limited to: a monocyclic heterocycle such as, aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide; and polycyclic heterocycles such as, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine. In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1]heptane.

For purposes of this disclosure, the terms "heterocyclic group", "heterocyclic moiety", "heterocyclic", or "heterocyclo" used alone or as a suffix or prefix, refer to a heterocycle that has had one or more hydrogens removed therefrom.

For purposes of this disclosure, the term "hetero-" when used as a prefix, such as, hetero-alkyl, hetero-alkenyl, hetero-alkynyl, or hetero-hydrocarbon, refers to the specified hydrocarbon group having one or more carbon atoms replaced by one or more non carbon atoms. Examples of such non carbon atoms include, but are not limited to, N, O, S, Si, Al, B, and P. If there is more than one non carbon atom in the hetero-chain then this atom may be the same element or may be a combination of different elements, such as N and O.

For purposes of this disclosure, the term "extended mixed ring system" refers to a group that is comprised of at least 2 ring structures, but no more than 7 ring structures. An "extended mixed ring system" is comprised of at least one ring functional group that is different from another ring functional group. Examples of ring groups include, but are not limited to, cycloalkyl, cycloalkenyl, cycloalkynyl, aryl, and heterocycle. Each ring may be optionally substituted. The rings comprising the mixed extended ring system may be joined so that they are linked, fused, or a combination thereof.

For purposes of this disclosure, the term "unsubstituted" with respect to hydrocarbons, heterocycles, and the like, refers to structures wherein the specified group contains no substituents.

For purposes of this disclosure, the term "substituted" with respect to hydrocarbons, heterocycles, and the like, refers to structures wherein the specified group contains one or more substituents.

For purposes of this disclosure, the term "substituent" refers to an atom or group of atoms substituted in place of a hydrogen atom. For purposes of this disclosure, a substituent would include deuterium atoms.

For purposes of this disclosure, the term "functional group" or "FG" refers to specific groups of atoms attached to a parent chain or located within a parent chain that are responsible for the characteristic chemical reaction of those molecules. While the same functional group will undergo the same or similar chemical reaction(s) regardless of the size of the molecule it is a part of, its relative reactivity can be modified by nearby functional groups. The atoms of functional groups are linked to each other and to the rest of the molecule by covalent bonds. Larger functional groups, such as hydrocarbons, esters, and heterocycles, can be optionally substituted. Examples of FG that are used in this disclosure include, but are not limited to, alkyls, alkenyls, alkynyls, aryls, hetero-alkyls, hetero-alkenyls, hetero-alkynyls, cycloalkyls, cycloalkenyls, cycloalkynyls, heterocycles, halos, hydroxyls, anhydrides, carbonyls, carboxyls, carbonates, carboxylates, aldehydes, haloformyls, esters, hydroperoxy, peroxy, ethers, orthoesters, carboxamides, amines, imines, imides, azides, azos, cyanates, isocyanates, nitrates, nitriles, isonitriles, nitrosos, nitros, nitrosooxy, pyridyls, sulfhydryls, sulfides, disulfides, sulfinyls, sulfos, thiocyanates, isothiocyanates, carbonothioyls, phosphinos, phosphonos, phosphates, silyls, and $Si(OH)_3$.

As used herein, a wavy line intersecting another line that is connected to an atom indicates that this atom is covalently bonded to another entity that is present but not being depicted in the structure. A wavy line that does not intersect a line but is connected to an atom indicates that this atom is interacting with another atom by a bond or some other type of identifiable association.

As used herein, a bond indicated by a straight line and a dashed line indicates a bond that may be a single covalent bond or alternatively a double covalent bond.

As used herein, the terms "CBD derivatives," "CBD analogs," "derivatives of CBD," or "analogs of CBD" are used interchangeably and refer to compounds that are both structurally and functionally related to cannabidiol. For example, a derivative of cannabidiol includes a compound of structural Formulas I, II, II(a), III or III(a).

The term "cannabinoids" generally refers to a group of substances that are structurally related to $\Delta^9$-tetrahydrocannabinol ("THC") or that bind to cannabinoid receptors. Plant cannabinoids are stable compounds with low toxicity profiles that are well tolerated by animals and humans during chronic administration. A variety of chemical classes of cannabinoids are useful in the methods provided herein including cannabinoids structurally related to THC, aminoalkylindoles, the eicosanoids related to the endocannabinoids, 1,5-diarylpyrazoles, quinolines and arylsulphonamides and additional compounds that do not fall into these standard classes but bind to cannabinoid receptors.

The term "pharmaceutically acceptable" as in pharmaceutically acceptable salt or pharmaceutically acceptable counter ion, refers to compounds, salts, or ions that are tolerated by a subject for topical, or internal use.

The term "pharmaceutically acceptable salt" refers to making a salt formation of a compound disclosed herein. Salt formation can be used as a means of varying the properties of the compounds disclosed herein, for example, to increase or decrease solubility of the compounds, to improve stability of the compounds, to reduce toxicity of the compounds, and/or to reduce the hygroscopicity of the compounds. There are a wide range of chemically diverse acids and bases, with a range of pKa values, molecular weights, solubilities and other properties, that can used for making pharmaceutically acceptable salts of the compounds disclosed herein. Examples of pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the disclosure can form pharmaceutically acceptable salts with various amino acids. Examples of pharmaceutically acceptable base addition salts include, but are not limited to, aluminum, calcium, lithium, magnesium, potassium, sodium, zinc, and diethanolamine salts. For additional examples of pharmaceutical salts that can used to practice this disclosure, see P. H. Stahl and C. G. Wermuth (eds.), *Pharmaceutical Salts Properties, Selection, and Use* (2d ed. 2011) Wiley and Sons Publisher, ISBN: 978-3-90639-051-2.

The term "pharmaceutically acceptable counter ion" either refers to pharmaceutically acceptable cations including, but not limited to, alkali metal cations (e.g., $Li^+$, $Na^+$, $K^+$), alkaline earth metal cations (e.g., $Ca^{2+}$, $Mg^{2+}$), non-toxic heavy metal cations and ammonium ($NH_4^+$) and substituted ammonium ($N(R')_4^+$, where R' is hydrogen, alkyl, or substituted alkyls, i.e., including, methyl, ethyl, or hydroxyethyl, specifically, trimethyl ammonium, triethyl ammonium, and triethanol ammonium cations); or pharmaceutically-acceptable anions including, but not limited to, halides (e.g., $Cl^-$, $Br^-$), sulfate, acetates (e.g., acetate, trifluoroacetate), ascorbates, aspartates, benzoates, citrates, and lactate.

The term "metastasis" generally refers to a multi-step process by which aggressive cancer cells spread out of the primary tissue and into other tissues of the body. Aggressive cancer cells that are nourished through angiogenesis, can migrate out of the primary tissue, and invade into the blood stream. These migratory aggressive cancer cells can remain vital by escaping the immune response, and consequently evade the blood stream and invade other tissues of the body. These cells can then proliferate to create secondary tumors.

A "cell proliferative disorder" is any cellular disorder in which the cells proliferate more rapidly than normal tissue growth. Thus a "proliferating cell" is a cell that is proliferating more rapidly than normal cells. A proliferative disorder can include but is not limited to neoplasms.

A "neoplasm" refers to an abnormal tissue growth, generally forming a distinct mass that grows by cellular proliferation more rapidly than normal tissue growth. Neoplasms show partial or total lack of structural organization and functional coordination with normal tissue. These can be broadly classified into three major types. Malignant neoplasms arising from epithelial structures are called carcinomas, malignant neoplasms that originate from connective tissues such as muscle, cartilage, fat or bone are called sarcomas and malignant tumors affecting hematopoetic structures (structures pertaining to the formation of blood cells) including components of the immune system, are called leukemias and lymphomas. Unless stated otherwise, a "neoplasm" as used herein refers to all types of neoplasms. A tumor is the neoplastic growth of the disease cancer. As used herein, a neoplasm, also referred to as a "tumor", encompasses hematopoietic neoplasms as well as solid neoplasms. Other neoplasm based disorders include, but are not limited to neurofibromatosis, melanoma, breast cancers, head and neck cancers (e.g., brain cancers such as glioblastoma multiforme), gastrointestinal cancers and the like. A cancer generally refers to any neoplastic disorder, including such cellular disorders as, for example, brain cancer, glioblastoma multiforme (GBM), renal cell cancer, Kaposi's sarcoma, chronic leukemia, breast cancer, sarcoma, ovarian carcinoma, rectal cancer, throat cancer, melanoma, colon cancer, bladder cancer, mastocytoma, lung cancer and gastrointestinal or stomach cancer.

A "subject" generally refers to mammals such as human patients and non-human primates, as well as experimental animals such as rabbits, rats, and mice, and other animals. Animals include all vertebrates, e.g., mammals and non-mammals, such as sheep, dogs, cows, chickens, amphibians, and reptiles.

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure. Moreover, with respect to similar or identical terms found in the incorporated references and terms expressly defined in this disclosure, the term definitions provided in this disclosure will control in all respects.

Activation of the two cannabinoid receptors, cannabinoid receptor 1 ("$CB_1$") and cannabinoid receptor 2 ("$CB_2$"), can lead to the inhibition of cell proliferation and induction of apoptosis in multiple types of cancer cell lines resulting in the reduction of tumor growth in vivo. The $CB_1$ and $CB_2$ receptors are members of the G-protein coupled receptor (GPCR) superfamily, and can interact with five structurally distinct classes of compounds. These include the plant-derived classical cannabinoids, such as THC and CBN; the non-classical bicyclic cannabinoid agonists, such as CP55, 940; the endogenous cannabinoid agonists, such as anandamide (AEA); and the aminoalkylindole (AAI) agonists, such as WIN55, 212-2; and the antagonist/inverse agonists, such as SR141716A.

Interaction sites, independent of $CB_1$ and $CB_2$ receptors, may also be responsible for the anticancer activity of cannabinoids. There are more than 60 cannabinoids in *Cannabis sativa*. In addition to THC, the compounds cannabidiol ("CBD"), cannabinol ("CBN"), and cannabigerol ("CBG") are also present in reasonable quantities. CBN has low affinity for $CB_1$ and $CB_2$ receptors, whereas the non-psychotropic cannabinoids, CBD and CBG, have negligible affinity for the cloned receptors.

The studies presented herein demonstrated that the helix-loop-helix protein Id-1, an inhibitor of basic helix-loop-helix (bHLH) transcription factors, plays a crucial role during breast cancer progression. Id-1 stimulates proliferation, migration and invasion in breast cancer cells. Moreover, targeting Id-1 expression partially in breast cancer cells reduces invasion and breast cancer metastasis in vitro and in preclinical animal models. The disclosure provides that Id-1 is a therapeutic target for treating disorders and diseases associated with Id polynucleotide expression. The disclosure further provides that Id-associated cell proliferative disorders, such as breast cancer, can be treated by inhibiting Id-1 expression and/or activity. This approach may be highly effective and safe in advanced breast cancer patients, given (1) the relationship between high Id-1 expression levels and aggressive breast cancer cell behaviors; (2) partial reduction in Id-1 activity can achieve significant outcomes; and (3) Id-1 expression is low in normal adult tissues, thereby eliminating unwanted toxicities generally associated with currently available therapeutic modalities.

Id-1 protein plays a key role in the malignant progression of many aggressive and invasive human cancers such as: leukemia, melanoma, hepatocellular carcinoma, colorectal adenocarcinoma, pancreatic cancer, lung cancer, kidney cancer, medullary thyroid cancer, papillary thyroid cancer, astrocytic tumor, neuroblastoma, Ewing's sarcoma, ovarian tumor, cervical cancer, endometrial carcinoma, breast cancer, prostate cancer, malignant seminoma, and squamous cell carcinomas, such as esophageal cancer, and head and neck cancer. Accordingly, Id-1 associated cell proliferative disorders include, but are not limited to, leukemias, melanomas, squamous cell carcinomas (SCC) (e.g., head and neck, esophageal, and oral cavity), hepatocellular carcinomas, colorectal adenocarcinomas, pancreatic cancers, lung cancers, kidney cancers, medullary thyroid cancers, papillary thyroid cancers, astrocytic tumors, neuroblastomas, Ewing's sarcomas, ovarian tumors, cervical cancers, endometrial carcinomas, breast cancers, prostate cancers, and malignant seminomas.

Approaches for targeting Id-1 expression include gene therapy using antisense oligonucleotide, siRNA, non-viral or viral plasmid-based strategies. In addition, the development of new strategies to modulate Id-1 expression/functional activity includes the identification of small molecules that modulate the activity of Id-1. A range of small molecules that target the molecular pathology of cancer are now being developed, and a significant number of them are being tested in ongoing human clinical trials.

The disclosure demonstrates that the compounds disclosed herein are inhibitors of Id-1 expression and modulate other Id-helix-loop-helix protein expression, such as Id-2. The use of the compounds disclosed herein, therefore, represents a novel strategy for the treatment of cancer.

Metastasis is the final and often fatal step in the progression of aggressive cancers. Currently available therapeutic strategies at this stage of cancer progression are often non-specific, have only marginal efficacy and are highly toxic. This is in part due to the lack of knowledge about the molecular mechanisms regulating the development of aggressive cancers. Therapeutic approaches targeting only specific mechanisms involved in the development of aggressive cancers are in urgent need. The expectation would be that this strategy would reduce unwanted toxicities associated with the therapy itself.

The compounds disclosed herein were found to down-regulate Id-1 expression in metastatic foci of the lung and corresponding breast cancer metastasis in mice. Moreover, the O-1663 CBD analog was found to be unexpectedly more potent than CBD and other compounds at inhibiting breast cancer metastasis in a mouse model where tumor cell aggressiveness is highly dependent on the expression of Id-1. In addition, data provided herein indicates that the compounds disclosed herein were surprisingly effective in inhibiting cell proliferation and invasiveness, and could induce cell death in-vitro and in-vivo.

Human GBMs are highly heterogeneous and vary in their response to therapeutic treatments. As described herein, this heterogeneity is reflected in the response of multiple aggressive GBM cancers cell lines to the anti-proliferative activity of synthetic and naturally occurring cannabinoids. The disclosure also provides for other constituents of marijuana, such as THC, that inhibit GBM cell growth and induces apoptosis. The disclosure demonstrates that the addition of CBD or CBD-based analogs to THC improves the overall potency and efficacy of THC in the treatment of cancer.

The compounds disclosed herein were shown to inhibit Id-1 expression and tumor progression in a mouse model of brain cancer. In particular, the O-1663 CBD analog was found to be particularly effective in inhibiting Id-1 and corresponding cell proliferation and invasion by breast cancer cells and other aggressive cancerous cells.

Compositions comprising compounds disclosed herein were found to modulate Id-1 and Id-2 expression in tested cancer cell lines. Moreover, as Id-1 expression was found to be up-regulated during the progression of almost all types of solid tumors investigated, compositions comprising compounds disclosed herein can provide a generalized therapeutic strategy for the treatment of various aggressive cancers. Accordingly, provided herein are methods for modulating the activity of a metastatic cell by regulating the activity of a target Id polypeptide by using a compound disclosed herein. For the purposes of this disclosure, "regulating the activity of a target Id polypeptide" can also include: (1) mechanisms for modulating endogenous nucleic acid sequences which encode a target Id protein so that Id polypeptide levels are decreased in a cell; (2) introducing exogenous nucleic acid sequences that inhibit Id mRNA and/or protein expression in a cell; and (3) increasing the turnover rate of endogenous Id polypeptides such that Id polypeptide levels are decreased in a cell.

In a particular embodiment, the disclosure provides methods that can be used to identify substances that modulate the biological activity of an Id polypeptide, such as by modulating the expression of an Id nucleic acid sequence which encodes an Id polypeptide. In another embodiment, a method disclosed herein can be used to identify one or more compounds that bind to Id regulatory sequences. In yet another embodiment, a method disclosed herein can be used to identify one or more substances which modulate the biological activity of Id polypeptide by affecting the half-life of an Id polypeptide.

In a particular embodiment, the disclosure provides methods for treating cell proliferation disorders by administering one or more compounds disclosed herein. In general, these methods can be used to treat disorders related to neoplastic cells and the metastasis thereof. In a certain embodiment, the disclosure provides methods for treating cell proliferation disorders by administering one or more compounds disclosed herein which regulate the expression and/or activity of endogenous Id polypeptides and/or the half-life of endogenous Id polypeptides. In a further embodiment, the disclosure provides methods for treating disorders that can be ameliorated by modulating one or more Id polypeptides expression.

The disclosure also pertains to the field of predictive medicine in which diagnostic assays, prognostic assays, pharmacogenomics, and monitoring clinical trails are used for prognostic (predictive) purposes to thereby treat an individual prophylactically. As such, the disclosure contemplates use of methods provided herein to screen, diagnose, stage, prevent and/or treat disorders characterized by expression or over-expression of an Id helix-loop-helix polypeptide, such as Id-1. Accordingly, a subject can be screened to determine the level of a particular Id's expression or activity. A subject with a cell proliferative disorder can also be screened to determine whether abnormally proliferating cells would be susceptible to techniques disclosed herein, including inhibiting the expression or over expression of an Id polypeptide.

The disclosure also provides for prognostic (or predictive) assays for determining whether an individual is at risk of developing a disorder associated with elevated/reduced expression of a target Id polypeptide. Such assays can be used for prognostic or predictive purpose to thereby prophylactically treat an individual prior to the onset of a disorder characterized by or associated with over expression or activity of a target Id polypeptide, such as Id-1.

As described herein the compounds disclosed herein are significantly more effective than other cannabinoid compounds at inhibiting the expression of genes and proteins that modulate cancer aggressiveness (e.g. Id-1) in, for example, breast cancer aggressiveness. The data also indicate that Id-1 is a key factor for breast cancer cell aggressiveness. The down-regulation of gene expression of Id-1 resulted from inhibiting the endogenous Id-1 promoter. As shown in the FIGS. presented herein, CBD and the 0-1663 CBD analog effectively inhibits the expression of Id-1 in metastatic breast cancer cells and GBM cells.

To determine general structural components of CBD that were responsible for its inhibitory activity, CBD was compared against structurally related cannabinoid compounds for their ability to inhibit Id-1 (e.g., see FIG. 1). $\Delta^9$-Tetrahydrocannabinol ("THC") had no activity against Id-1. THC is structurally related to CBD with the primary exception being that the B ring or 1,1'-di-methyl-pyrane ring (e.g. see FIG. 1, panel E) of THC has been opened in CBD. CP55, 940 was a compound that inhibited Id-1 expression, however, it was still less effective than CBD.

As presented herein, cannabinoids CBD and THC are effective at inhibiting breast cancer progression. However, they each target unique pathways. In a mouse model of metastasis, a detailed pharmacological assessment of the non-toxic agent, CBD, revealed the drugs ability to significantly extend survival. This effect was found to be directly related to down-regulation of Id-1 expression in vivo. In addition, it was found that CBD could reduce the number and size of metastatic foci in advanced stages of breast cancer metastasis. Treatment with CBD in advanced stage models of metastasis also resulted in moderate increases in survival. In hopes of generating more potent and efficacious therapeutic compounds for treating cell proliferative disorders, analogs based on the CBD structure were screened for inhibiting breast cancer viability/proliferation, and invasion and Id-1 expression. These CBD based analogs were also screened to see if they were active at targeting $CB_2$ receptors. The analogs disclosed herein were developed so as to have desirable properties from both THC and CBD, achieving a synergy not possible by administering THC or CBS alone. By dual targeting each unique antitumor pathway with a single compound, results in a robust synergistic inhibition of advanced stages of metastasis without the drawbacks and side effects of administering each compound individually.

Based upon initial screening assays, a CBD analog was found that was more potent than CBD in inhibiting Id-1 expression, and retarded cell proliferation, metastasis, and invasion by various cancer cell lines (e.g., see FIGS. 24-30). This analog, termed O-1663, is a cannabidiol derivative which has 2 linked unsubstituted cyclohexyl rings instead of the substituted cyclohexylalkenyl ring of cannabidiol. Moreover, the O-1663 CBD analog contains an aliphatic $C_5$ alkyl group which contains 1,1-dimethyl substitutions. The data provided herein show that the unique activity (Id-1 inhibition) of the O-1663 CBD analog can be attributed in-part to hydrophobic cycloalkyl rings and the possession of an extended substituted alkyl side chain. The results from the O-1663 CBD analog provide a basis for generating additional compounds using rational drug design so as to generate even more potent and efficacious therapeutics.

In a particular embodiment, the disclosure provides for a compound having the structure of Formula I:

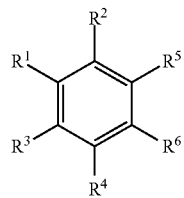

(I)

or a pharmaceutically acceptable salt, or prodrug thereof, wherein:

$R^1$ is selected from the group comprising an optionally substituted $(C_5-C_{12})$alkyl, an optionally substituted hetero-$(C_5-C_{12})$alkyl, an optionally substituted $(C_5-C_{12})$alkenyl, an optionally substituted hetero-$(C_5-C_{12})$alkenyl, an optionally substituted $(C_5-C_{12})$alkynyl, an optionally substituted hetero-$(C_5-C_{12})$alkynyl, an optionally substituted $(C_5-C_{12})$cycloalkyl, an optionally substituted $(C_5-C_{12})$ cycloalkenyl, an optionally substituted $(C_5-C_{12})$ cycloalkynyl, an optionally substituted $(C_4-C_{11})$heterocycle, an optionally substituted aryl, and an optionally substituted extended mixed ring system;

$R^2$-$R^3$ are each independently selected from the group comprising hydroxyl, $(C_1-C_2)$alkoxy, carboxylic acid, amine, halo, cyano, or $(C_1-C_3)$ester;

$R^4$-$R^5$ are each independently selected from the group comprising hydrogen, hydroxyl, $(C_1-C_2)$alkoxy, carboxylic acid, amine, halo, cyano, and ester;

$R^6$ is selected from the group comprising an optionally substituted $(C_1-C_{12})$alkyl, an optionally substituted hetero $(C_1-C_{11})$alkyl, an optionally substituted $(C_1-C_{12})$alkenyl, an optionally substituted hetero$(C_1-C_{11})$alkenyl, an optionally substituted $(C_1-C_{12})$alkynyl, and an optionally substituted hetero$(C_1-C_{11})$alkynyl.

In a certain embodiment, in the case of a compound having a structure of Formula I:

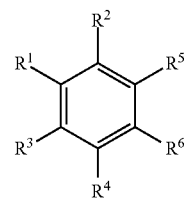

(I)

where $R^2$ and $R^3$ are hydroxyls, $R^6$ is an alkyl, or substituted alkyl of at least 6 carbon atoms, and $R^1$ is a cyclohexylalkenyl with the general structure of

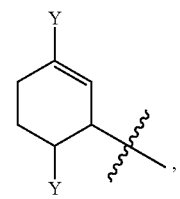

then Y is not selected from the group consisting of a H, —OH, aryl, substituted aryl, alkyl, substituted alkyl, carboxyl, aminocarbonyl, alkylsulfonylaminocarboxyl, and alkoxycarbonyl.

In another embodiment, in the case of a compound having structure of Formula I:

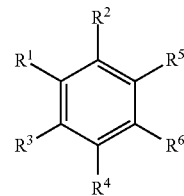

(I)

where $R^6$ is a 1,1-dimethyl-heptyl group, $R^2$ and $R^3$ are hydroxyls, and $R^4$ and $R^5$ are hydrogens, then $R^1$ is not selected from the group consisting of:

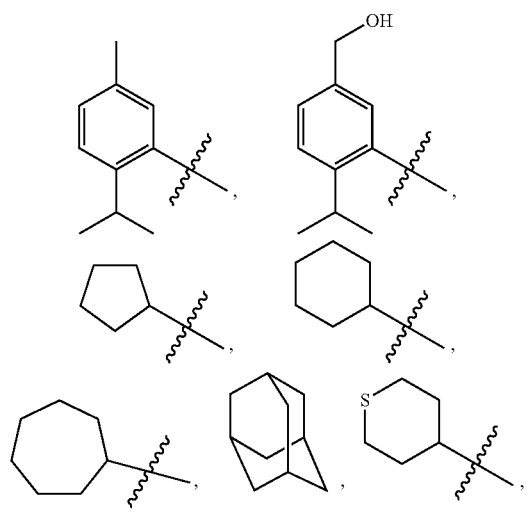

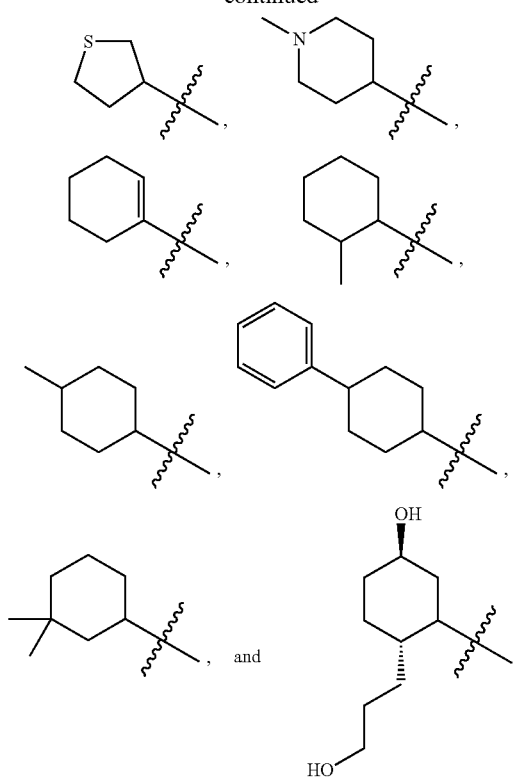

In a certain embodiment, in the case of a compound having structure of Formula I:

(I)

where $R^6$ is a 1,1-dimethyl-heptyl group, $R^2$ and $R^3$ are methoxys, and $R^4$ and $R^5$ are hydrogens, then $R^1$ is not selected from the group consisting of:

In a certain embodiment, in the case of a compound having a structure of Formula I:

(I)

where $R^6$ is a methyl, n-propyl group, n-butyl group, or n-pentyl group, $R^2$ is a hydroxyl, $R^3$ is a hydroxyl or methoxy, $R^4$ is hydrogen or carboxylic acid, and $R^5$ is hydrogen, then $R^1$ is not selected from the group consisting of:

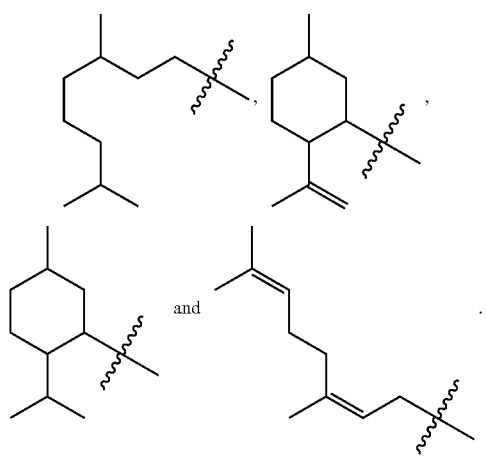

In another embodiment, in the case of a compound having a structure of Formula I:

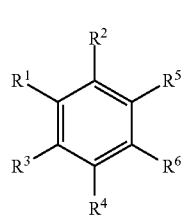
(I)

where $R^6$ is a 1,1-dimethyl-butyl group, $R^2$ and $R^3$ are hydroxyls, and $R^4$ and $R^5$ are hydrogen, then $R^1$ is not

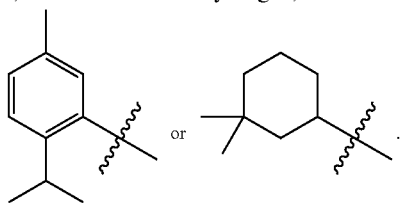

In another embodiment, in the case of a compound having a structure of Formula I:

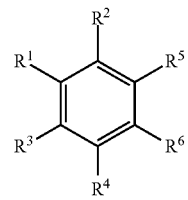
(I)

where $R^6$ is a methyl group, $R^2$ and $R^3$ are methoxys, and $R^4$ and $R^5$ are hydrogen, then $R^1$ is not

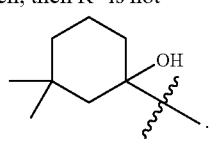

In a further embodiment, the disclosure provides for a compound having a structure of Formula I, wherein $R^1$ is selected from the group comprising:

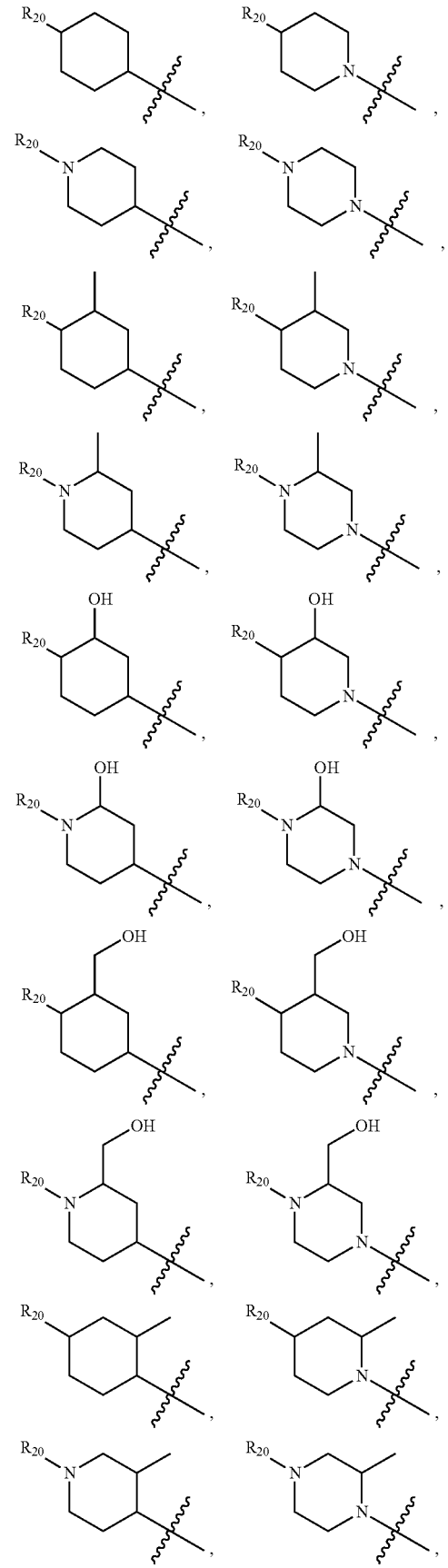

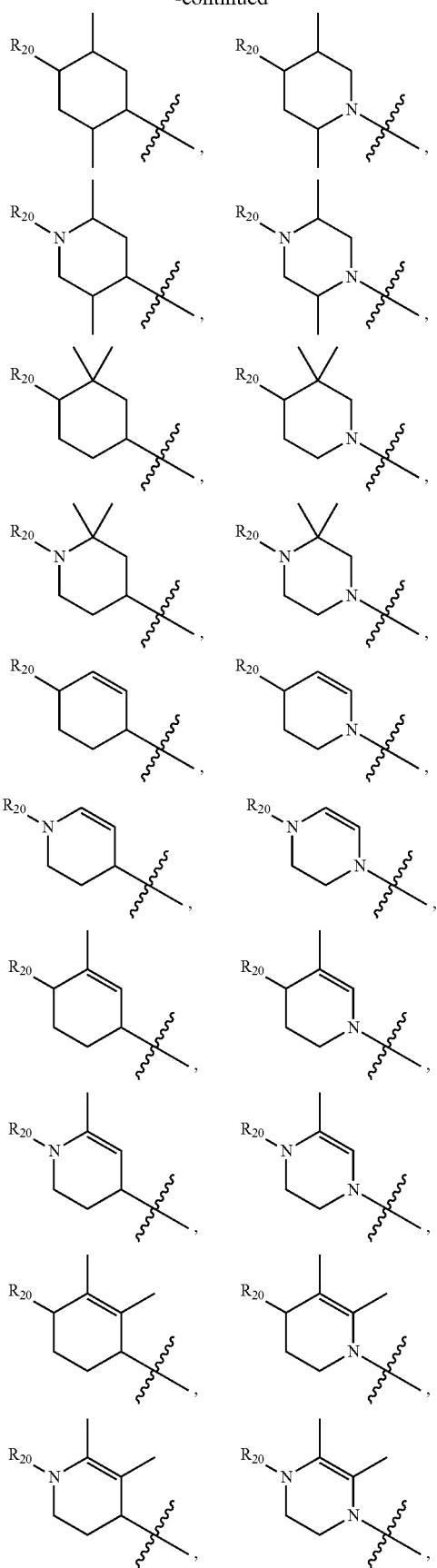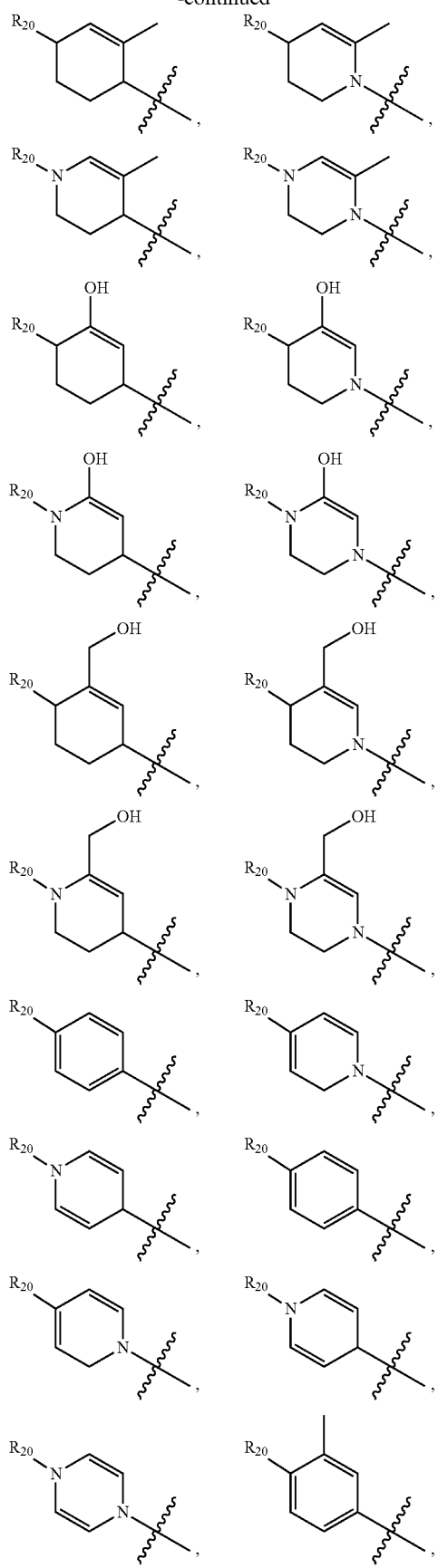

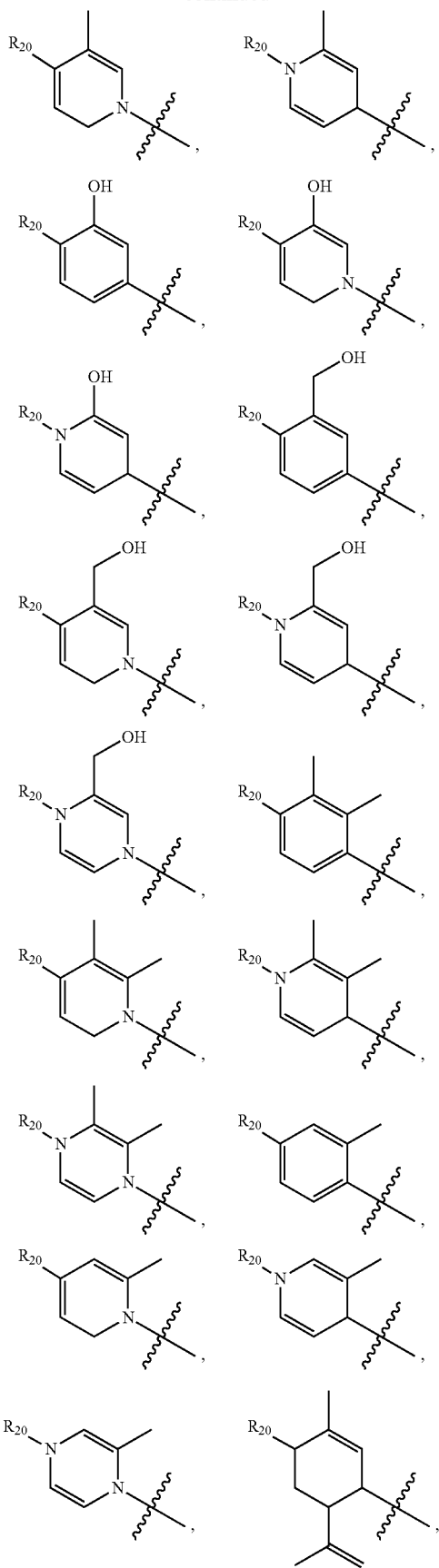

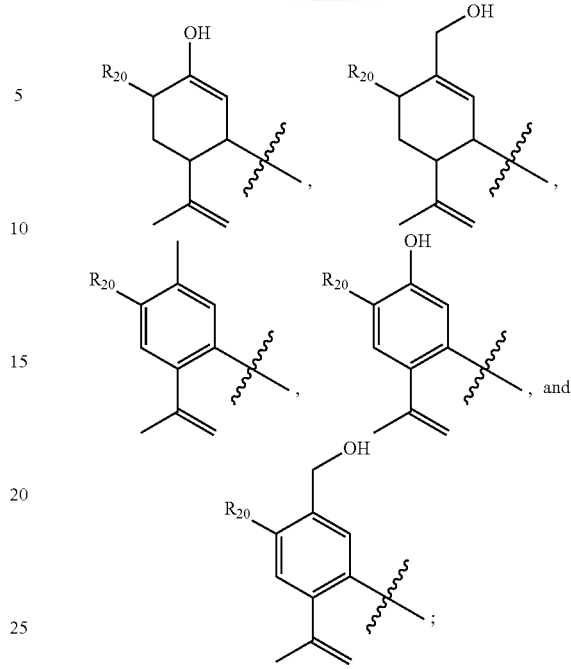

and wherein $R^{20}$ is selected from the group comprising hydrogen, deuterium, FG, optionally substituted $(C_5-C_{12})$alkyl, optionally substituted hetero-$(C_5-C_{12})$ alkyl, optionally substituted $(C_5-C_{12})$ alkenyl, optionally substituted hetero-$(C_5-C_{12})$alkenyl, optionally substituted$(C_5-C_{12})$alkynyl, optionally substituted hetero-$(C_5-C_{12})$alkynyl, optionally substituted $(C_5-C_{12})$cycloalkyl, optionally substituted $(C_5-C_{12})$cycloalkenyl, optionally substituted $(C_5-C_{12})$cycloalkynyl, optionally substituted $(C_4-C_{11})$heterocycle, optionally substituted aryl, or optionally substituted extended mixed ring system.

In a certain embodiment, the disclosure provides for a compound of Formula I, having the structure of Formula II:

(II)

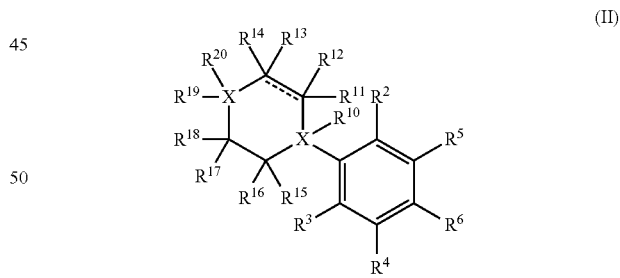

or a pharmaceutically acceptable salt, or prodrug thereof, wherein:

X is independently C or N;

$R^2$-$R^3$ are each independently selected from the group comprising hydroxyl, $(C_1-C_2)$alkoxy, carboxylic acid, amine, halo, cyano, and $(C_1-C_3)$ ester;

$R^4$-$R^5$ are each independently selected from the group comprising hydrogen, deuterium, hydroxyl, $(C_1-C_2)$alkoxy, carboxylic acid, amine, halo, cyano, and $(C_1-C_3)$ ester;

$R^6$ is selected from the group comprising unsubstituted $(C_1-C_{12})$ alkyl, unsubstituted hetero $(C_1-C_{11})$ alkyl, unsubstituted ($C_1$-$C_{12}$) alkenyl, unsubstituted hetero ($C_1$-$C_{11}$) alkenyl, unsubstituted ($C_1$-$C_{12}$) alkynyl, and unsubstituted hetero ($C_1$-$C_{11}$) alkynyl;

$R^{10}$-$R^{19}$ are each independently selected from the group comprising hydrogen, deuterium, FG, optionally substituted ($C_1$-$C_8$)alkyl, optionally substituted hetero($C_1$-$C_8$)alkyl, optionally substituted ($C_1$-$C_8$)alkenyl, optionally substituted hetero($C_1$-$C_8$)alkenyl, optionally substituted ($C_1$-$C_8$)alkynyl, optionally substituted hetero($C_1$-$C_8$)alkynyl, optionally substituted ($C_5$-$C_8$)cycloalkyl, optionally substituted ($C_5$-$C_8$)cycloalkenyl, optionally substituted ($C_5$-$C_8$)cycloalkynyl, optionally substituted ($C_4$-$C_8$)heterocycle, optionally substituted extended mixed ring system; and $R^{20}$ is selected from the group comprising an optionally substituted ($C_5$-$C_{12}$)cycloalkyl, an optionally substituted ($C_5$-$C_{12}$)cycloalkenyl, an optionally substituted ($C_5$-$C_{12}$)cycloalkynyl, an optionally substituted ($C_4$-$C_{11}$)heterocycle, a substituted aryl, an optionally substituted aryl having more than two rings, and an optionally substituted extended mixed ring system.

In another embodiment, the disclosure provides a compound of Formula II, wherein $R^{20}$ is an optionally substituted ($C_5$-$C_7$)cycloalkyl, an optionally substituted ($C_5$-$C_7$)cycloalkenyl, a substituted aryl, an optionally substituted aryl of two or more rings, an optionally substituted heterocycle, wherein the heterocycle contains 4, 5, or 6 ring atoms.

In yet another embodiment, the disclosure provides a compound of Formula II, wherein $R^{20}$ is an optionally substituted heterocycle containing 4, 5, or 6 ring atoms selected from the group comprising:

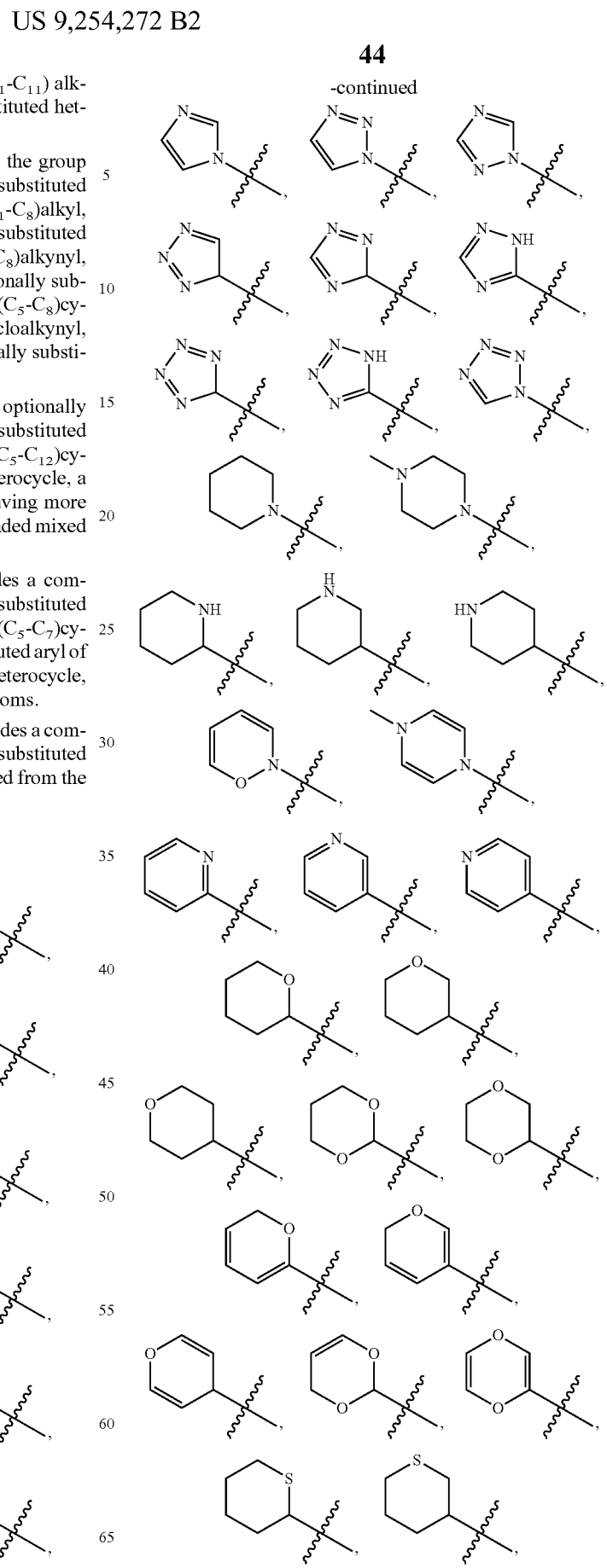

-continued
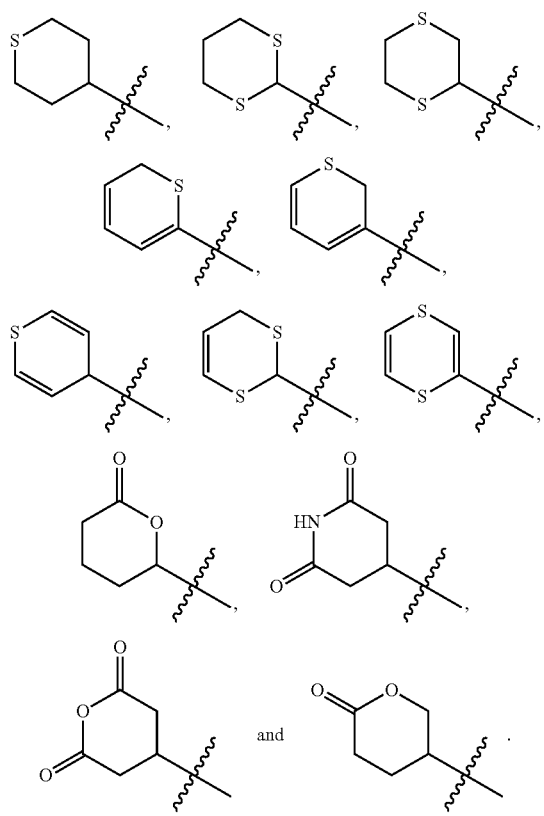
In yet another embodiment, the disclosure provides a compound of Formula II, wherein $R^{20}$ is a substituted aryl or an optionally substituted aryl having 2 or more rings selected from the group comprising:
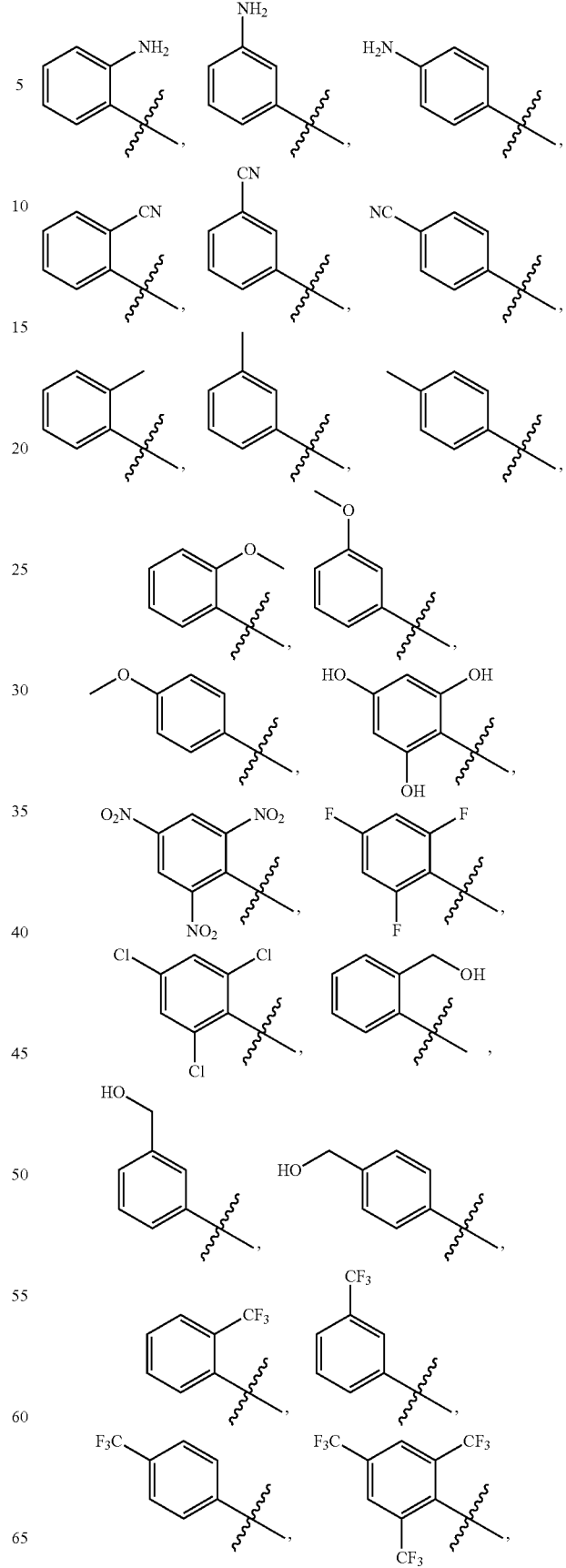

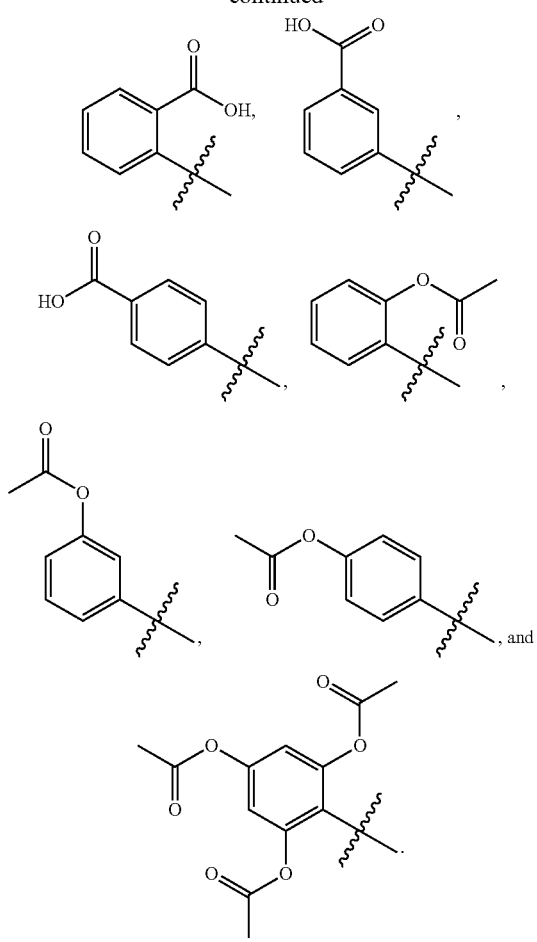
In a particular embodiment, the disclosure provides a compound of Formula II, wherein $R^{20}$ is an optionally substituted $(C_5-C_7)$cycloalkyl ring selected from the group comprising:
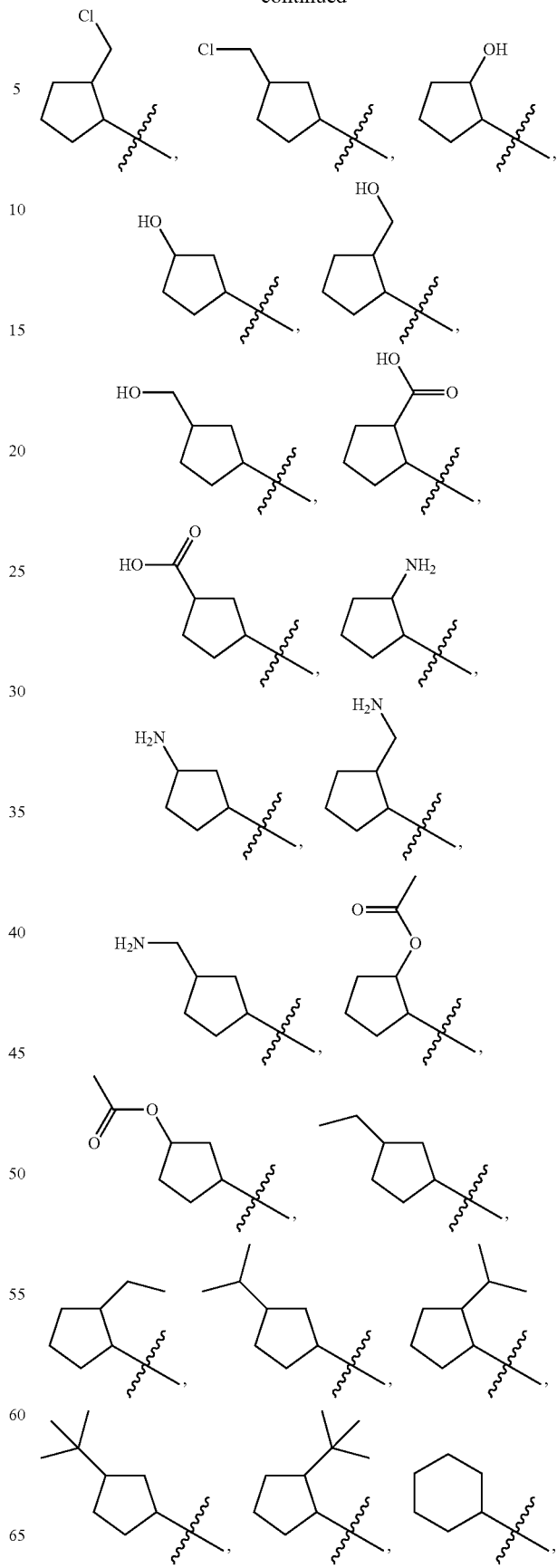

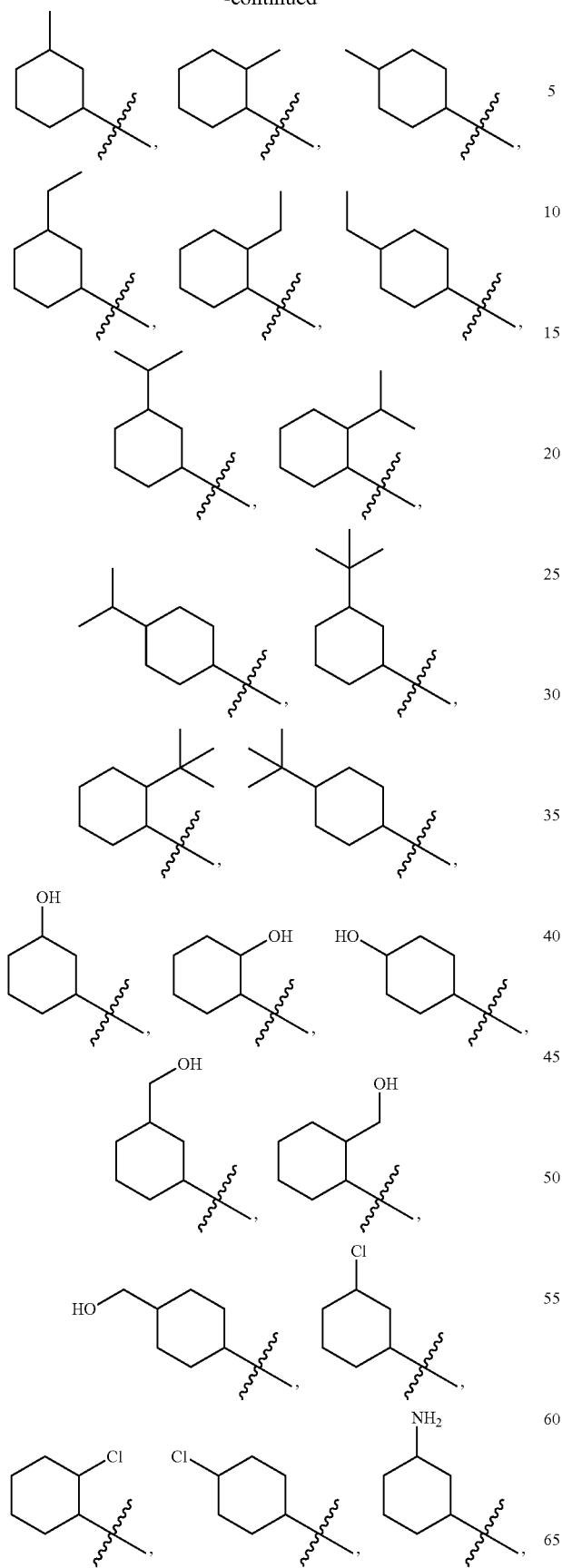
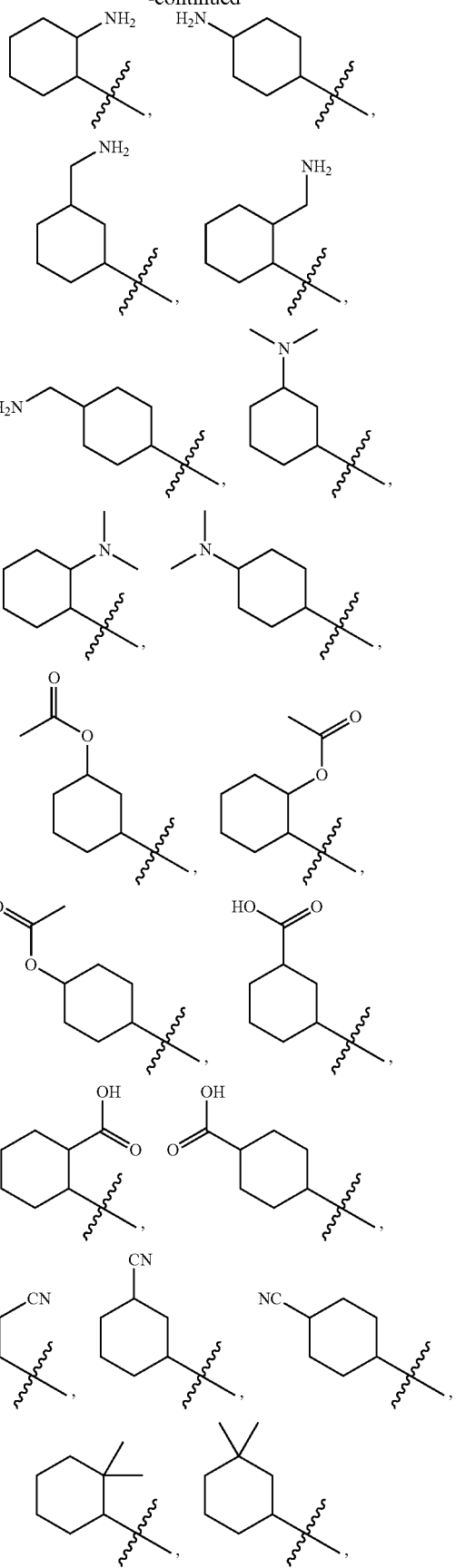

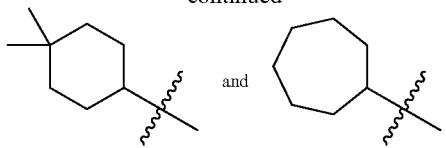

In another embodiment, the disclosure provides for a compound of Formula I, having the structure of Formula II(a):

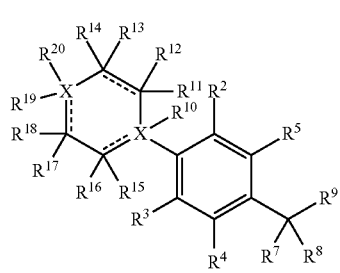

II(a)

or a pharmaceutically acceptable salt, or prodrug thereof, wherein:

X is independently C or N;

$R^2$-$R^3$ are each independently selected from the group comprising hydroxyl, ($C_1$-$C_2$)alkoxy, carboxylic acid, amine, halo, cyano, and ($C_1$-$C_3$) ester;

$R^4$-$R^5$ are each independently selected from the group comprising hydrogen, deuterium, hydroxyl, ($C_1$-$C_2$)alkoxy, carboxylic acid, amine, halo, cyano, and ($C_1$-$C_3$) ester;

$R^7$-$R^8$ areeach independently selected from the group comprising ($C_1$-$C_3$) alkyl, hetero ($C_1$-$C_3$) alkyl, ($C_1$-$C_3$) alkenyl, hetero ($C_1$-$C_3$) alkenyl, ($C_1$-$C_3$)alkynyl, cyano, hydroxyl, halo, amine, ketal, hemiketal, and hetero ($C_1$-$C_3$) alkynyl;

$R^9$ is selected from the group comprising optionally substituted ($C_1$-$C_8$) alkyl, optionally substituted hetero ($C_1$-$C_8$) alkyl, optionally substituted ($C_1$-$C_8$)alkenyl, optionally substituted hetero($C_1$-$C_8$)alkenyl, optionally substituted ($C_1$-$C_8$) alkynyl, and optionally substituted hetero ($C_1$-$C_8$) alkynyl;

$R^{10}$-$R^{19}$ are each independently selected from the group comprising hydrogen, deuterium, FG, optionally substituted ($C_1$-$C_8$)alkyl, optionally substituted hetero($C_1$-$C_8$)alkyl, optionally substituted ($C_1$-$C_8$)alkenyl, optionally substituted hetero($C_1$-$C_8$)alkenyl, optionally substituted ($C_1$-$C_8$)alkynyl, optionally substituted hetero($C_1$-$C_8$)alkynyl, optionally substituted ($C_5$-$C_8$)cycloalkyl, optionally substituted ($C_5$-$C_8$)cycloalkenyl, optionally substituted ($C_5$-$C_8$)cycloalkynyl, optionally substituted ($C_4$-$C_8$)heterocycle, a substituted aryl, an optionally substituted aryl of two or more rings, and optionally substituted extended mixed ring system; and $R^{20}$ is selected from the group comprising a hydrogen, a deuterium, a FG, an optionally substituted ($C_5$-$C_{12}$)alkyl, an optionally substituted hetero-($C_5$-$C_{12}$)alkyl, an optionally substituted ($C_5$-$C_{12}$)alkenyl, an optionally substituted hetero-($C_5$-$C_{12}$)alkenyl, an optionally substituted ($C_5$-$C_{12}$)alkynyl, an optionally substituted hetero-($C_5$-$C_{12}$)alkynyl, an optionally substituted ($C_5$-$C_{12}$)cycloalkyl, an optionally substituted ($C_5$-$C_{12}$)cycloalkenyl, an optionally substituted ($C_5$-$C_{12}$)cycloalkynyl, an optionally substituted ($C_4$-$C_{11}$)heterocycle, a substituted aryl, an optionally substituted aryl having more than two rings, and an optionally substituted extended mixed ring system.

In a particular embodiment, the disclosure provides for a compound of Formula I or Formula II, having the structure of Formula III:

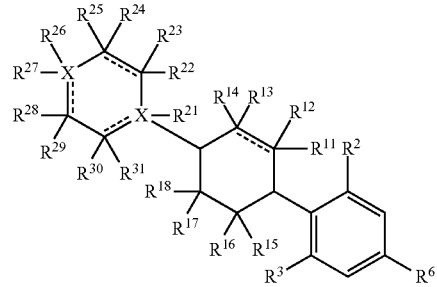

(III)

or a pharmaceutically acceptable salt, or prodrug thereof, wherein:

X is independently either a C or N;

$R^2$-$R^3$ are each independently a hydroxyl or ($C_1$-$C_2$) alkoxy;

$R^6$ is selected from the group comprising an unsubstituted ($C_4$-$C_{12}$) alkyl, an unsubstituted hetero ($C_1$-$C_{11}$) alkyl, an unsubstituted ($C_1$-$C_{12}$)alkenyl, an unsubstituted hetero($C_4$-$C_{11}$)alkenyl, an unsubstituted ($C_1$-$C_{12}$) alkynyl, and an unsubstituted hetero ($C_1$-$C_{11}$) alkynyl;

$R^{11}$-$R^{18}$ are each independently selected from the group comprising hydrogen, deuterium, FG, optionally substituted ($C_1$-$C_8$)alkyl, optionally substituted hetero($C_1$-$C_8$)alkyl, optionally substituted ($C_1$-$C_8$)alkenyl, optionally substituted hetero($C_1$-$C_8$)alkenyl, optionally substituted ($C_1$-$C_8$)alkynyl, and optionally substituted hetero ($C_1$-$C_8$) alkynyl; and $R^{21}$-$R^{31}$ are each independently selected from the group comprising hydrogen, deuterium, FG, optionally substituted ($C_1$-$C_8$)alkyl, optionally substituted hetero($C_1$-$C_8$)alkyl, optionally substituted ($C_1$-$C_8$)alkenyl, optionally substituted hetero($C_1$-$C_8$)alkenyl, optionally substituted ($C_1$-$C_8$)alkynyl, optionally substituted hetero($C_1$-$C_8$)alkynyl, optionally substituted ($C_5$-$C_8$)cycloalkyl, optionally substituted ($C_5$-$C_8$)cycloalkenyl, optionally substituted ($C_5$-$C_8$)cycloalkynyl, optionally substituted ($C_4$-$C_8$)heterocycle, optionally substituted aryl, and optionally substituted extended mixed ring system.

In a certain embodiment, the disclosure provides for a compound of Formula I or Formula II, having the structure of Formula III:

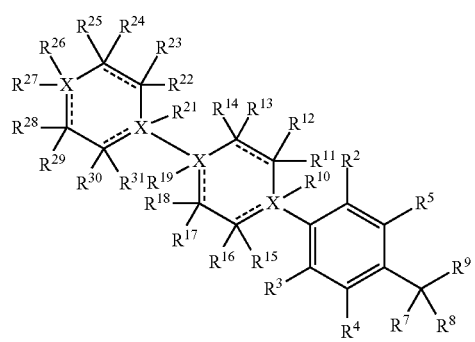

III(a)

or a pharmaceutically acceptable salt, or prodrug thereof, wherein:

X is independently either a C or N;

$R^2$-$R^3$ are each independently selected from the group comprising hydroxyl, ($C_1$-$C_2$)alkoxy, carboxylic acid, amine, halo, cyano, or ($C_1$-$C_3$)ester;

$R^4$-$R^5$ are each independently selected from the group comprising hydrogen, deuterium, hydroxyl, ($C_1$-$C_2$)alkoxy, carboxylic acid, amine, halo, cyano, and ($C_1$-$C_3$)ester;

$R^7$-$R^8$ are each independently selected from the group comprising optionally substituted ($C_1$-$C_3$)alkyl, optionally substituted hetero($C_1$-$C_3$)alkyl, optionally substituted ($C_1$-$C_3$)alkenyl, optionally substituted hetero($C_1$-$C_3$)alkenyl, optionally substituted ($C_1$-$C_3$)alkynyl, cyano, hydroxyl, halo, amine, ketal, hemiketal, and hetero ($C_1$-$C_3$) alkynyl;

$R^9$ is selected from the group comprising an optionally substituted ($C_1$-$C_8$)alkyl, an optionally substituted hetero($C_1$-$C_8$)alkyl, an optionally substituted ($C_1$-$C_8$)alkenyl, an optionally substituted hetero($C_1$-$C_8$)alkenyl, an optionally substituted ($C_1$-$C_8$)alkynyl, and an optionally substituted heteroalkynyl;

$R^{10}$-$R^{19}$ are each independently selected from the group comprising hydrogen, deuterium, FG, optionally substituted ($C_1$-$C_8$)alkyl, optionally substituted hetero($C_1$-$C_8$)alkyl, optionally substituted ($C_1$-$C_8$)alkenyl, optionally substituted hetero($C_1$-$C_8$)alkenyl, optionally substituted ($C_1$-$C_8$)alkynyl, optionally substituted hetero($C_1$-$C_8$)alkynyl, optionally substituted ($C_5$-$C_8$)cycloalkyl, optionally substituted ($C_5$-$C_8$)cycloalkenyl, optionally substituted ($C_5$-$C_8$)cycloalkynyl, optionally substituted ($C_4$-$C_8$)heterocycle, optionally substituted aryl, and optionally substituted extended mixed ring system; and $R^{21}$-$R^{31}$ are each independently selected from the group comprising hydrogen, deuterium, FG, optionally substituted ($C_1$-$C_8$)alkyl, optionally substituted hetero($C_1$-$C_8$)alkyl, optionally substituted ($C_1$-$C_8$)alkenyl, optionally substituted hetero($C_1$-$C_8$)alkenyl, optionally substituted ($C_1$-$C_8$)alkynyl, optionally substituted hetero($C_1$-$C_8$)alkynyl, optionally substituted ($C_5$-$C_8$)cycloalkyl, optionally substituted ($C_5$-$C_8$)cycloalkenyl, optionally substituted ($C_5$-$C_8$)cycloalkynyl, optionally substituted ($C_4$-$C_8$)heterocycle, optionally substituted aryl, and optionally substituted extended mixed ring system.

In a particular embodiment, the disclosure provides for a compound of Formula I, II or III, wherein $R^6$ is selected from the group comprising methyl, ethyl, n-propyl, n-butyl, n-pentyl, n-hexyl, n-heptyl, isopropyl, sec-butyl, (1-methyl)butyl, (1-methyl)pentyl, (1-methyl)hexyl, (1-methyl)heptyl, (1,1-dimethyl)propyl, (1,1-dimethyl)butyl, (1,1-dimethyl)pentyl, (1,1-dimethyl)hexyl, (1,1-dimethyl)heptyl, (1,2-dimethyl) propyl, (1,2-dimethyl)butyl, (1,2-dimethyl)pentyl, (1,2-dimethyl)hexyl, (1,2-dimethyl)heptyl, (1,3-dimethyl)butyl, (1,3-dimethyl)pentyl, (1,3-dimethyl)hexyl, (1,3-dimethyl)heptyl, (1,4-dimethyl)pentyl, (1,4-dimethyl)hexyl, (1,4-dimethyl) heptyl, (1,5-dimethyl)hexyl, (1,5-dimethyl)heptyl, (1,6-dimethyl)heptyl, (1,2-diethyl)butyl, (1,2-diethyl)pentyl, (1,2-diethyl)hexyl, (1,2-diethyl)heptyl, (1,2-diethyl)pentyl, (1,3-diethyl)pentyl, (1,3-diethyl)hexyl, (1,3-diethyl)heptyl, (1,4-diethyl)pentyl, (1,4-diethyl)hexyl, (1,4-diethyl)heptyl, (1,5-diethyl)hexyl, (1,5-diethyl)heptyl, (1,6-diethyl)heptyl, (1,2,3-trimethyl)butyl, (1,1,2-trimethyl)butyl, (1,1,3-trimethyl) butyl, (1,2,3-trimethyl)pentyl, (1,1,2-trimethyl)pentyl, (1,1,3-trimethyl)pentyl, (1,2,4-trimethyl)pentyl, (1,3,4-trimethyl)pentyl, (1,1,4-trimethyl)pentyl, (1,2,3-trimethyl)hexyl, (1,1,2-trimethyl)hexyl, (1,1,3-trimethyl)hexyl, (1,2,4-trimethyl) hexyl, (1,2,5-trimethyl)hexyl, (1,1,4-trimethyl)hexyl, (2,3,4-trimethyl)hexyl, (2,3,5-trimethyl)hexyl, (1,1,5-trimethyl) hexyl, (1,2,3-trimethyl)heptyl, (1,1,2-trimethyl)heptyl, (1,1,3-trimethyl)heptyl, (1,2,4-trimethyl)heptyl, (1,1,5-trimethyl)heptyl, (1,1,6-trimethyl)heptyl, (1,2,5-trimethyl)heptyl, (1,2,6-trimethyl)heptyl, (2,3,4-trimethyl)heptyl, (2,3,5-trimethyl)heptyl, (2,3,6-trimethyl)heptyl, (2,4,5-trimethyl)heptyl, (2,4,6-trimethyl)heptyl, (3,4,5-trimethyl)heptyl, (3,4,6-trimethyl) heptyl, and (4,5,6-trimethyl)heptyl.

In another embodiment, the disclosure provides for a compound of Formula I, II, II(a), III, or III(a), selected from the group comprising:

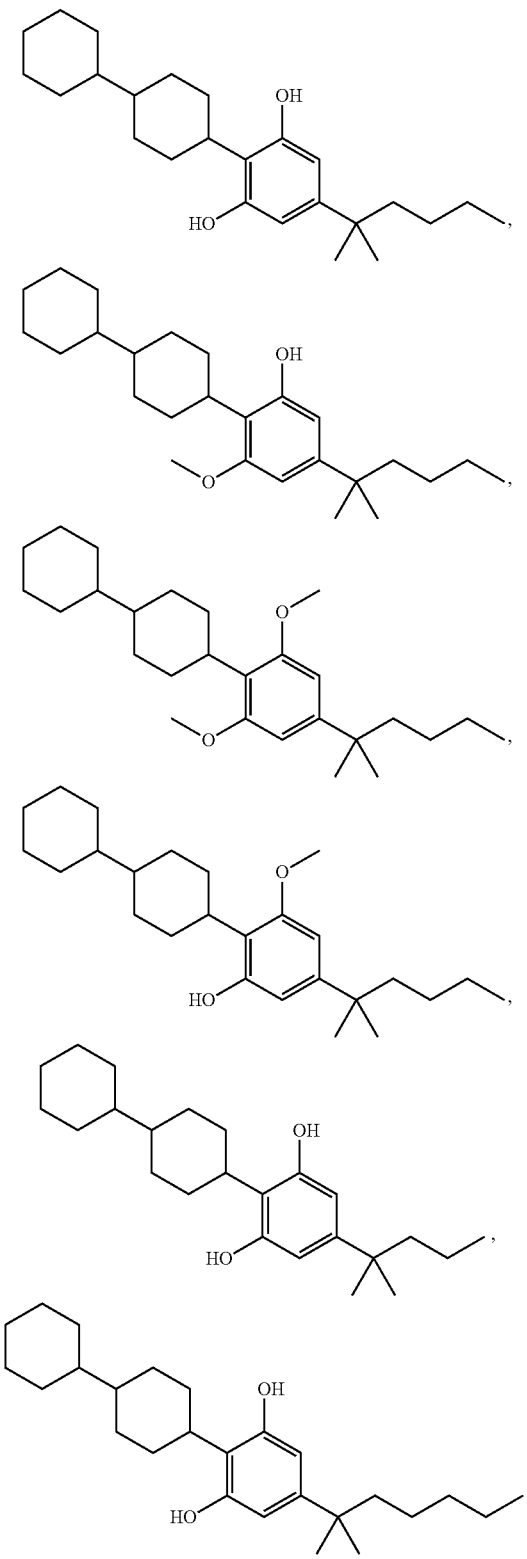

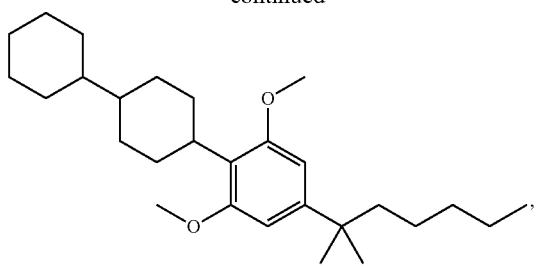

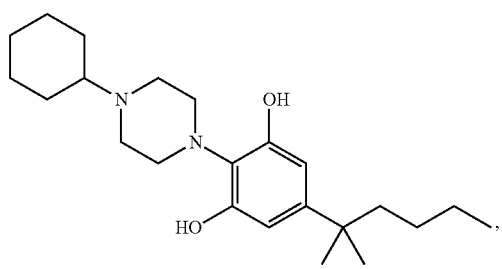 [SMILES: CCCCC(C)(C)c1cc(O)c(C2CCC(C3CCCCC3)CC2)c(O)c1]

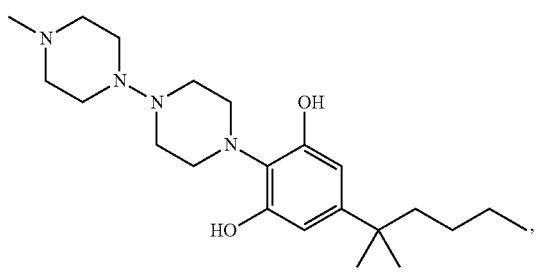

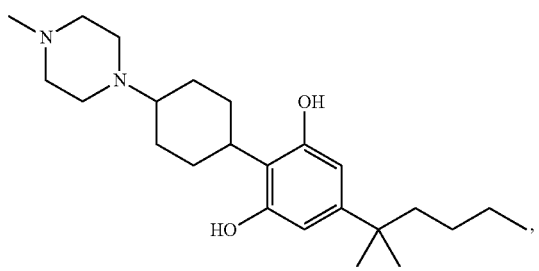

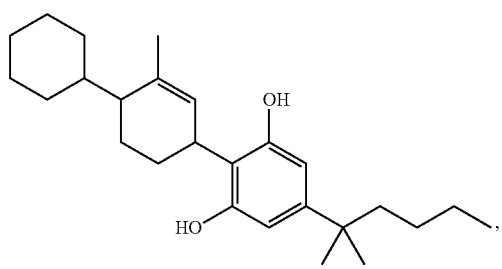

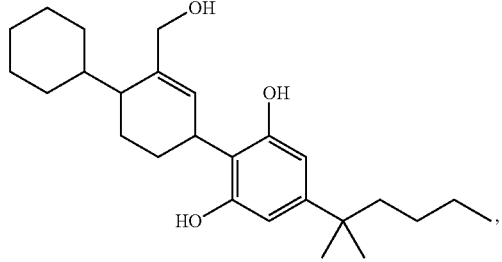

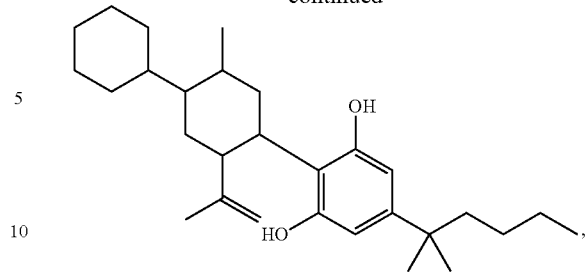

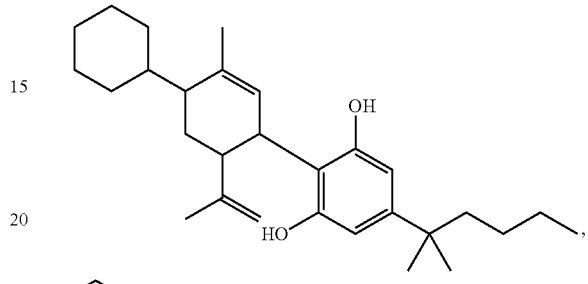

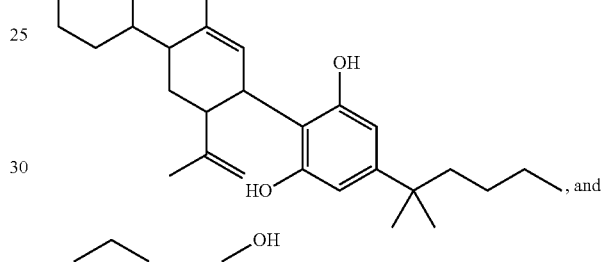

, and

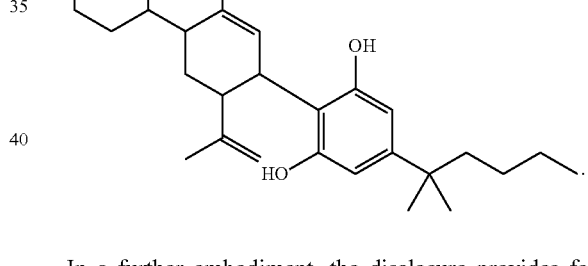

In a further embodiment, the disclosure provides for a compound of Formula I, II, II(a), III, or III(a), having the structure of:

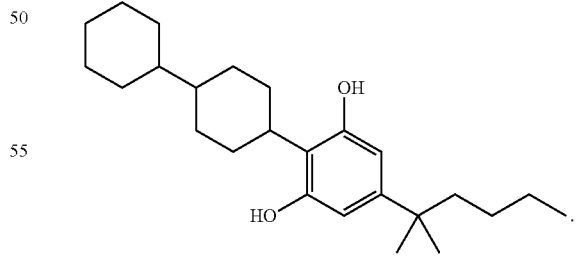

The compounds disclosed herein can be prepared by methods known to one of skill in the art and routine modifications thereof, and/or following procedures and schemes presented herein, and routine modifications thereof, and/or procedures found in international application PCT/US2002/19569, Mahadevan et al., *J. Med. Chem.* 2000, 43(2):3778-86; Ben-Shabat et al., *J. Med. Chem.* 2006, 49(3):1113-117; Wiley et al., JPET 2002, 301(2):679-689; Thompson et al., *Synthesis* 2005 4:547-550; Razdan, Rajik, *The total synthesis of natural products* 4, 1981:186-262, and references cited therein and routine modifications thereof.

In a particular embodiment, Scheme I or modifications thereof can be used to make one or more compounds of the disclosure.

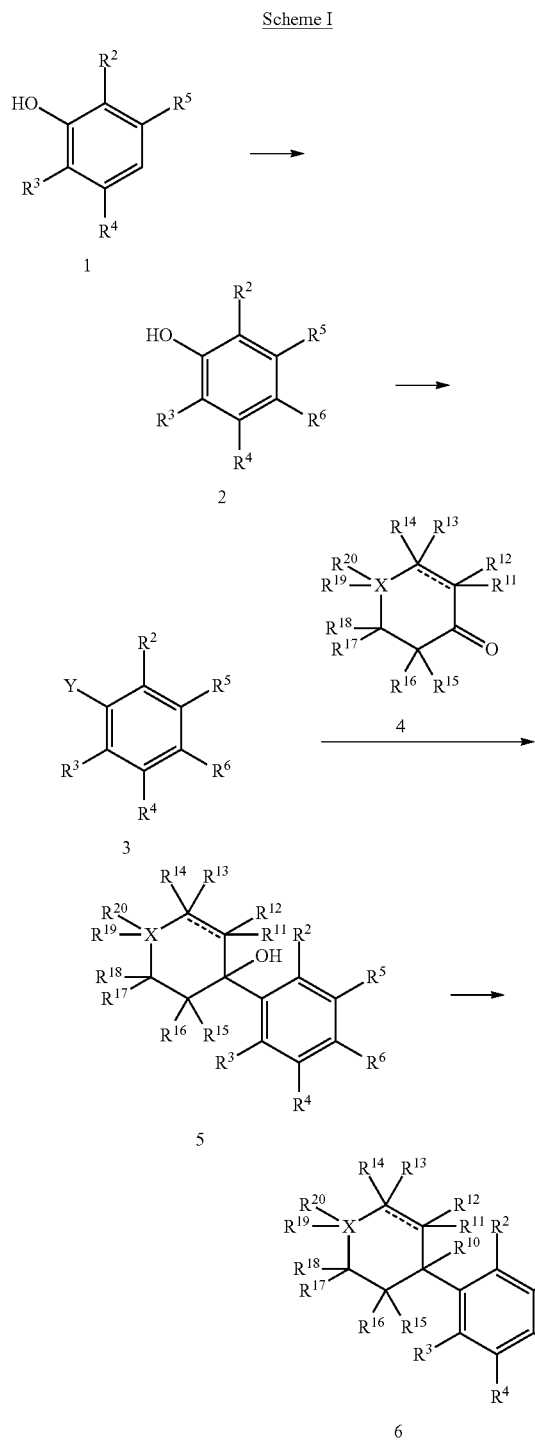

Phenol 1 is reacted with a carbocation comprising $R^6$, formed by reacting an alkyl, heteroalkyl, an alkenyl, a hetero-alkenyl, an alkynyl, or a heteroalkynyl containing a terminal tertiary hydroxyl group in the presence of a strong acid, such as methanesulfonic acid, at an elevated temperature to afford compound 2. Compound 2 is reacted with bis(pinacolato)diboron in the presence of a palladium catalyst, at an elevated temperature in an appropriate solvent system, such as a mixture of N,N-diethylethanamine and dioxane, to form a boronate ester intermediate, which is then reacted with a copper (I)halide, such as copper(I)bromide, in an appropriate solvent system, such as a mixture of methanol and water, at an elevated temperature to form aryl halide 3 (wherein Y is I, Br or Cl). Aryl halide 3 is then transmetallated by adding magnesium turnings in ether to form a Grignard reagent, which is then reacted with ketone 4 to afford compound 5. Compound 5 can then be reacted with any number regents to convert, substitute, or eliminate the hydroxyl group to give compound 6.

In a certain embodiment, Scheme II or modifications thereof can be used to make one or more compounds of the disclosure.

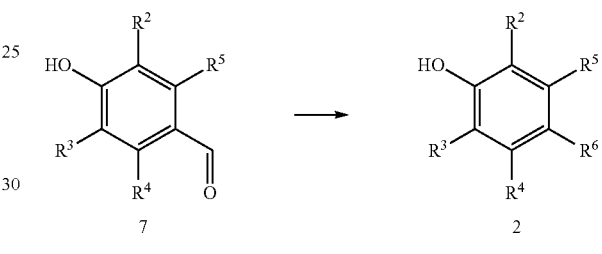

Benzaldehyde 7 is reacted with a Wittig reagent comprising $R^6$. The resulting alkene can be selectively reduced by using mild reducing agents to afford compound 2.

In another embodiment, Scheme III or modifications thereof can be used to make one or more compounds of the disclosure.

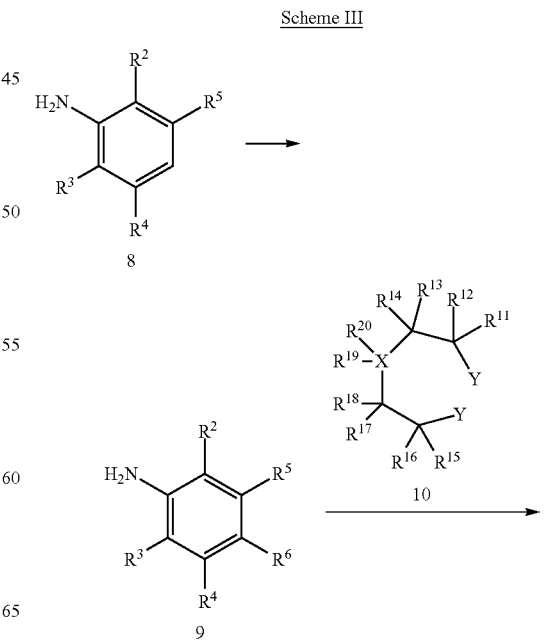

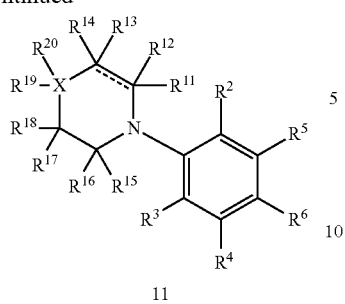

11

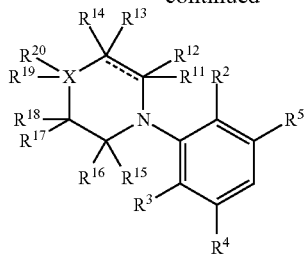

13

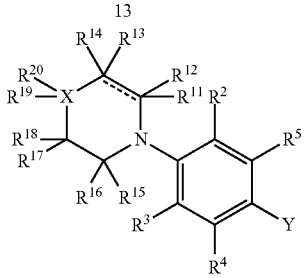

14

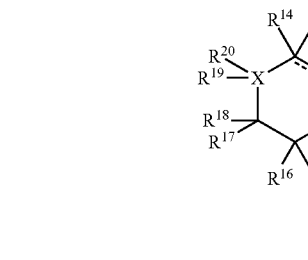

15

Aniline 8 is reacted with a carbocation comprising $R^6$, formed by reacting an alkyl, heteroalkyl, an alkenyl, an hetero-alkenyl, an alkynyl, or an heteroalkynyl containing a terminal tertiary hydroxyl group in the presence of a strong acid, such as methanesulfonic acid, at an elevated temperature to afford compound 9. Compound 9 is reacted with compound 10 (wherein Y is a halide or good leaving group) in the presence of a base, such as anhydrous potassium carbonate, in an appropriate solvent, such as diglyme, at an elevated temperature to afford compound 11.

In yet another embodiment, Scheme IV or modifications thereof can be used to make one or more compounds of the disclosure.

Scheme IV

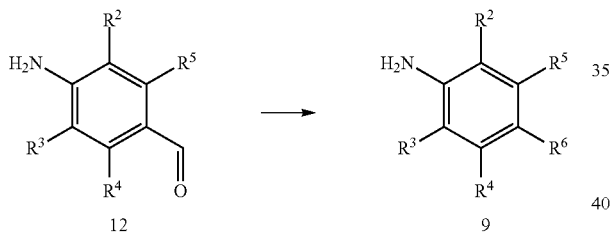

12       9

Benzaldehyde 12 is reacted with a Wittig reagent comprising $R^6$. The resulting alkene can be selectively reduced by using mild reducing agents to afford compound 9.

In a particular embodiment, Scheme V or modifications thereof can be used to make one or more compounds of the disclosure.

Scheme V

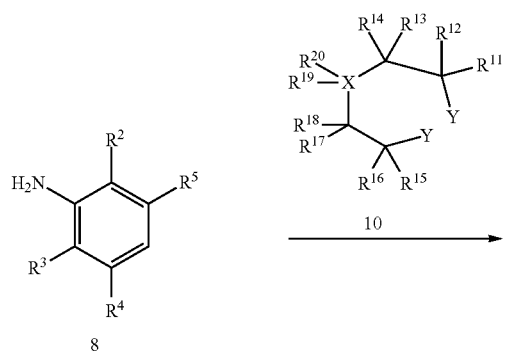

8

Compound 8 is reacted with compound 10 (wherein Y is a halide or good leaving group) in the presence of a base, such as anhydrous potassium carbonate, in an appropriate solvent, such as diglyme, at an elevated temperature to afford compound 13. Compound 13 is reacted with a halide, such as elemental bromine, in an appropriate acid, such as hydrobromic, hydroiodic, or hydrochloric acid, in an appropriate acid based solvent, such as glacial acetic acid, to afford compound 14 (wherein Y is a halide). Compound 14 is reacted with magnesium turnings to form a Grignard reagent, which is then reacted with an alkyl, heteroalkyl, an alkenyl, a heteroalkenyl, an alkynyl, or a heteroalkynyl containing an aldehyde group, which can then subsequently converted into a good leaving group and substituted with a hydride from a hydride donor, such as sodium cyanoborohydride.

It should be understood many of the reagents and starting materials used in the Schemes presented herein are readily available from various commercial suppliers, such as Sigma-Aldrich, Alfa Aesar, Tokyo Chemical Industry Co., LTD, etc. Moreover, many of these same reagents and starting materials can be modified to incorporate additional functional groups by using standard organic synthesis reactions.

When a compound disclosed herein contains an acidic or basic moiety, it may also disclosed as a pharmaceutically acceptable salt (See, Berge et al., J. Pharm. Sci. 1977, 66, 1-19; and "Handbook of Pharmaceutical Salts, Properties, and Use," Stah and Wermuth, Ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, hydroiodic acid, (+)-L-lactic acid, (+/−)-DL-lactic acid, lactobionic acid, lauric acid, maleic acid, (−)-L-malic acid, malonic acid, (+/−)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The disclosure provides that compounds disclosed herein can have prodrug forms. Prodrugs of the compounds are useful in the methods of this disclosure. Any compound that will be converted in vivo to provide a biologically, pharmaceutically or therapeutically active form of a compound of the disclosure is a prodrug. Various examples and forms of prodrugs are well known in the art. Examples of prodrugs are found, inter alia, in *Design of Prodrugs*, edited by H. Bundgaard, (Elsevier, 1985), Methods in Enzymology, Vol. 42, at pp. 309-396, edited by K. Widder, et al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392).

Prodrugs of compounds disclosed herein can be prepared by methods known to one of skill in the art and routine modifications thereof, and/or procedures found in U.S. Pat. No. 8,293,786, and references cited therein and routine modifications made thereof.

In a certain embodiment, the disclosure provides for prodrug forms of a compound disclosed herein having a structure selected from the group comprising:

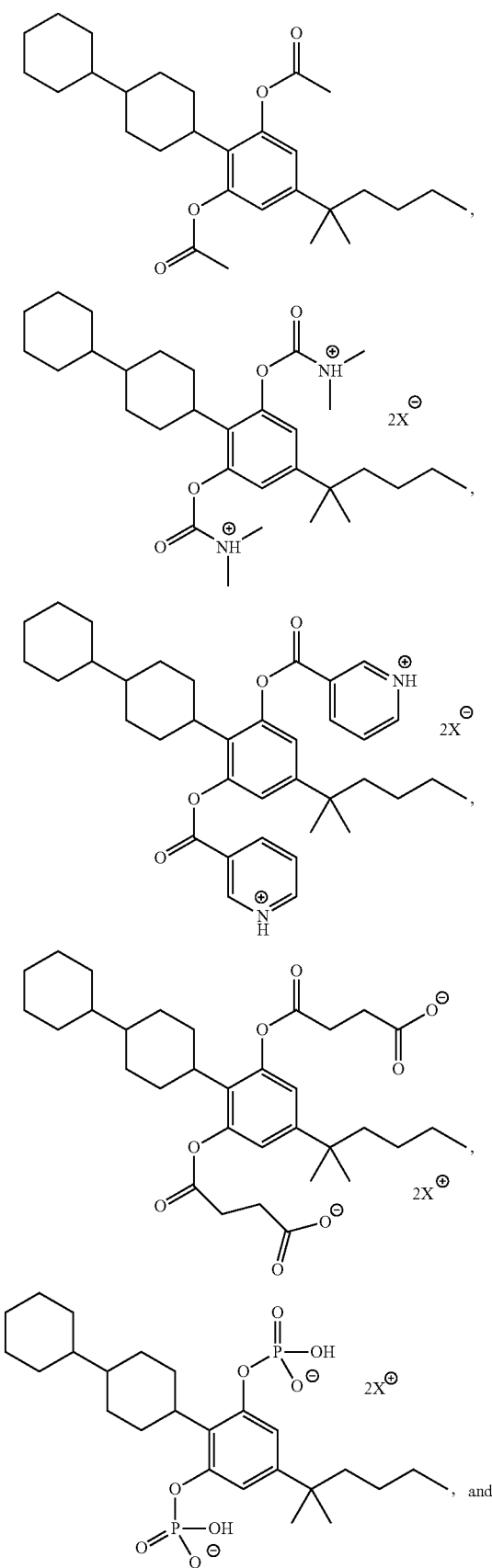

-continued

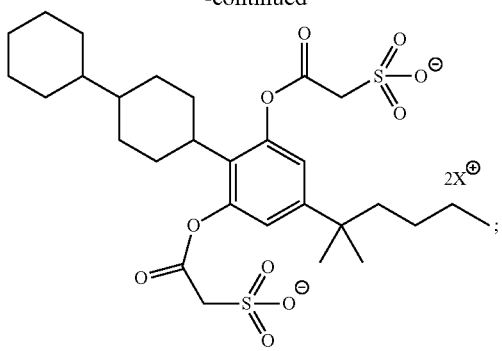

wherein, X is a pharmaceutically acceptable counter ion.

The disclosure also provides methods for identifying a library of Id modulators comprising screening compounds of Formula I, II, II(a), III, or III(a) in assays. High throughput screening methodologies are particularly envisioned for the detection of modulators of expression of a target Id helix-loop-helix polypeptides, such as Id-1, using methods already described herein. Such high throughput screening methods typically involve providing a combinatorial chemical or peptide library containing a large number of potential therapeutic compounds (e.g., modulator compounds). Such combinatorial chemical libraries or ligand libraries are then screened in one or more assays to identify those library members (e.g., particular chemical species or subclasses) that display a desired characteristic activity. The compounds so identified can serve as conventional lead compounds and/or used as potential or actual therapeutics. For administration to a subject, modulators of Id helix-loop-helix expression and/or activity (e.g., inhibitory agents, nucleic acid molecules, proteins, or compounds identified as modulators of Id expression and/or activity) will preferably be incorporated into pharmaceutical compositions suitable for administration.

A combinatorial chemical library is a collection of diverse chemical compounds generated either by chemical synthesis or biological synthesis, by combining a number of chemical building blocks (e.g., reagents such as amino acids). As an example, a linear combinatorial library, e.g., a polypeptide or peptide library is formed by combining a set of chemical building blocks in every possible way for a given compound length (e.g., the number of amino acids in a polypeptide or peptide compound). Millions of chemical compounds can be synthesized through such combinatorial mixing of chemical building blocks.

The preparation and screening of combinatorial chemical libraries is well known to those having skill in the pertinent art. Combinatorial libraries include, without limitation, peptide libraries (e.g., U.S. Pat. No. 5,010,175; Furka, 1991, Int. J. Pept. Prot. Res., 37:487-493; and Houghton et al., 1991, Nature, 354:84-88). Other chemistries for generating chemical diversity libraries can also be used. Nonlimiting examples of chemical diversity library chemistries include peptoids (PCT Publication No. WO 91/019735), encoded peptides (PCT Publication No. WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., 1993, Proc. Natl. Acad. Sci. USA, 90:6909-6913), vinylogous polypeptides (Hagihara et al., 1992, J. Amer. Chem. Soc., 114:6568), non-peptidal peptidomimetics with glucose scaffolding (Hirschmann et al., 1992, J. Amer. Chem. Soc., 114:9217-9218), analogous organic synthesis of small compound libraries (Chen et al., 1994, J. Amer. Chem. Soc., 116:2661), oligocarbamates (Cho et al., 1993, Science, 261:1303), and/or peptidyl phosphonates (Campbell et al., 1994, J. Org. Chem., 59:658), nucleic acid libraries (see Ausubel, Berger and Sambrook, all supra), peptide nucleic acid libraries (U.S. Pat. No. 5,539,083), antibody libraries (e.g., Vaughn et al., 1996, Nature Biotechnology, 14(3):309-314) and PCT/US96/10287), carbohydrate libraries (e.g., Liang et al., 1996, Science, 274-1520-1522) and U.S. Pat. No. 5,593,853), small organic molecule libraries (e.g., benzodiazepines, Baum C&EN, Jan. 18, 1993, page 33; and U.S. Pat. No. 5,288,514; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and the like).

In a certain embodiment, a compound disclosed herein can be administered directly or as a part of a composition. In other embodiments, the composition could be formulated as a pharmaceutical composition for administration to a subject. In another embodiment, a compound disclosed herein can be a part of a pharmaceutical composition which includes one or more pharmaceutically acceptable carriers. Pharmaceutically acceptable carriers include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the disclosure is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy to administer by a syringe. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound, e.g. a compound disclosed herein, in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

In a particular embodiment, one or more compounds of the disclosure are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations should be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the disclosure, the therapeutically effective dose can be estimated initially from cell culture assays. A dose can be formulated in animal models to achieve a circulating plasma concentration range that includes the $IC_{50}$ (e.g., the concentration of the test compound which achieves a half-maximal inhibition of symptoms) as determined in cell culture. Such information can be used to more accurately determine useful doses in humans. Levels in plasma can be measured, for example, by high performance liquid chromatography.

Compositions and formulations of one or more compounds disclosed herein can be used in combination with THC or a THC derivative to treat a disorder or disease in a subject. Examples of such disorders or diseases which can be treated include cancer and other cell proliferative disorders, such as chronic pancreatitis, psoriasis, neoplasms, angiomas, endometriosis, obesity, age-related macular degeneration, retinopathies, restenosis, scaring, fibrogenesis, fibrosis, cardiac remodeling, pulmonary fibrosis, scleroderma, and failures resulting from myocardial infarction, keloids, fibroid tumors and stenting.

Moreover, a compound disclosed herein can have one or more biological effects including, but not limited to, inducing apoptosis in malignant cells, inhibiting the proliferation of cancer cells, increasing the effectiveness of chemotherapeutic agents, regulating transcriptional activity, reducing inflammation, increasing cellular differentiation, modulating ETS domain transcription factors, modulating PAX transcription factors, modulating TCF-ETS domain transcription factors, down regulating RAF-1/MAPK, upregulating JNK signaling pathways, and modulating cellular transformation. In a certain embodiment, the disclosure provides for a composition comprising a compound disclosed herein that can be used to treat a disease or disorder which is ameliorated by modulating ETS domain transcription factors, modulating PAX transcription factors, modulating TCF-ETS domain transcription factors, down regulating RAF-1/MAPK, and/or upregulating JNK signaling pathways.

In another embodiment, a method of treating cancer in a subject comprises administering to a subject in need of such treatment a therapeutically effective amount of a pharmaceutical composition consisting essentially of one or more compounds disclosed herein and a pharmaceutically acceptable carrier.

In general, provided herein are methods for treating cancer by administering to a subject a therapeutically effective amount of a composition consisting essentially of a combination of one or more compounds disclosed herein and THC or a derivative of THC. Examples of THC derivatives, includes, but are not limited to: $\Delta^9$-tetrahydrocannabinol-$C_4$, $\Delta^9$-tetrahydrocannabivarin, tetrahydrocannabiorcol, $\Delta^9$-tetrahydro-cannabinolic acid A, $\Delta^9$-tetrahydro-cannabinolic acid B, $\Delta^9$-tetrahydro-cannabinolic acid-$C_4$ A, $\Delta^9$-tetrahydro-cannabinolic acid-$C_4$ B, $\Delta^9$-tetrahydro-cannabivarinic acid A, $\Delta^9$-tetrahydro-cannabiorcolic acid A, $\Delta^9$-tetrahydro-cannabiorcolic acid B, $(-)$-$\Delta^8$-trans-(6aR,10aR)-$\Delta^8$-tetrahydrocannabinol, $(-)$-$\Delta^8$-trans-(6aR,10aR)-tetrahydrocannabinolic acid A, and $(-)$-(6aS,10aR)-$\Delta^9$-tetrahydrocannabinol. The methods include using a pharmaceutical composition that includes a combination of one or more compounds disclosed herein and THC or a THC derivative.

The compounds described herein and compositions comprising the compounds are useful in modulating the expression and/or activity of Id polypeptides in proliferating cells. In one exemplary embodiment, the disclosure demonstrates a role for the compounds disclosed herein, in inhibiting the metastasis through inhibition of Id-1 expression and/or activity. In a further embodiment, the disclosure demonstrates a role for the compounds disclosed herein, in inhibiting cell proliferation by activating $CB_2$ receptors.

Accordingly, the compounds disclosed herein can be used in methods for modulating metastatic cancer cell progression by regulating the expression and/or activity of an Id polypeptide. The methods include using a pharmaceutical composition that includes an agent that modulates the expression and/or activity of an Id polypeptide. Exemplary agents include cannabinoids and derivatives arising there from, such as cannabidiol and derivatives therefrom.

U.S. patent application Ser. No. 11/390,682, and International application No. PCT/US01/2881, are hereby incorporated by reference, in their entirety for all purposes. While these publications provide general information about Id-1, it is understood that they do not propose or describe the methods provided herein.

In a certain embodiment, the compounds disclosed herein can be used alone or in combination with one or more additional therapeutic agents, such as THC. In a further embodiment, the compound disclosed herein can be used in combination with THC or a derivative thereof in a defined ratio based on weight. For example, in a certain embodiment, a compound disclosed herein can be combined with THC or a derivative thereof, so that the ratio of a compound disclosed herein to THC or a derivative thereof (wt/wt) is from 1:99, 10:90, 20:80, 30:70, 40:60, 50:50, 60:40, 70:30, 80:20, 90:10, 99:1, or any ratio in-between.

In a particular embodiment, the disclosure provides a composition for treating cancer in a subject, the composition comprising a compound disclosed herein and THC or a derivative thereof, such as tetrahydrocannabivarin (THCV). In another embodiment, the disclosure provides a method for treating a disease or disorder in a subject, such as cancer, comprising administering to a subject in need of such treatment a therapeutically effective amount of a compound disclosed herein and THC or a THC derivative.

In another embodiment, a compound disclosed herein can be used to treat a disease or disorder that would be benefited by modulating the activity of serotonin receptors, also known as 5-hydroxytryptamine receptors or 5-HT receptors. In yet a further embodiment, a compound disclosed herein can be used to treat a disease or disorder that would be benefited by activating 5-HT receptors. In another embodiment, a compound disclosed herein can be used as an antidepressant, anxiolytic, or neuroprotective agent. In yet a further embodiment, a compound disclosed herein, can be used to relieve convulsion, inflammation, anxiety, and nausea.

In a certain embodiment, a compound disclosed herein can be used alone or combined with THC or a derivative thereof to treat a neurodegenerative disease or disorder, including, but not limited to, Alzheimer's Disease, Parkinson's Disease, age related dementia, Huntington's Disease, and amyotrophic lateral sclerosis. In another embodiment, a compound disclosed herein can be used alone or combined with THC or a derivative thereof to treat pain or pain associated with a disease or disorder, including, but not limited to, pain associated with cancer, pain associated with arthritis, headaches, post-operative pain, fibromyalgia, and undiagnosed pain.

In another embodiment, a compound disclosed herein can be combined with one or more therapeutic agents that have one or more of the following biological effects, including, but not limited to, inducing apoptosis, regulating transcription, enhancing chemotherapy, reducing inflammation, promoting cellular differentiation, modulating cellular transformation, modulating cell migration, and/or inhibiting metastasis.

It should be understood that the administration of an additional therapeutic agent with a compound of the disclosure encompasses co-administration of these therapeutic agents in a substantially simultaneous manner, such as in a single capsule having a fixed ratio of active ingredients or in multiple, separate capsules for each active ingredient. In addition, administration of an additional therapeutic agent in combination with a compound disclosed herein also encompasses use of each type of therapeutic agent in a sequential manner. In either case, the treatment regimen will provide beneficial effects of the drug combination in treating the disorders described herein.

In a further embodiment, the compounds disclosed herein can be combined with one or more class of therapeutic agents, including, but not limited to, alkylating agents, cancer immunotherapy monoclonal antibodies, anti-metabolites, mitotic inhibitors, anti-tumor antibiotics, topoisomerase inhibitors, photosensitizers, tyrosine kinase inhibitors, anti-cancer agents, chemotherapeutic agents, anti-migraine treatments, anti-tussives, mucolytics, decongestants, anti-allergic non-steroidals, expectorants, anti-histamine treatments, anti-retroviral agents, CYP3A inhibitors, CYP3A inducers, protease inhibitors, adrenergic agonists, anti-cholinergics, mast cell stabilizers, xanthines, leukotriene antagonists, glucocorticoid treatments, antibacterial agents, antifungal agents, sepsis treatments, steroidals, local or general anesthetics, NSAIDS, NRIs, DARIs, SNRIs, sedatives, NDRIs, SNDRIs, monoamine oxidase inhibitors, hypothalamic phoshpholipids, anti-emetics, ECE inhibitors, opioids, thromboxane receptor antagonists, potassium channel openers, thrombin inhibitors, growth factor inhibitors, anti-platelet agents, P2Y(AC) antagonists, anti-coagulants, low molecular weight heparins, Factor VIa inhibitors, Factor Xa inhibitors, renin inhibitors, NEP inhibitors, vasopepsidase inhibitors, squalene synthetase inhibitors, anti-atherosclerotic agents, MTP inhibitors, calcium channel blockers, potassium channel activators, alpha-muscarinic agents, beta-muscarinic agents, anti-arrhythmic agents, diuretics, thrombolytic agents, anti-diabetic agents, mineralocorticoid receptor antagonists, growth hormone secretagogues, aP2 inhibitors, phophodiesterase inhibitors, anti-inflammatories, anti-proliferatives, antibiotics, farnesyl-protein transferase inhibitors, hormonal agents, plant-derived products, epipodophyllotoxins, taxanes, prenyl-protein transferase inhibitors, anti-TNF antibodies and soluble TNF receptors, Cyclooxygenase-2 inhibitors, and miscellaneous agents.

In yet a further embodiment, a compound disclosed herein can be combined with one or more classes of therapeutic agents, including, but not limited to, alkylating agents, cancer immunotherapy monoclonal antibodies, anti-metabolites, mitotic inhibitors, anti-tumor antibiotics, topoisomerase inhibitors, photosensitizers, tyrosine kinase inhibitors, anti-cancer agents, and chemotherapeutic agents.

In yet another embodiment, the additional therapeutic agent is an anti-cancer agent. Examples of anti-cancer agents include, but are not limited to, methotrexate, fluorouracil, hydroxyurea, mercaptopurine, cisplatin, daunorubicin, doxorubicin, etoposide, vinblastine, vincristine, temozolomide, and pacitaxel.

In a particular embodiment, a pharmaceutical composition for treating a cell proliferative disorder includes a compound disclosed herein and one or more therapeutic agents selected from the group comprising: THC, paclitaxel, temozolomide, methotrexate, fluorouracil, hydroxyurea, mercaptopurine, cisplatin, daunorubicin, doxorubicin, etoposide, vinblastine, vincristine and pacitaxel.

For use in the therapeutic applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers can be formed from a variety of materials such as glass or plastic.

For example, the container(s) can comprise one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprise a compound with an identifying description or label or instructions relating to its use in the methods described herein.

A kit will typically comprise one or more additional containers, each with one or more of various materials (such as reagents, optionally in concentrated form, and/or devices) desirable from a commercial and user standpoint for use of a compound described herein. Non-limiting examples of such materials include, but are not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself, a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein. These other therapeutic agents may be used, for example, in the amounts indicated in the Physicians' Desk Reference (PDR) or as otherwise determined by one of ordinary skill in the art.

EXAMPLES

Cell culture and treatment of breast cancer cell lines: Human breast cancer cells lines MDA-MB231 and MDA-MB436 were obtained from the ATCC. To prepare the MDA-MB231-Id-1 cells, cells were infected with a pLXSN-Id-1 sense expression vector. In all experiments, the different cell populations were first cultured in RPMI media containing 10% fetal bovine serum ("FBS"). On the first day of treatment the media was replaced with vehicle control or drug in RPMI and 0.1% FBS. The media with the appropriate compounds were replaced every 24 h. $\Delta^9$-THC, CBN, CBD, CBG, and CP55, 940 were obtained from NIH through the National Institute of Drug Abuse. WIN 55, 212-2 was purchased from Sigma/RBI (St. Louis, Mo.).

Cell culture and treatment of gbm cell lines: The human GBM cell lines used were SF126, U87 and U251. Cell lines were maintained at 37° C. and 5% $CO_2$. In all experiments, the different cell populations were first cultured in RPMI media containing 10% FBS. On the first day of treatment the media was replaced with vehicle control or drug in RPMI and 0.1% FBS. The media with the appropriate compounds were replaced every 24 h. $\Delta^9$-THC, CBN, CBD, CBG, and CP55, 940 were obtained from NIH through the National Institute of Drug Abuse. WIN55, 212-2 was purchased from Sigma/RBI (St. Louis, Mo.).

MTT assay: To quantify cell proliferation, the 3-[4,5-dimethylthiazol-2-yl]-2,5-diphenyl tetrasodium bromide MTT assay was used (Chemicon, Temecula, Calif.). Cells were seeded in 96 well plates at $1 \times 10^3$ cells/well for seven day experiments and $3 \times 10^3$ cells per $cm^2$ for three day experiments to obtain optimal cell density throughout the experiment. Upon completion of the drug treatments, cells were incubated at 37° C. with MTT for four hours, and then isopropanol with 0.04N HCl was added and the absorbance was read after one hour in a plate reader with a test wavelength of 570 nm. The absorbance of the media alone at 570 nm was subtracted, and percent control was calculated as the absorbance of the treated cells/control cells×100.

Statistical analysis: The $IC_{50}$ values with corresponding 95% confidence limits were compared by analysis of logged data (GraphPad Prism, San Diego, Calif.). When just the confidence limits of the $IC_{50}$ values overlapped significant differences were determined using unpaired Student's t-test. Where suitable, significant differences were also determined (Prism) using ANOVA or the unpaired Student's t-test. Bonferroni-Dunn post-hoc analyses were conducted when appropriate. p values <0.05 defined statistical significance.

Apoptosis: Cells were grown in 6 well culture dishes and were treated with compounds of the disclosure every 24 hours for three days. The cells were trypsinized, washed with PBS, and processed for labeling with fluorescein-tagged UTP nucleotide and PI by use of an Apo-Direct apoptosis kit obtained from Phoenix Flow Systems (San Diego, Calif.) and was used according to the manufacturer's protocol. The labeled cells were analyzed by flow cytometry. Cell Flow Cytometry in combination with PI and annexin staining was used to quantify the percentage of cells undergoing apoptosis in control and treatment groups. Percent control was calculated as annexin positive staining in treated cells/control cells×100. PI staining was used to distinguish necrotic cells from those undergoing apoptosis.

Quantitative western analysis: Cells were cultured and treated in 6-well dishes. After the cells were washed twice with cold PBS, lysis buffer was added. The cells were then lysed by freezing for 10 min at −70° C. and then thawing at ambient temperature. The cell lysate was collected and the protein content was determined by using Bradford reagent. Equal amounts of protein were heated at 90° C. in Laemmli sample buffer which also included β-mercaptoethanol. The samples were then loaded onto a precast SDS-PAGE gel (Bio-Rad Laboratories, Hercules, Calif.). After which, proteins were then electroblotted onto an Immobilon membrane (Millipore, Billerica, Mass.) overnight at 2-4° C. The membrane was then blocked for 1 hour with 5% nonfat dry milk which included TBS+Tween. The membranes were then incubated with 1 mcg/mL of primary antibody (rabbit anti-phospho-JNK, rabbit anti-phospho-p38, rabbit anti-phospho-ERK1/2 or rabbit anti-ERK1/2; the antibodies were from Millipore) for 1 hour in blocking buffer. The blots were then washed three times with TBS+Tween for 10 min per wash. Secondary antibody (Donkey Anti-Rabbit IgG, from Jackson Immunoresearch, West Grove, Pa.) was then added. Alternatively, the primary antibody was anti-Id-1 and an appropriate secondary antibody was used. Blots were incubated for 45 min and then washed 4 times with TBS+Tween for 15 min each. The blots were developed with SuperSignal Femto (Pierce, Rockford, Ill.), and imaged on either a Fluorchem 8900 (Alpha Innotech, San Leandro, Calif.) or ECL Hyperfilm (Amersham-Pharmacia, Piscataway, N.J.). Band intensity values were obtained (after background subtraction) directly from the Fluorchem 800 using AlphaeaseFC software (San Leandro, Calif.) or from film using Image-J (NIH, MD). As a normalization control for loading, blots were stripped and re-probed with mouse alpha-tubulin (Abcam, Cambridge, Mass.) and goat anti-mouse IgG (Jackson Immunoresearch) for the primary and secondary antibodies, respectively.

Cell cycle analysis: U251 cells were grown in Petri dishes (100 mm×15 mm) and received drug treatments for 2 days. On the third day, the cells were harvested and centrifuged at 1200 rpm for 5 minutes. The pellet was washed 1× with PBS+1% BSA, and centrifuged again. The pellet was re-suspended in 0.5 ml of 2% paraformaldehyde (diluted with PBS) and left to fix overnight at room temperature. The next day the cells were pelleted and re-suspended in 0.5 ml 0.3% Triton in PBS and incubated for 5 minutes at room temperature. The cells were then washed 2 times with PBS+1% BSA. The cells were finally suspended in PBS (0.1% BSA) with 10 ug/ml Propidium Iodide and 100 μg/ml RNAse. The cells were incubated for 30 minutes at room temperature before being stored at 4° C. Cell cycle was measured using a FACS Calibur using Cell Quest Pro and Modfit software.

Radical oxygen species (ROS) measurements: The production of cellular radical oxygen species (ROS)/$H_2O_2$ was measured using 2'-7'Dichlorodihydrofluorescein (DCFH-DA, Sigma Aldrich). DCFH-DA is deacylated intracellularly into a non-fluorescent product, which reacts with intracellular ROS to produce 2'-7' dichlorofluorescein. 2'-7'Dichlorofluorescein remains trapped inside the cell, and can be measured quantitatively. U251 cells were plated onto 6 well dishes and received drug treatments for three days. On the third day, 2 µM DCFH-DA was added to the media (MEM with 0.1% FBS) and the cells were incubated with DCFH-DA overnight. The next day, the cells were trypsinized, washed with PBS, and the fluorescent intensity was measured using a FACS and cell quest pro software.

Polymerase Chain Reaction: Total cellular RNA was isolated from breast cancer cells treated with vehicle control or with CBD. Transcripts for Id-1 and for β-actin were reverse transcribed using SuperscriptII Reverse TranscriptaseII (Gibco-BRL), and polymerase chain reaction performed. The 5' and 3' PCR primers were AGGTGGTGCGCTGTCTGTCT (SEQ ID NO:1) and TAATTCCTCTTGCCCCCTGG (SEQ ID NO:2) for Id-1; and GCGGGAAATCGTGCGTGACATT (SEQ ID NO:3) and GATGGAGTTGAAGGTAGTTTCGTG (SEQ ID NO:4) for β-actin. PCR was performed in buffer containing 1 µM of each of the 5' and 3' PCR primer and 0.5 U of Taq polymerase using 25 cycles for amplification of Id-1 and β-actin cDNAs. The cycle conditions were 45 sec denaturation at 94° C., 45 sec annealing at 55° C., and 1 min extension at 72° C.

Id-1 promoter reporter assays: A SacI-BspHI fragment of 2.2 kb corresponding to the 5' upstream region of human Id-1 gene and driving a luciferase gene in a PGL-3 vector (Promega) was used (Id-1-sbsluc). Cells were plated in six well dishes in medium supplemented with 10% FBS and 5 µg/ml insulin. After 24 hours, cells were cotransfected with 6 µg of luciferase reporter plasmids and 2 µg of pCMVβ (Clontech) using Superfect reagent (Qiagen). pCMVβ contained bacterial β-galactosidase and served to control for variation in transfection efficiency. 3 hours after transfection, the cells were rinsed twice with PBS and were cultured in the absence or presence of CBD for 48-72 h. Cell pellets were lysed in 80 µl of reporter lysis buffer (Promega) for 10 min at room temperature. Lysed cells were centrifuged and supernatants harvested. Luciferase and β-gal assays were performed using Luciferase Assay System (Promega), β-Gal Assay Kit (Clontech) and a 2010 luminometer (Pharmingen).

In-vivo model of breast cancer metastases: 4T1 cells were injected directly into the tail vein of syngeneic BALB/c mice. In this model, cancer cells have direct access to the blood stream resulting in a significant enhancement of lung metastasis and reduced variability in the number of metastases formed as compared to orthotopic models. Two days after i.v. injection of 4T1 cells, the tumor bearing mice were injected i p. once a day with vehicle or compound (1 mg/kg).

Viability Assays using drug combinations and statistical analysis: Multiple viability assays in a 96 well format were run for each compound and the average percent inhibition of cell viability was calculated and transformed to fraction affected (Fa) i.e., percent inhibitory effect. Additional CI values and a dose reduction index (DRI) were also calculated using Compusyn software. After determining the ($IC_{50}$/$Fa_{0.5}$) values of the drugs individually, components were then combined at the following concentration ranges: controls, 0.125× $IC_H$, 0.25×$IC_{50}$, 0.5×$IC_{50}$ and a combination index was calculated where CI<1, =1, and >1 indicate synergism, additive effect, and antagonism, respectively.

Antiproliferative MTT studies using breast cancer MDA-MB231 and MDA-MB436 cell lines with WIN 55, 212-2 and CP55, 940, $\Delta^9$-THC, CBN, CBD, or CBG. The antiproliferative activities of four groups of cannabinoid compounds with MDA-MB231 and MDA-MB436 cells were examined. The groups included: (1) natural cannabis constituents that have affinity for $C_{B1}$ and $C_{B2}$ receptors, THC and CBN; (2) synthetic cannabinoid analogs that have high affinity for $C_{B1}$ and $C_{B2}$ receptors, WIN 55, 212-2 and CP55, 940; and (3) natural cannabis constituents that do not have appreciable affinity for $C_{B1}$ and $C_{B2}$ receptors, CBD and CBG. Breast cancer cells were treated for three days and $IC_{50}$ values were calculated and provided in TABLE 1 below.

TABLE 1

| Compound | MDA-MB231 | MDA-MB436 |
| --- | --- | --- |
| THC | 1.2 (1.0-1.4) | 2.5 (1.8-3.4) |
| CBN | 1.2 (0.9-1.5) | 2.6 (1.8-3.7) |
| WIN 55, 212-2 | 1.7 (1.5-2.2) | 2.4 (1.6-3.4) |
| CP 55, 940 | 2.5 (1.5-4.1) | 1.3 (0.7-1.6) |
| CBD | 1.3 (1.0-1.9) | 1.5 (1.0-1.9) |
| CBG | 2.3 (2.1-2.5) | 2.1 (1.5-3.0) |

According to the $IC_{50}$ numbers (TABLE 1), the rank order of potencies for the anti-proliferative effects of the cannabinoids in MDA-MB231 cells was: CBD=THC=CBN>WIN55, 212-2>CBG=CP55, 940. The rank order of potencies for the antiproliferative effects of the cannabinoids in MDA-MB436 cells was: CBD=CP55, 940>CBG=WIN55, 212-2=$\Delta^9$-THC=CBN. The data demonstrates that cannabidiol (CBD) is an effective inhibitor of human breast cancer cell aggressiveness, invasiveness, and therefore metastasis.

Boyden chamber MDA-MB231 cell invasion studies with CBD, $\Delta^9$-THC, or WIN 55, 212-2. Invasion is an important step towards breast cancer cell metastasis. Therefore, the effects of several cannabinoids were tested on their ability to modulate the migratory and invasiveness activity of the most aggressive human breast cancer cell line, MDA-MB231, in a reconstituted basement membrane in a Boyden chamber. All three compounds tested, i.e., CBD, THC, and WIN 55, 212-2, significantly reduced the invasion of MDA-MB231 cells (FIG. 1, panel A). As was observed with the cell aggressiveness and invasiveness experiments, the most potent inhibitor out of the group of compounds, e.g., CBD, THC, and WIN 55, 212-2 for invasion, was CBD. The $IC_{50}$ value and corresponding confidence limits for CBD were 260 nM (110-610).

Quantitative Western analysis of Id-1 expression in MDA-MB231 cells with CBD, $\Delta^9$-THC, or WIN 55, 212-2. The ability of CBD to regulate the expression of key genes that control breast cancer cell aggressiveness and invasiveness was determined. A potential candidate protein that could mediate the effects of CBD on both phenotypes was the helix-loop-helix protein Id-1. It was determined that treatment of MDA-MB231 cells with CBD led to a concentration-dependent inhibition of Id-1 protein expression (FIG. 1, panel B and panel C). The inhibitory effect of CBD on Id-1 expression occurred at concentrations as low as 100 nM. CBD was more effective at reducing Id-1 protein expression compared to other cannabinoid compounds (FIG. 1, panel C). The CBD concentrations effective at inhibiting Id-1 expression correlated with those used to inhibit the proliferative and invasive phenotype of MDA-MB231 cells. Furthermore, the time period needed to observe the down-regulation of Id-1 protein in the presence of CBD correlated with the inhibitory effects of CBD on the aggressiveness and invasiveness of MDA-MB231 cells (FIG. 1, panel D).

SAR analysis of Id-1 expression in MDA-MB231 cells with (Abn)-CBD receptor, Abn-CBD, 0-1602, CP55, 940, THC, CBN, or CBD. In order to determine the structure activity relationship ("SAR") between cannabinoids and the inhibition of Id-1, MDA-MB231 cells were treated for two days with multiple cannabinoid compounds and Id-1 protein levels were assessed. The compounds used included: (1) agonists and antagonists to the putative abnormal (Abn)-CBD receptor, Abn-CBD and 01602; (2) a synthetic cannabinoid analog that has high affinity for $CB_1$ and $CB_2$ receptors, CP55, 940; (3) natural cannabis constituents that have appreciable affinity for $CB_1$ and $CB_2$ receptors, $\Delta^9$-THC and CBN (FIG. 1, panel E). The greatest inhibition of Id-1 was observed in the presence of CBD (FIG. 1, panel E). Also a small inhibition of Id-1 was observed in the presence of CP55, 940 (FIG. 1, panel E). No inhibition of Id-1 was observed in the presence of THC, 0-1602 and Abn-CBD (FIG. 1, panel E).

The data demonstrates that CBD is an effective inhibitor of Id-1. The inhibition of Id-1 does not appear to be related to the putative Abn-CBD receptor. It also appears that the opened tetrahydropyran ring in CBD is only partially responsible for its activity, since Abn-CBD and 0-1602 did not inhibit Id-1. One potential key structure is the classical cannabinoid aliphatic side chain: a region crucial for the activity of numerous classical and synthetic cannabinoids. CP55, 940 and CBN can partially inhibit Id-1. In comparison to the classical cannabinoid structure ($\Delta^9$-THC), each compound contains the side chain region, and the cyclohexyl ring, however, the pyrane ring is removed in CP55, 940. CP55, 940 has an opened tetrahydropyran ring similar to CBD. The data suggests that a general structural component of CBD, responsible for Id-1 inhibition, is the combination of the opened tetrahydropyran ring and the classical cannabinoid aliphatic side chain.

Assays using Id-1 promoter reporter transfected MDA-MB231 cells with CBD. To determine if Id-1 represented a key mediator of CBD effects in highly aggressive breast cancer cells, Id-1 was constitutively expressed into MDA-MB231 cells (+)Id-1 as described in FIG. 2. The ectopic Id-1 gene, which is not under the control of the endogenous promoter, was introduced in the cells using the pLXSN retroviral vector. As a control, cells were infected with an empty pLXSN vector (−)Id-1. In control cells, treatment with CBD led to a significant reduction in cell invasiveness (FIG. 2, panel A (upper panels) and FIG. 2, panel B). Western blotting confirmed the down-regulation of Id-1 expression in this control cell line (FIG. 2, panel C). In contrast to these results, CBD did not inhibit cell invasiveness (FIG. 2, panel A (lower panels) and FIG. 2, panel B) or Id-1 expression (FIG. 2, panel C) in MDA-MB231(+)Id-1 cells that ectopically expressed Id-1.

Gene Expression Assays looking at Id-1 gene expression with CBD in MDA-MB231 cells. Referring to FIG. 3, panel A, Id-1 mRNA expression was significantly reduced upon treatment with CBD. To determine if this effect was due to the inhibition of transcription, a construct was used that contained the Id-1 promoter fused to a luciferase reporter in a PGL-3 basic vector. This construct was transiently transfected into MDA-MB231 cells. Twenty-four hours after transfection, MDA-MB231-Id-1-luc cells were treated with CBD for 2 or 3 days and luciferase activity was measured (FIG. 3, panel B and panel C). Transfection efficiency and analysis of equal amounts of total protein were controlled by cotransfection of the cells with pCMVB containing β-galactosidase. Treatment with CBD resulted in a significant inhibition of luciferase activity. This effect was time-dependent with the greatest inhibition occurring on day 3. These findings correlated to the data obtained when the expression of the Id-1 protein was assessed by Western analysis.

CBD increases survival in a syngeneic mouse model of breast cancer. While CBD has been shown to inhibit breast cancer metastasis in vivo, pharmacological analysis to determine potency and efficacy has not performed. The 4T1 intravenous (i.v.) mouse model of breast cancer metastasis to assess the activity of CBD in vivo was utilized. In comparison to orthotopic models, when 4T1 cells are injected i.v. through the tail vein, there is a rapid disease progression (2 weeks) and high penetrance of 4T1 tumor formation to the lung which greatly limits variability. This model is therefore highly suited for the analysis of drug potency and efficacy, including the assessment of survival. CBD produced a robust dose-dependent inhibition of metastatic spread of 4T1 cells to the lung in vivo (FIG. 4, panel A). One day after i.v. injection of the breast cancer cells, mice were treated daily for two weeks by intraperitoneal injection with vehicle (used as a control) or CBD at a dose range of 0.1 to 5 mg/kg. CBD inhibited total breast cancer metastasis up to 75% with an $EC_H$ value of 0.3 mg/kg (CI=0.2-0.5). In both the intravenous and orthotopic models, CBD was highly effective at targeting metastatic foci >2 mm (FIG. 4, panel B).

Based on the robust inhibition of lung tumor formation produced by CBD, it was predicted that treatment with the drug would increase survival in tumor bearing mice. A survival study was carried out (FIG. 4, panel C). One day after i.v. injection of 4T1 cells, mice were treated daily with vehicle or 1 mg/kg CBD (a dose producing maximum anti-metastatic activity) until they demonstrated signs of disease progression that necessitated euthanasia (as described in the Methods section). In this highly aggressive mouse model of breast cancer, CBD produced a median significant increase in survival of seven days (p<0.006).

CBD down-regulates Id-1 expression and breast cancer cell proliferation in lung metastatic foci. Id-1 was a key factor whose expression needed to be down-regulated in order to observe the effects of CBD on the reduction of breast cancer cell aggressiveness in vitro. Lung tissue from mice treated with vehicle or CBD (1 mg/kg) were evaluated for Id-1 expression and Ki67, a marker of cellular proliferation (FIG. 5, panel A). Treatment with CBD produced a significant down-regulation of Id-1 expression; 60.9% of lung foci in vehicle-treated mice were strongly positive, while only 5.6% of the lung foci were labeled in the CBD-treated group (FIG. 5, panel B). CBD also produced a significant down-regulation of Ki67 demonstrating its ability to reduce tumor cell proliferation in metastatic foci (FIG. 5, panel C).

CBD was found to inhibit Id-1 and Ki67 expression in metastic foci from lung tissue isolated from mice. Immunohistochemical detection of Id-1 and Ki67 was performed in lung tissues of vehicle and CBD treated mice. Nuclei were stained with hematoxylin. As seen in the panels, upper panels are ×200 magnification and lower panels are ×400, CBD treated cells had noticeably lower hematoxylin staining levels than Vehicle treated cells (FIG. 6, panel A). The intensity of the immunohistochemical (IHC) detection of Id-1 was then graded from 0 to 4. It was found that CBD treated cells had significantly higher amounts of grade 0, grade 1, grade 2 cells, while vehicle had higher amounts of grade 3 and grade 4 cells (FIG. 6, Panel B (left). When the data was presented as a statistical analysis, CBD treated cells averaged around 1 and vehicle treated cells averaged around 2.8 (FIG. 6, Panel B (right)). The percentage of Ki67 positive cells per lung metastatic foci was then evaluated. It was determined that there was a significantly higher percent of ki67 positive cells in Vehicle treated versus CBD treated (FIG. 6, Panel C).

CBD produces a dose-dependent inhibition of metastasis in more advanced stages of breast cancer progression. While CBD was effective at reducing the total number of metastatic foci that formed in the lung, it was significantly more active at targeting metastatic foci ≥2 mm. This suggested the compound could be effective at inhibiting the growth of secondary tumors even after their initial establishment in lung. To determine whether CBD could inhibit the formation of lung tumor foci in more advanced stages of metastasis, mice were treated at a time point where visual lung metastatic foci were already formed (as shown at day seven in FIG. 7, panel A). Mice were injected i.v. with 4T1 cells were kept for one week in order to allow for the formation of visible lung metastatic foci. The mice were then treated with CBD. CBD dose-dependently reduced the growth of established lung metastatic foci and reduced the formation of new metastatic foci (FIG. 7, panel B and panel C). Using a dose of CBD that produced maximum inhibition of metastasis in this model (FIG. 7, panel B), the ability of the cannabinoid to increase survival was also assessed (FIG. 7, panel D). Treatment of mice with CBD (1 mg/kg) starting on day seven also increased survival. While the median increase in survival was only a day, a subset of animals did live three to five days longer (p<0.02).

In-vivo studies of breast and brain tumor formation with CBD. The compounds of the disclosure were effective in inhibiting tumor formation in an in-vivo model. Breast cancer 4T1 cells were subcutaneously injected into the mammary fat pad of BALBc mice (FIG. 8, Panel A), or into the flank of Nude mice (FIG. 8, Panel B). After one week post injection, the mice were treated daily (systemic in A, and peritumoral in B) with CBD (mg/kg). Primary tumor volume was then calculated by measuring the perpendicular largest diameters of the tumor with a caliper and using the formula (L×W²/2). The tumor proliferation in-vivo data demonstrates that CBD is a potent inhibitor of tumor proliferation (FIG. 8, panel A and B), and in some cases completely eradicated tumors (FIG. 8, panel C).

In-vivo metastatic studies using a xenograph mouse model for human breast cancer with CBD. It was found that mice treated with CBD showed a significant reduction in the number of lung metastatic foci in comparison to mice treated with vehicle alone. Lung metastases were generated in Nude mice after tail vein injection of $1 \times 10^6$ MDA-MB231-luc-D3H2LN cells. One day after the injection, the tumor bearing mice were injected i.p. once a day with vehicle or 0.5 mg/kg and 1 mg/kg CBD for three weeks. Visible lung metastases were then counted and measured by using a dissecting microscope. By comparing the percent of metastasis in mice treated with CBD versus mice trated with vehicle alone (100% metastatsis), mice treated with CBD demonstrated at least a 70% reduction in the number of metastases (FIG. 9).

In-vivo late stage metastatic studies using a xenograph mouse model for human breast cancer with CBD. CBD was found to inhibit the formation of metastatic foci in later stages of metastatic progression in mice which were injected with 4T1 cells. Lung metastases were generated in BALB/c mice after tail vein injection of $20 \times 10^5$ mouse 4T1 cells. As 1 mm³ tumors were first detected using a dissecting scope on day 7 (FIG. 10, panel A), this day was chosen to initiate treatments. One week after the tail vein injection of $20 \times 10^5$ mouse 4T1 cells, the tumor bearing mice were injected i.p. once a day with vehicle or 1 mg/kg and 10 mg/kg CBD for seven days. Visible lung metastases were counted and measured by using a dissecting microscope. By comparing the percent of metastasis in mice treated with CBD versus mice trated with vehicle alone (100% metastatsis), mice treated with CBD demonstrated at least a 70% reduction in the number of metastases (FIG. 10, panel B).

Cell viability studies with 4T1 breast cancer cells using CBD in combination with paclitaxel. It was found that CBD can enhance the ability of Paclitaxel to inhibit the viability of 4T1 breast cancer cells. The concentration response curves were first generated for Paclitaxel (PAC), CBD alone, and a combination of CBD and Paclitaxel (FIG. 11, panel A). The inhibitory values from the concentration response curves were then used to calculate combination index (CI) values at multiple combination ratios (FIG. 11, panel B). From which, the data was also used to calculate i) IC50 values, the slope of the curve (m) and a goodness of fit value (r). It was found that CBD acts synergistically with Paclitaxel (FIG. 11, panel C).

Quantitative Western analysis of Id-1 expression in U251 cells with or without CBD treatment. To examine whether CBD would downregulate Id-1 protein expression in a GBM based cell line, quantitative Western analysis was performed with U251 cells. It was determined that treatment of U251 cells with CBD led to a concentration-dependent inhibition of Id-1 protein expression in U251 GBM cells (FIG. 12).

Quantitative western analysis of Id-1 expression in different types of cancer cells with or without CBD treatment. Quantitative Western analysis was performed to examine whether CBD would downregulate Id-1 protein expression in cell lines for breast, prostate, salivary gland, head and neck, and glioblastoma cell lines. It was determined that treatment of cells with CBD (1.5 μM) led to significant inhibition of Id-1 protein expression in the breast cancer cell lines, MDA-MB231 and MDA-MB436 (FIG. 13, panel A); prostate cancer cell lines PC3 and DU145 (FIG. 13, panel B); head and neck cancer cell line, SAS (FIG. 13, panel C (right)); and glioblastoma cell lines, U251 and SF126 (FIG. 13, panel D). For the salivary gland cancer cell line, ACCM, a higher concentration of CBD (2.5 μM) was required to see a significant downregulation in Id-1 expression (FIG. 13, panel C (left)).

Antiproliferative MTT studies using GBM SF126, U87 and U251 cell lines with WIN 55, 212-2 or $\Delta^9$-THC. Two commonly used $CB_1$ and $CB_2$ receptors agonists were chosen to study the effect of cannabinoid treatment on the growth of three human glioblastoma multiforme (GBM) cell lines. THC, a natural cannabis constituent, and WIN 55, 212-2, a synthetic cannabinoid analog, have high affinity for $CB_1$ and $CB_2$ receptors. Human GBM cells were treated with multiple concentrations of THC and WIN 55, 212-2. Cell proliferation was measured using the MTT assay and corresponding $IC_{50}$ values were calculated in three GBM cell lines over a seven day treatment (TABLE 2). SF126 cells overall were most sensitive to the antiproliferative effects of THC and WIN 55, 212-2. Cannabidiol (CBD), a natural cannabis compound that does not have appreciable affinity for $CB_1$ and $CB_2$ receptors, was also tested in the GBM cell line, SF126. The $IC_{50}$ value was 0.73 μM (0.64-0.82). Data are the means and corresponding 95% confidence limits of at least three experiments. $IC_{50}$ values are reported in μM.

TABLE 2

| Compound | SF126 | U87 | U251 |
| --- | --- | --- | --- |
| THC | 0.9 (0.7-1.4) | 1.6 (1.0-2.4) | 1.1 (0.84-1.4) |
| WIN 55, 212-2 | 0.84 (0.74-0.95) | 0.77 (0.65-0.90) | 1.1 (0.97-1.3) |
| CBD | 0.73 (0.64-0.82) | | |

Antiproliferative MTT studies using GBM SF126 cell line WIN 55, 212-2 and CP55, 940, $\Delta^9$-THC, CBN, CBD, or CBG. Treatment periods were shortened to three days during experiments with additional agonists since significant effect were observed at this time point. Three groups of cannabinoid compounds were chosen for a broader analysis of antiproliferative activity in the single GBM cell line, SF126. (1) Natural cannabis constituents that have affinity for $CB_1$ and $CB_2$ receptors, THC and CBN. (2) Synthetic cannabinoid analogs that have high affinity for $CB_1$ and $CB_2$ receptors, WIN 55, 212-2 and CP55, 940. (3) Natural cannabis constituents that do not have appreciable affinity for $CB_1$ and $CB_2$ receptors, CBD and CBG. $IC_{50}$ values for the antiproliferative effects of cannabinoid agonists on SF126 cell growth over a three day treatment were obtained (TABLE 3). SF126 cells were treated with a range of concentrations of multiple cannabinoid agonists, and the corresponding $IC_{50}$ values were calculated. Cell proliferation was assessed using the MTT assay. Data are the means and corresponding 95% confidence limits of at least three experiments. $IC_{50}$ values are reported in µM.

TABLE 3

| Compound | SF126 |
| --- | --- |
| THC | 2.5 (1.8-3.4) |
| CBN | 1.2 (0.9-1.6) |
| WIN 55, 212-2 | 1.3 (1.2-1.4) |
| CP 55, 940 | 3.3 (2.9-3.7) |
| CBD | 1.2 (1.1-1.3) |
| CBG | 1.6 (1.5-1.7) |

The rank order of potencies was: CBD=CBN=WIN 55, 212-2>CBG>THC=CP55940. Again, CBD was one of the most potent compounds tested.

Antiproliferative MTT studies using GBM SF126, U87 and U251 cell lines with CBD. Invasion is also an important step towards brain cancer progression. The disclosure also provides methods and compositions for the treatment of brain cancer progression. Therefore, the ability of CBD to reduce the growth and invasiveness activity of glioblastoma muliforme (GBM) cancer cells was tested. Multiple glioblastoma muliforme (GBM) cell lines were treated for three days. $IC_{50}$ values for the antiproliferative effects of CBD were calculated in multiple GBM cell lines over a three day treatment. Cell proliferation was assessed using the MTT assay. Data are the means and corresponding 95% confidence limits of at least three experiments. $IC_{50}$ values are reported in µM in TABLE 4 below.

TABLE 4

| Cell Line | CBD $IC_{50}$ |
| --- | --- |
| SF126 | 1.2 (1.1-1.3) |
| U87 | 0.7 (0.5-1.0) |
| U251 | 0.6 (0.5-0.7) |

It was determined that U251 cells were the most sensitive to the antiproliferative activity of CBD. CBD was also able to significantly reduce the invasiveness of U251 cells.

Figure 14:
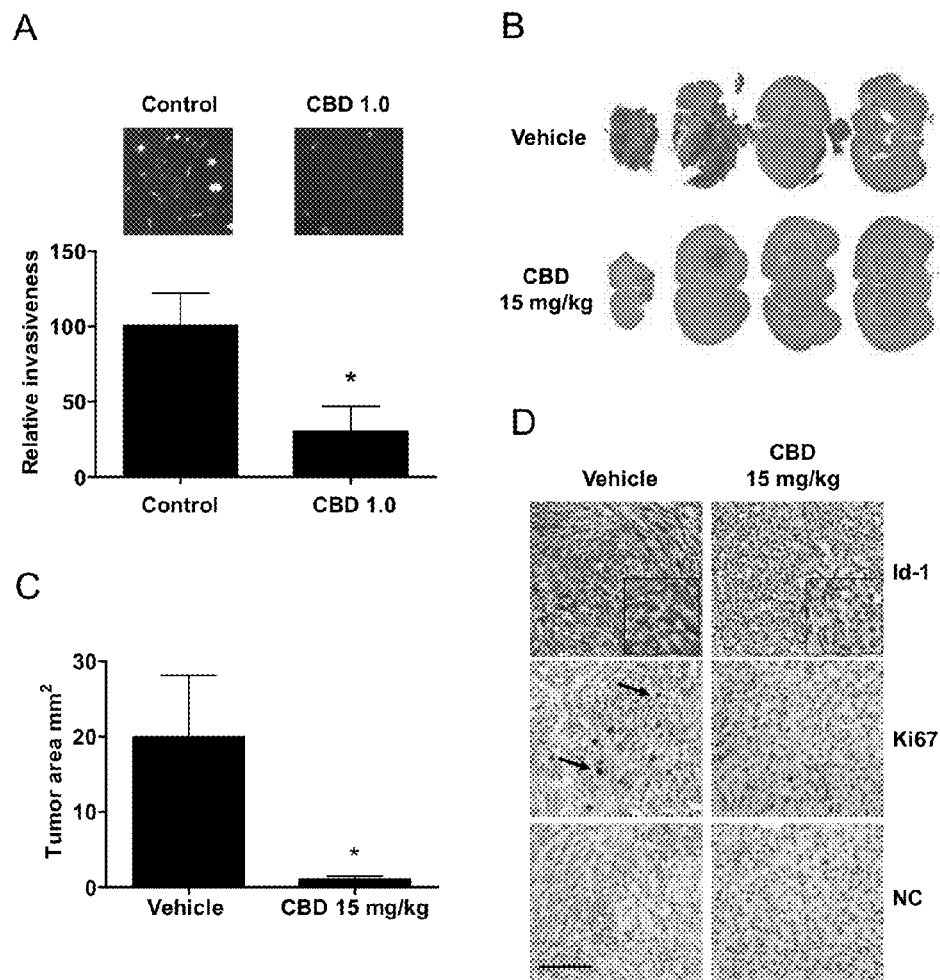
FIG. 14A-D provides that CBD inhibited glioblastoma multiforme ("GBM") cell invasion. (A) $1 \times 10^5$ GFP-labeled U251 cells were placed on top of a 0.5 mm coronal slice of neonatal mouse brain and treated with vehicle (control) or CBD (1.0 μM) for 72 hours. Cells that migrated through the slice were counted using an inverted fluorescence microscope. Data are shown as mean number of cells in triplicate wells. Bars±SE, *p<0.05 Student's t-test. The experiment was repeated three times with similar results. Inset: representative samples of invading cells visualized from the bottom of the slice. (B) Tumors were generated in a xenograft mouse model by intracranial injection of $0.5 \times 10^6$ U251 cells. Each group included five mice. Daily treatments with 15 mg/kg CBD were initiated seven days after injection of the cells, and brains were harvested and sliced at the end of the treatments. (C) Panoramic viewer software (3DHISTECH) was used to measure the area of the tumor in the brain. (*) indicates statistically significant differences from control (p<0.02). (D) Representative sections demonstrate reduction in Id-1 (upper panel) and Ki67 (middle panel) expression in tumors responsive to CBD treatment. Bar=100 μM. The insets (top panels) represent a 20 fold magnification. Negative IgG controls (NC) are also shown.

Effects of CBD on GBM cell invasion in In Vivo Studies. To determine whether CBD could inhibit GBM cell invasion through intact brain tissue, an organotypic brain slice assay was utilized. GFP-labeled U251 cells were treated for two days in culture with vehicle or CBD. On the third day, the cells were harvested and transferred to the top of a 0.5 mm coronal rat brain slice obtain from a postnatal day 3 rat pup. A porous cell culture insert containing the slice was suspended for three days in a well containing conditioned media with either vehicle or 1 µM CBD. After three days, GFP-labeled cells that successfully invaded through the slice are visualized using an inverted microscope and we found that CBD was highly effective at inhibiting invasion of U251 cells through the organotypic brain slice (FIG. 14, panel A). GBM tumors were generated in nu/nu mice by intracranial injection of U251 GBM cells. 7 days after tumor implantation, mice were injected systemically (intraperitoneal) with 15 mg/kg CBD 5 days a week for 28 days until vehicle-treated animals demonstrated signs of significant disease progression (hunched posture and reduced mobility), when all mice in the study were euthanized in order to compare tumor growth. CBD produced a robust reduction of GBM progression, decreasing the tumor area by 95% (FIG. 14, panels B and C). In one of the five mice treated with CBD, no tumor cells were observed in any of the brain regions analyzed. Target validation showed that, in tumors responding to treatment, CBD produced a significant down-regulation of Id-1 expression (FIG. 14, panel D). This occurred concomitantly with a decrease in tumor cell proliferation (the number of Ki67-positive nuclei was decreased by 87%±9 (p<0.0001, Student's t-test)) (FIG. 14, panel D).

Figure 15:
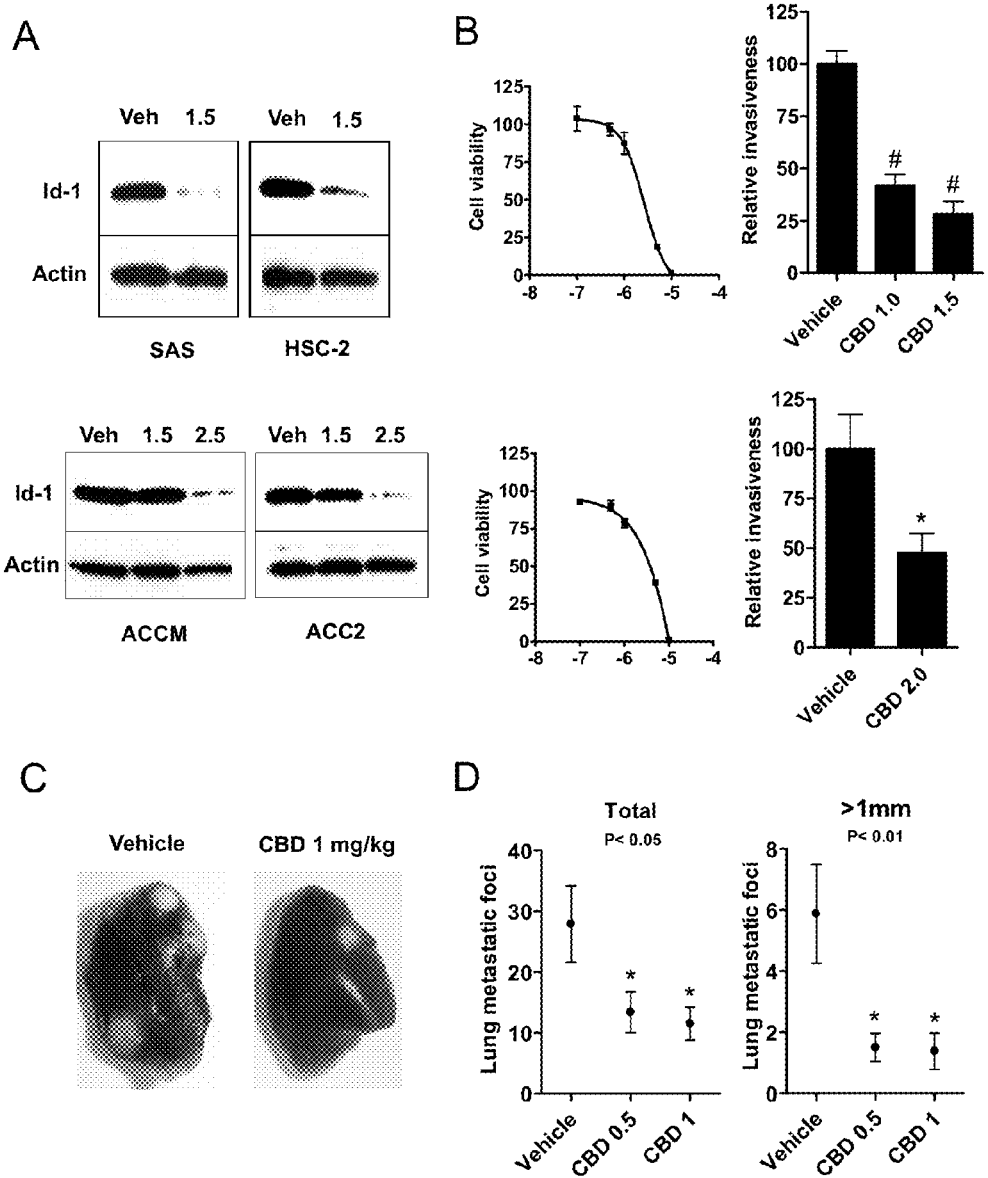
FIG. 15A-D demonstrates the effect of CBD on the aggressiveness of head and neck as well as salivary gland cancer cells. (A) Head and neck cancer cell lines (SAS and HSC-2 in the upper panels) and salivary gland cancer cell lines (ACCM and ACC2 in the lower panels) were treated with CBD. Down-regulation of Id-1 gene expression was observed in all cell lines. (B) Effect of CBD on SAS tumor cell viability and invasiveness is shown in the upper panels. Effect of CBD on ACCM tumor cell viability and invasiveness is shown in the lower panels. (C) Representative pictures of lung metastasis after injection of ACCM cells and daily treatment with CBD. (D) The number of lung metastatic foci after injection of ACCM cells was significantly reduced upon CBD treatment. The total number of foci is shown in the left panel and the number of metastatic foci >1 mm is shown in the right panel.

Measuring the effect of CBD on the aggressiveness of head and neck as well as salivary gland cancer cells. Head and neck cancer cell lines (SAS and HSC-2 in the upper panels) and salivary gland cancer cell lines (ACCM and ACC2 in the lower panels) were treated with CBD. Id-1 gene expression was downregulated in all cell lines (FIG. 15, panel A). CBD had a significant effect on SAS tumor cell viability and invasiveness (FIG. 15, panel B (upper panels)). CBD also had a significant effect on ACCM tumor cell viability and invasiveness (FIG. 15, panel B (lower panels)). There was a significant reduction in the number and size of lung metastases after mice were injected with ACCM cells and treated daily with CBD (FIG. 15, panel C). The number of lung metastatic foci after injection of ACCM cells was significantly reduced upon CBD treatment (FIG. 15, panel D). The number of metastatic foci greater than >1 mm was also significantly reduced upon treatment with CBD (FIG. 15, panel D, (right)).

Figure 16:
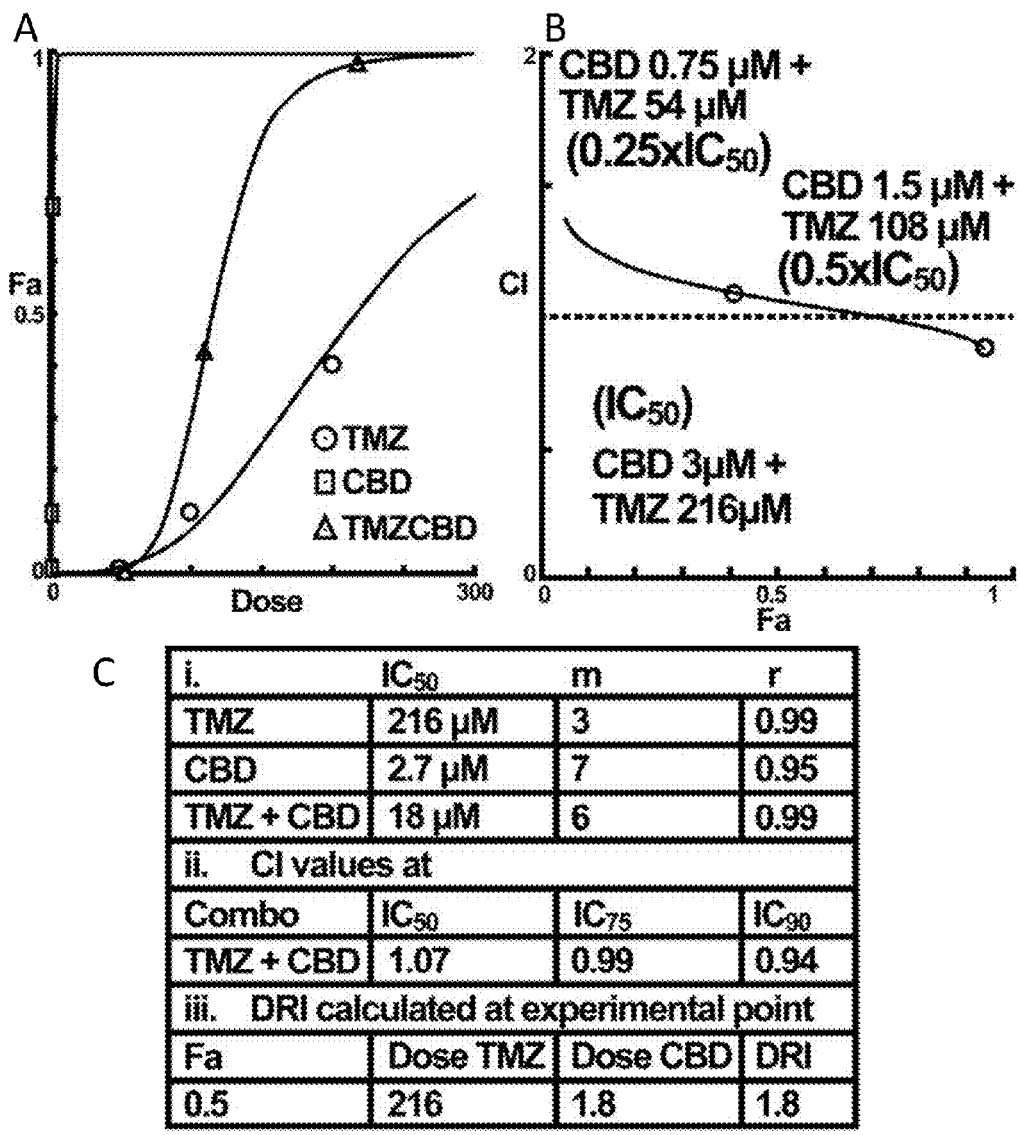
FIG. 16A-C provides data showing that at optimal combined ratios, CBD can enhance the ability of temozolomide to inhibit the viability of U251 GBM cells. (A) Concentration response curves were generated for temozolomide ("TMZ") and CBD alone and in combination. (B) The inhibitory values from the concentration response curves were used to calculate combination index (CI) values at multiple combination ratios where CI<1, =1, and >1 indicate synergism, additive effect, and antagonism, respectively. (C) These data were used to calculate (i) $IC_{50}$ values, the slope of the curve (m) and a goodness of fit value (r). Additionally, (ii) CI values and (iii) a dose reduction index ("DRI") were calculated using Compusyn software.

Cell viability studies with U251 GBM cells using CBD in combination with Temozolomide. CBD was found to enhance the ability of Temozolomide to inhibit the viability of U251 GBM cells. The concentration response curves were first generated for temozolomide, CBD alone, and a combination of CBD and temozolomide (FIG. 16, panel A). The inhibitory values from the concentration response curves were then used to calculate combination index (CI) values at multiple combination ratios (FIG. 16, panel B). From which, the data was also used to calculate (i) $IC_{50}$ values, the slope of the curve (m) and a goodness of fit value (r). It was found that CBD acts synergistically with Temozolomide (FIG. 16, panel C).

Figure 17:
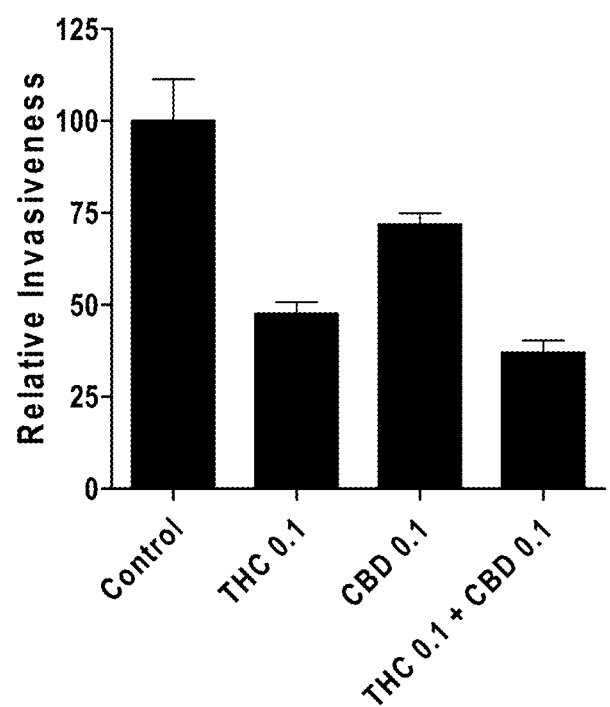
FIG. 17 demonstrates that THC, CBD, and a combination of CBD and THC were able to significantly reduce the invasiveness of U251 cells.

Boyden chamber U251 cell invasion studies with CBD and/or $\Delta^9$-THC. In addition to uncontrolled cell growth, a hallmark phenotype of aggressive GBM tumor cells is their ability to migrate away for the primary tumor of origin and invade into neighboring CNS tissue. Experiments were performed to determine whether the addition of CBD to $\Delta^9$-THC would improve the activity of the compound to inhibit migration and invasion through a reconstituted basement membrane in a Boyden chamber. $\Delta^9$-THC effectively inhibited the invasiveness of U251 cells (FIG. 17). Additionally, $\Delta^9$-THC was significantly more potent at inhibiting U251 cell invasiveness in comparison to the inhibition of cell growth and induction of apoptosis. The predicted $IC_{50}$ for the ability of $\Delta^9$-THC to inhibit U251 cell invasiveness was 85 nM (49-

150). Whereas both THC and CBD were able to inhibit U251 cell invasiveness, the combined addition of the compounds did not result in activity suggesting a synergistic interaction (FIG. 17).

2×2 Antiproliferative MTT assays using Gliobastoma U251, U87, and SF126 cell lines with $\Delta^9$-THC and/or CBD. Non-psychoactive cannabinoids, compounds that do not interact efficiently with $CB_1$ and $CB_2$ receptors, can modulate the actions of THC. The experiments described below, using multiple human glioblastoma multiforme ("GBM") cells lines, compared the antiproliferative activity of non-psychoactive cannabinoids to synthetic and natural $CB_1$ and $CB_2$ agonists. The activity of THC was tested in combination with CBD. In U251 and SF126 cell lines, THC in combination with a lower concentration of CBD, acted synergistically to inhibit GBM cell growth and induce apoptosis. The inhibitory properties of the combination were the result of activation of $CB_2$ receptors and a corresponding increase in oxygen radical formation. The signal transduction mechanisms associated with the effects of the combination treatment were different from those observed with the individual compounds. The disclosure demonstrates that the addition of CBD to THC improves the overall potency and efficacy of $\Delta^9$-THC in the treatment of patients with cell proliferative disorders such as, for example, GBM.

Treatment groups were divided into (1) no treatment (control), (2) THC alone, (3) CBD alone, (4) THC and CBD combined. Positive and negative aspects of constituent interaction were determined in this 2×2 design using 2-way analysis of variance as described by. In the proliferation assays, $IC_{50}$ values with corresponding 95% confidence limits were calculated using non-linear analysis of logged data (Graph-Pad Prism, San Diego, Calif.). Significant differences were also determined using ANOVA where suitable. Bonferroni-Dunn post-hoc analyses were conducted when appropriate. p values <0.05 defined statistical significance.

Figure 18:
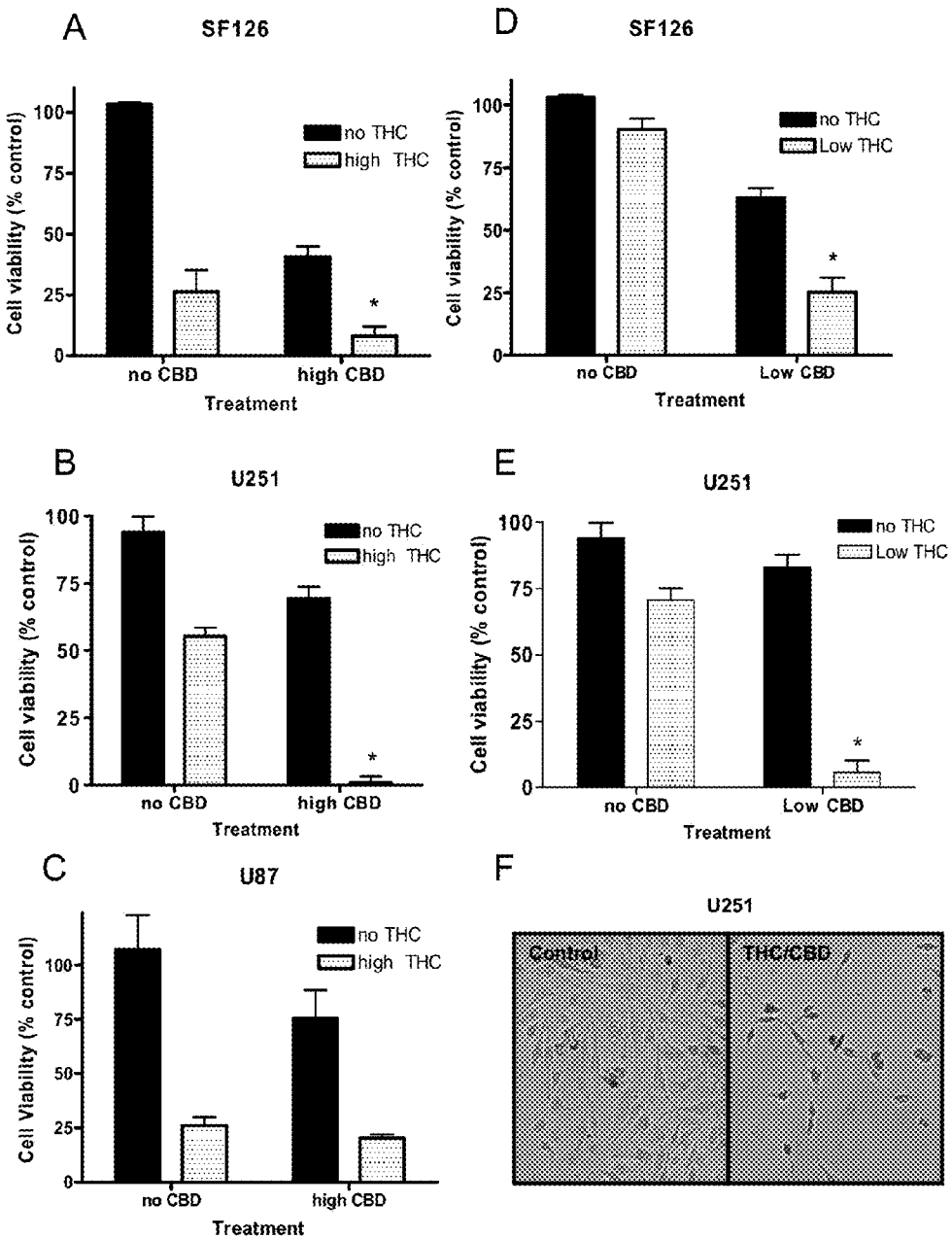
FIG. 18A-F provides data indicating that combinations of $\Delta^9$-THC and CBD produced synergistic effects on the inhibition of cell growth in SF216 and U251 cells but not in U87 cells. A 2×2 factorial design was used. (A) Depicts results for SF126. (B) Depicts results for U251. (C) Depicts results for U87MG cells that were treated for three days with vehicle/no drug, $\Delta^9$-THC, CBD, or a combination of $\Delta^9$-THC and CBD. Concentrations of $\Delta^9$-THC and CBD that produce only minimal effects on cell proliferation (denoted low as opposed to high) were also tested in 2×2 factorial design in: (D) for SF126, and (E) for U251 cells. Cell proliferation was measured using the MTT assay. The absorbance of the media alone at 570 nm was subtracted, and percent control was calculated as the absorbance of the treated cells/control cells× 100. (F) Provides representative light microscope images of the effects of the combination treatment on U251 cells from the experiment shown in (E), presented as (10×). Data are the mean of at least 3 independent experiments, bars±SE.

Three GBM cell lines, SF126, U251 and U87 cells, were used to determine the effects of combination treatments. When applied in combination, THC and CBD produces synergistic inhibition of cell growth in SF126 and U251 cells but not in U87 cells (FIG. 18, panels A, B, and C). Concentrations of THC and CBD alone that produce only minimal effects on cell proliferation were combined and further tested in a 2×2 factorial design in the positive responding cell lines (SF126 and U251) (FIG. 18, panels D, E, and F). The most pronounced synergistic activity was observed with U251 cells, therefore, this cell lines was used to determine the mechanism of action for the combination effect. The 4:1 (1.7 µM: 0.4 µM) ratio of THC and CBD was used for the following experiments.

It was determined that THC and CBD act synergistically to inhibit the growth of multiple GBM cell lines. It has been suggested that non-psychoactive cannabinoid constituents can either potentiate or inhibit the actions of THC. The $CB_1$ and $CB_2$ receptor agonist, THC, can inhibit GBM growth in vitro and in vivo. CBD, a cannabinoid constituent with negligible affinity for $CB_1$ and $CB_2$ receptors can also inhibit the growth of GBM in vitro and in vivo. The disclosure demonstrates that of the non-psychoactive cannabinoids, CBD is a far superior inhibitor of GBM cell growth.

Figure 19:
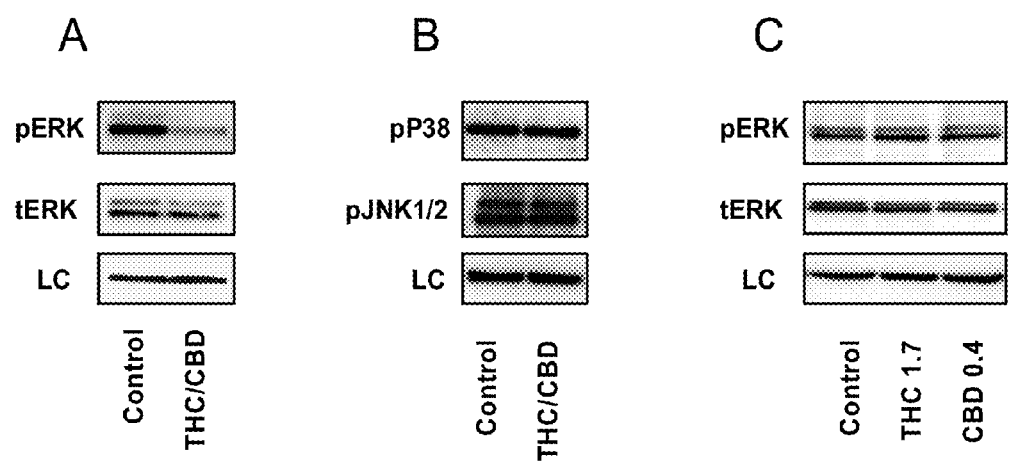
FIG. 19A-C demonstrates that a combination treatment of $\Delta^9$-THC and CBD specifically inhibited ERK activity. The effects of cannabinoids on MAPK activity were analyzed using Western analysis. U251 cells were treated with vehicle or a combination of Δ9-THC (1.7 μM) and CBD (0.4 μM) for two days. Proteins were extracted and analyzed for (A) pERK and total ERK, and (B) pJNK 1/2 and p38 MAPK. U251 cells were treated with A9-THC (1.7 μM) and CBD (0.4 μM) alone and analyzed for (C) pERK and total ERK. Either α-tubulin or β-actin was used as a loading control (LC). Blots are representative of at least 3 independent experiments.

Quantitative western analysis of pERK, JNK, and p38 MAPK expression in U251 cells with CBD and/or $\Delta^9$-THC. The disclosure demonstrates that the combination treatment of $\Delta^9$-THC and CBD leads to the modulation of specific mitogen activated kinases (MAPK). The regulation of ERK, JNK, and p38 MAPK activity plays a critical role in controlling cell growth and apoptosis. Therefore in U251 cells, it was determined whether treatment with a combination of THC and CBD could alter the activity of ERK, JNK, and p38 MAPK. Treatment with the combination of cannabinoids led to a profound down-regulation of p-ERK but no significant change in total ERK (FIG. 19, panel A). Additionally, no inhibition of JNK or p38 MAPK activity was observed (FIG. 19, panel B). When U251 cells were treated with individual concentration of THC and CBD, instead of the combination, no changes in pERK were observed (FIG. 19, panel C).

Figure 20:
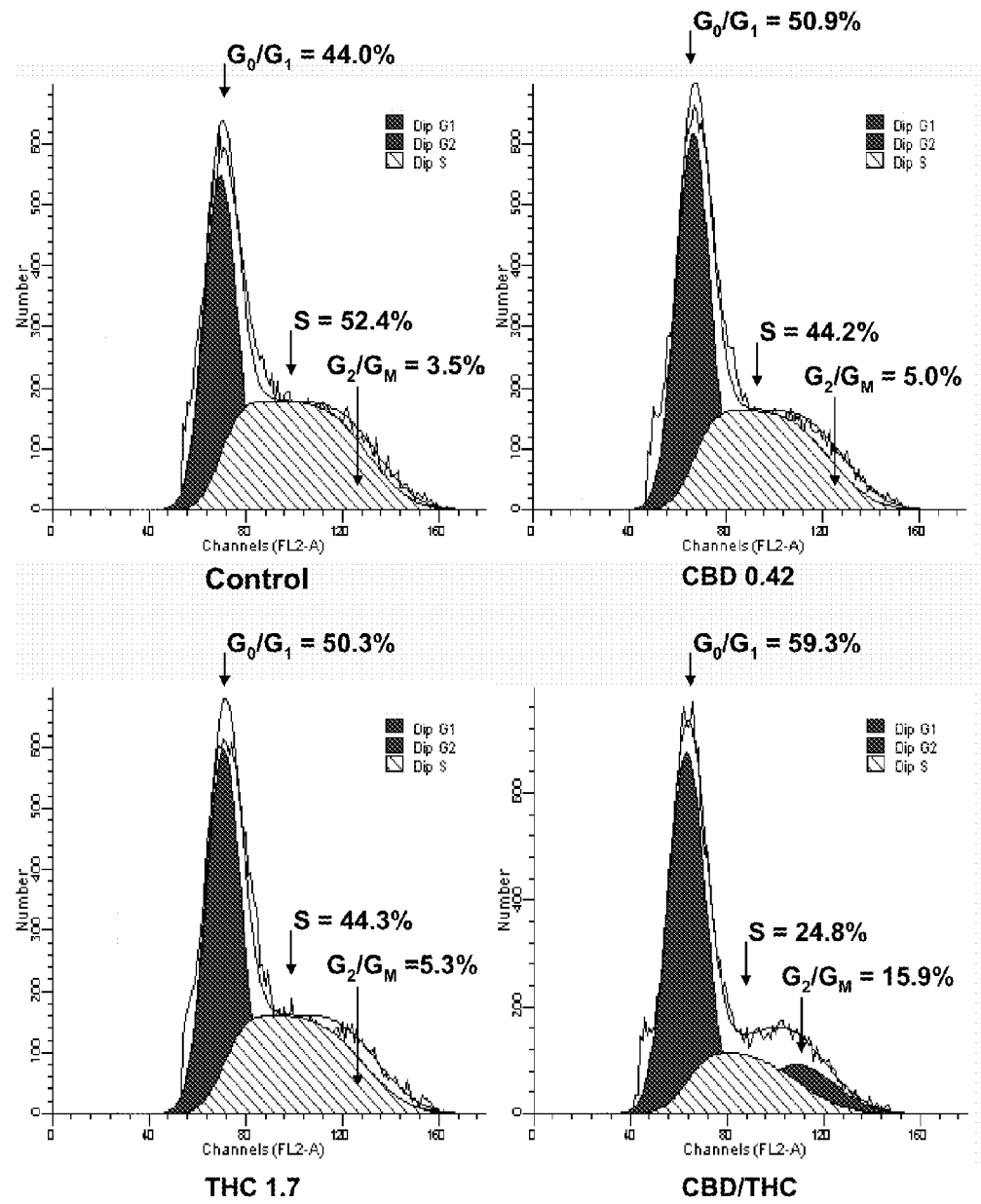
FIG. 20 provides that the combination treatment of $\Delta^9$-THC and CBD produced G1/S cell cycle arrest. Cell cycle was measured using PI staining and FACS analysis. U251 cells were treated for three days with THC (1.7 μM), CBD (0.4 μM), or a combination of THC (1.7 μM) and CBD (0.4 μM). Cells were collected and analyzed using a desktop FACS Calibur with Cell Quest Pro software. Modfit was used to determine the percentage of cell in $G_0/G_1$, S and $G_2/G_M$ phase.

Apoptosis studies using U251 cells with $\Delta^9$-THC and/or CBD. The disclosure further demonstrates that the combination treatment of THC and CBD induces apoptosis. Significant reductions in ERK activity have been shown to lead to induction of apoptosis. The large reduction in GBM cell growth and ERK activity, observed in the presence of the combination treatment of THC and CBD, suggested there would be a corresponding modulation of the cell cycle and programmed cell death. Therefore, U251 cells were treated with THC and CBD alone or with the combination of the two, and cell cycle was analyzed using cell flow cytometery (FIG. 20). The combination of THC and CBD produced an increase in the population of cells in G1 phase and a decrease in cells in S phase. Additionally, there was an increase in the population of cells in the G2/M phase. These changes in G1, S and G2/M phase are hallmarks of cell cycle arrest.

Figure 21:
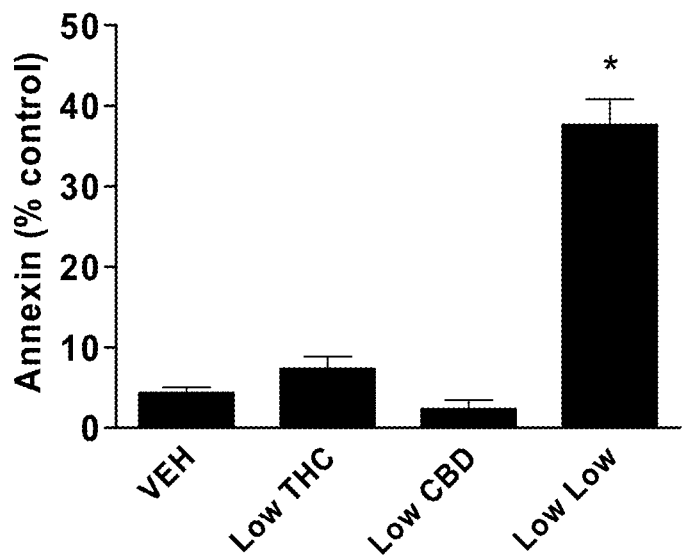
FIG. 21 presents data indicating that when combined, $\Delta^9$-THC and CBD produced greater than additive effects on the cell cycle inhibition and induction of apoptosis in U251 cells. U251 cells were treated for three days with THC (1.7 μM), CBD (0.4 μM), or a 4:1 combination ratio [$\Delta^9$-THC (1.7 μM)/CBD (0.4 μM)]. The number of cells staining positive for annexin (apoptosis) were measured using FACS analysis. Percent control was calculated as positive annexin staining of the treated cells minus control cells. Data are the mean of at least 3 independent experiments, bars±SE. Data were compared using a one-way ANOVA with a corresponding Tukey's post-hoc test. (*) indicates statistically significant differences from control (p<0.05).

When administered separately, THC (1.7 µM) and CBD (0.4 µM) both produced increases in the population of cells in G1 and G2/M phase and decreases in cells in S phase. Albeit, the magnitude of these effects was reduced compared to those observed with the combination treatment. By measuring annexin concentration, a large increase in apoptosis was observed when THC and CBD were combined (FIG. 21). Separately THC (1.7 µM) and CBD (0.4 µM) did not produce significant changes in apoptosis (FIG. 21).

Figure 22:
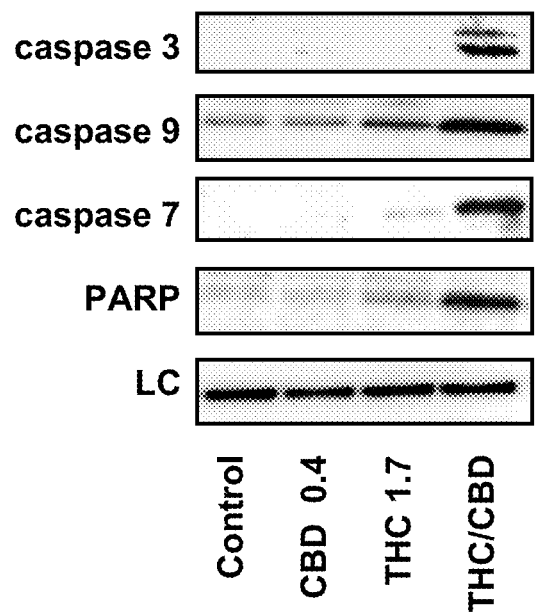
FIG. 22 demonstrates that when combined, $\Delta^9$-THC and CBD produced a significant increase in the activation of multiple caspases. The effects of cannabinoids on caspase and p8 expression were analyzed using Western analysis. U251 cells were treated for three days with THC (1.7 μM), CBD (0.4 μM), or a combination of $\Delta^9$-THC (1.7 μM) and CBD (0.4

The combination treatment of $\Delta^9$-THC and CBD produced the activation of multiple caspases. Caspases play a primary role in the regulation of programmed cell death. Therefore, multiple caspase pathways were evaluated to determine mechanisms by which the combination treatment increased apoptosis. Treatment with the combination of THC and CBD led to a significant up-regulation of caspase 3, 7, and 9 activities as well as an increase in PARP (FIG. 22). Small increases in the activity of caspase 7, caspase 9 and PARP but not caspase 3 were observed when U251 cells were treated with the individual concentration of THC (FIG. 22). In the presence of CBD alone no changes in caspase activity were observed (FIG. 22).

Apoptosis induced by the combination of THC and CBD can be at least partially blocked by administering cannabinoid receptor antagonists. Apoptosis produced by the combination of THC and CBD was partially blocked by the $CB_2$ receptor antagonist, SR144528, but complete reversal was observed in the presence of the anti-oxidant, α-tocopherol (TCP) (FIG. 23, panel A). The concentrations of the individual cannabinoids (THC and CBD) were next increased in order to attempt to match levels of apoptosis produced by the combination treatment. The purpose of these experiments was to determine whether the compounds alone recruited similar pathways as compared to the combination of THC and CBD. When U251 cells were treated with THC alone, the induction of apoptosis was completely blocked by α-tocopherol and partially blocked by the CB2 antagonist, SR144528 (FIG. 23, panel B). However, THC alone could not produce the level of apoptosis observed with the combination treatment (FIG. 23, panel A and B). This finding was not simply an issue of the treatment concentration used since continuing to increase levels of THC did not produce a greater induction of apoptosis. When U251 cells were treated with CBD alone, the induction of apoptosis was completely blocked by α-tocopherol but no reversal was observed with SR144528 (FIG. 23, panel C); this result would be expected since CBD does not interact efficiently with either $CB_1$ or $CB_2$ receptors.

The ability of the higher concentrations of THC and CBD alone to inhibit p-ERK were also studied and compared to the combination treatment (FIG. 23, panel D). Again, the combination treatment produced a profound down regulation of p-ERK. However, the higher concentration of $\Delta^9$-THC alone had no effect on p-ERK activity. The higher concentration of CBD produced a small inhibition of p-ERK. This suggests the pathway(s) activated by the THC and CBD combination that leads to p-ERK down-regulation, is unique to the combination treatment. As predicted by α-tocopherol blockade, the combination of THC and CBD produced a significant increase in the formation of ROS as assessed by DCDHF-DA oxidation (FIG. 23, panel E).

A wide range of cannabinoids inhibit the proliferation of human GBM cells. In addition to testing THC, the analysis included the non-psychoactive cannabis constituents CBD, CBN and CBG. Overall, CBD was the most potent inhibitor tested.

Combining THC and CBD together resulted in a synergistic increase in the inhibition GBM growth and produced significant increases in apoptosis. This synergistic activity occurred in two of three GBM cell lines tested. The synergistic inhibition of GBM cell growth was in part the result of a greater amount of apoptosis being produced in presence of the combination compared to administration of THC alone. Treatment of U251 cells with the combination of cannabinoids led to a profound down-regulation of ERK activity, but not p38 MAPK and JNK1/2. The reduction of ERK activity was specific for the combination treatment indicating that all the effects observed were not simply due to an increase in potency of THC upon co-application with CBD. The specific reduction in ERK activity, observed in the presence of the combination treatment, may be one of the primary mechanisms leading to the synergistic increase in inhibition of GBM cell growth and the induction of apoptosis. THC was also effective at inhibiting the invasiveness of U251 cells. However, there was no suggestion of a synergistic interaction upon addition of CBD.

ROS measurement studies using GBM cells with THC and/or CBD. The disclosure demonstrates that the synergistic inhibitory effects of combination treatment are the result of $CB_2$ receptor activation and production of oxygen radicals. Depending on the cancer cell line and compound used, studies have linked the inhibitory activity of cannabinoids to activation of $CB_1$, $CB_2$, vanilloid (VR1) receptors, and the production of oxygen radicals. An increase in apoptosis produced by the combination of THC/CBD was partially dependent on $CB_2$ receptor activation. Apoptosis produce by treatment of $\Delta^9$-THC alone was also partially dependent on $CB_2$ receptor activation. Importantly, the induction of apoptosis in the presence of the combination treatment was significantly greater than that observed with THC alone. Apoptosis produced by CBD in U251 cells was not dependent $CB_2$ receptor activation. Comparable results with CBD were also observed using another GBM cell line, SF126. Apoptosis produced by the combination of THC and CBD was greatly dependent on the production of oxidative stress and resulted in the activation of both extrinsic and intrinsic caspase pathways.

$\Delta^9$-THC and CBD activate unique pathways in GBM cells that ultimately culminate in inhibition of cancer cell growth and invasion as well as induction of cell death. The data presented here show that the synergistic activity of the combination treatment is due in part to a specific convergence of distinct pathways controlled by the individual compounds. This convergence of inhibitory pathways unique to THC and CBD leads to an overall synergistic reduction of GBM cell growth and survival. Combinations, compared to individual drug treatments with specific cannabinoid-based compounds may represent a significant improvement for the treatment of patients with GBM. These synergistic effects may also be present in additional cancers. With the discovery of a specific molecular mechanism potentially explaining the synergistic effects, additional combination treatments may able to be refined in order to further improve antitumor activity.

Development novel CBD derivatives with enhanced antineoplastic activities. The previous data suggest key structural requirements of CBD impart the ability to inhibit Id-1 expression. It was also shown that classical $CB_1$ and $CB_2$ receptor agonists (e.g. THC) do not target Id-1. $CB_2$ selective cannabinoid agonists, having limited activity at $CB_1$ receptors (psychoactivity), but sharing structural similarities with CBD were developed to modulate Id-1 expression more effectively than CBD. Moreover, these novel CBD based analogs would not only effectively target Id-1 but would also have the advantage of targeting two distinct cannabinoid antitumor pathways leading to enhanced antitumor activity. Two separate screens of selective resorcinol derivatives were performed by testing for selectivity to $CB_2$ receptors and for their ability to inhibit MDA-MB231 cell viability (TABLE 5, summary). In the first screen, a candidate compound O-1422 was found to be as potent as CBD. In the second screen, a candidate compound O-1663 was found to be 2.2 fold more active than CBD (TABLE 5). The structure of O-1442 and O-1663 are almost identical with the exception of one R group. A smaller subset of the same analogs, including O-1442 and O-1663, were further screened for their ability to inhibit 4T1 breast cancer cell viability in anticipation of running in vivo experiments in immune competent mice (TABLE 5). Similar activities were observed in both MDA-MB231 and 4T1 cells. While both compounds were selective for targeting $CB_2$ receptors over $CB_1$ receptors, O-1442 still had a relatively high affinity for $CB_1$ receptors (potential for significant psychoactivity) and was less potent than the O-1663 CBD analog at inhibiting breast cancer cell viability. The O-1663 CBD analog was found to have a lower affinity for $CB_1$ receptors in comparison to THC and produced little activity in the tetrad assay-measure of psychoactive properties of cannabinoids. Based upon the data presented in TABLE 5, the O-1663 CBD analog was evaluated in additional studies.

TABLE 5

| Cell line | Compound | $IC_{50}$ | Confidence Limits |
|---|---|---|---|
| MDA-MB231 | THC | 3.0 μM | (2.3-3.9) |
| MDA-MB231 | CBD | 1.9 μM | (1.5-2.5) |
| MDA-MB231 | O-1663 | #0.85 μM | (0.79-0.91) |
| MDA-MB231 | O-1422 | 1.7 μM | (1.5-2.0) |
| MDA-MB231 | O-2137 | 45%$^a$ | |
| MDA-MB231 | O-1657 | 39%$^a$ | |
| MDA-MB231 | O-1424 | 22%$^a$ | |
| MDA-MB231 | O-3853 | 3%$^a$ | |
| MDA-MB231 | O-2981 | 15%$^a$ | |
| MDA-MB231 | O-2988 | 26%$^a$ | |
| MDA-MB231 | O-5788 | 0%$^a$ | |
| MDA-MB231 | O-5832 | 0%$^a$ | |
| MDA-MB231 | O-4233 | 0%$^a$ | |
| MDA-MB231 | O-5881 | 0%$^a$ | |
| 4T1 | THC | 2.3 μM | (1.9-2.7) |
| 4T1 | CBD | 1.8 μM | (1.2-2.7) |
| 4T1 | O-1663 | #0.83 μM | (0.79-0.87) |
| 4T1 | O-1422 | 4.5 μM | (1.5-12) |

TABLE 5-continued

| Cell line | Compound | IC$_{50}$ | Confidence Limits |
|---|---|---|---|
| 4T1 | O-2137 | 3.5 µM | (1.8-7.0) |
| 4T1 | O-3853 | 7%[a] | |
| 4T1 | O-5788 | 0%[a] | |

In respect to TABLE 5, data represent the mean with corresponding confidence limits for 3-5 independent confidence limits for 3-5 independent determinations.
[a]Percent inhibition of cell viability produced at 5 µM.
[#]Statistically significant increase in potency compared to CBD (p < 0.05)

Antiproliferative MTT studies using breast cancer MDA-MB231 cell line with CBD and O-1663 CBD analog. In further cell viability in-vitro studies with CBD, a novel synthetic CBD derivative, O-1663 CBD analog, was found to be unexpectedly far superior to CBD in inhibiting human breast cancer cell and glioblastoma aggressiveness, invasiveness, and therefore metastasis (FIG. 24, panels A and B). The IC$_{50}$ values were calculated and provided in TABLE 6 below.

TABLE 6

| Compound | MDA-MB231 |
|---|---|
| CBD | 2.2 (1.9-2.6) |
| O-1663 CBD analog | 1.2 (0.9-2.0) |

Antiproliferative MTT assays using the GBM U251 cell line with CBD or CBD 1663 analog. As with the MDA-MB231 cell line, CBD 1663 analog exhibits a stronger inhibitory antiproliferative effect than CBD in the GBM U251 cell line, by a surprisingly large margin (FIG. 24, Panel B). The IC$_{50}$ values were calculated and provided in TABLE 7 below.

TABLE 7

| Compound | U251 |
|---|---|
| CBD | 2.9 (2.7-3.2) |
| O-1663 CBD analog | 0.53 (0.54-0.56) |

Quantitative western analysis of Id-1 expression in MDA-MB231 cells and U251 cells with CBD or O-1663 CBD analog. To examine whether O-1663 CBD analog's potent inhibitory effect on cancer cell proliferation was associated with downregulating Id-1 protein expression, quantitative Western analysis for Id-1 protein expression was performed. MDA-MB231 breast cancer cells and U251 GBM cells were treated with 1.0 µM of cannabinoid for two days and then analyzed for Id-1 protein expression by quantitative Western analysis. It was determined that cancer cells treated with the 0-1663 CBD analog downregulated Id-1 protein expression to a far greater extent than CBD (FIG. 24, panel C).

Boyden chamber MDA-MB231 cell invasion studies with CBD and O-1663 CBD analog. Boyden chamber studies for invasion by MDA-MB231 or U251 cells were performed with either CBD or O-1663 CBD analog. The O-1633 CBD analog was found to be far superior to CBD in inhibiting invasion by the cancerous cells (FIG. 24, panel D).

O-1663 CBD analog but not CBD reduces breast cancer cell aggressiveness through the activation of CB$_2$ receptors. To Directly test whether the O-1663 CBD analog could co-target two distinct cannabinoid antitumor pathways, the effects of CBD and the O-1663 CBD analog on cell viability with multiple antagonists were probed (FIG. 25). The ROS scavenger, a-TOC was able to reverse the inhibitory effects of CBD on cell viability. A CB$_1$ receptor antagonist had no effect on reversing the activity of CBD (FIG. 25, panels A and B). While a subtle reversal of CBD activity was observed with the CB$_2$ receptor antagonists SR14458 it was not significant (FIG. 25, panels A and B). In contrast, the CB$_2$ receptor agonist SR14458 was able to partially reverse the inhibitory effects of the O-1663 CBD analog on breast cancer cell viability (FIG. 25, panels A and B). The ability of the O-1663 CBD analog and CBD to inhibit invasion was next compared (FIG. 25, panel C). O-1663 was 1.7 fold more potent than CBD at inhibiting the invasion of MDA-MB231 cells. The IC$_{50}$ value and corresponding confidence limits for the O-1663 CBD analog and CBD were 0.6 µM (0.5-0.7) and 1 µM (0.8-1.2), respectively.

O-1663 CBD analog is more potent than CBD at inhibiting Id-1 expression and up-regulating ROS. Whereas a CBD (1 µM) produced a partial reduction of Id-1 expression, treatment with the same concentration of the O-1663 CBD analog produced almost a complete down-regulation of Id-1 expression in both MDA-MB231 and 4T1 cells (FIG. 25, panel 4). Id-2 is a marker of good prognosis in breast cancer patients, is important for the maintenance of a differentiated and noninvasive phenotype in breast cancer cells, and is up-regulated following inhibition of Id-1. As demonstrated in FIG. 25, panel D, the O-1663 CBD analog was more potent than CBD at up-regulating Id-2 expression in breast cancer cells demonstrating specificity for targeting Id-1. In culture, CBD-induced generation of ROS is a primary mechanism that leads to inhibition of cell growth, invasion, and survival across multiple cancers. The generation of ROS by CBD leads to the inhibition of Id-1 expression in breast cancer cells. Using the approximate IC$_{50}$ for CBD and THC for inhibition of cell proliferation and viability, it was found that CBD produced a robust up-regulation of ROS whereas THC produced no significant increase in ROS (FIG. 26, panel A). The ability of CBD and the O-1663 CBD analog to stimulate the production of ROS was next compared. It was found that the O-1663 CBD analog was significantly more potent and efficacious than CBD at generating ROS. The involvement of CB$_2$ receptors in the productions of ROS produced by CBD and the O-1663 CBD analog was next investigated. In the presence of SR14458, there was a small but significant reversal of ROS whereas >50% of the ROS produced by the O-1663 CBD analog was reversed in the presence of SR14458 (FIG. 26, panel B).

O-1663 CBD analog but not CBD up-regulates p8 and autophagy. A primary mechanism for the antitumor activity of the mixed CB$_1$ and CB$_2$ receptor agonist (THC) and CB$_2$ selective agonists is the up-regulation of p8 and the autophagy pathway. The O-1663 CBD analog was able to up-regulate p8 and the marker of autophagy LC3 (FIG. 26, panels C and D). The O-1663 CBD analog was also significantly more potent that THC at up-regulating p8 and L3. In comparison to THC and the O-1663 CBD analog the IC$_{50}$ of CBD for inhibiting cell viability, that is sufficient to stimulate ROS and down-regulate Id-1 expression, did not produce up-regulation of p8 and LC3.

In comparison to CBD, the O-1663 CBD analog is more active at targeting breast cancer metastasis. Since O-1663 CBD analog was significantly more effective than CBD at targeting Id-1 and also targets CB$_2$ receptor antitumor activity, it was predicted that the compound would be more active in inhibiting metastasis of breast cancer cell lines which are dependent Id-1 expression for disease progression (e.g., 4T1 and MDA-MB231). The activity of CBD to the 0-1663 CBD analog in the 4T1 i.v. model of breast cancer metastasis was then compared (FIG. 27, panels A and B). We found that the 0-1663 CBD analog was a 2.3 fold more potent at inhibiting total metastasis [O-1663: EC$_{50}$=0.13 (0.10-0.20); CBD: EC$_{50}$=0.29 (0.18-0.49)] and 7.0 fold more potent than CBD at inhibiting lung metastatic foci >2 mm [O-1663: $EC_{50}$=0.02 (0.01-0.05); CBD: $EC_{50}$=0.15 (0.10-0.24)]. At the most effective dose of O-1663 CBD analog (1 mg/kg) only one of five animals treated with the O-1663 CBD analog had a single metastatic foci greater that >2 mm. The 0-1663 CBD analog was also more potent than CBD in the human MDA-MB231 breast cancer model of metastasis (FIG. 27, panel C). No overt toxicity was noted with the O-1663 CBD analog in the mouse models of metastasis as assessed by weight, appearance and generally activity.

The anti-metastatic activity of the O-1663 CBD analog but not CBD is partially reversed by a $CB_2$ receptor antagonist. In culture and in vivo, the data supports that the O-1663 CBD analog targets two distinct antitumor tumor pathways. Those targeted by $CB_2$ receptor activation such as p8 and autophagy, and those specific to CBD such as up-regulation of ROS and down-regulation of Id-1. To provide further support for this hypothesis in vivo, mice bearing 4T1 tumors were treated with CBD and the O-1663 CBD analog in the presence of a $CB_2$ receptor antagonist (FIG. 27, panels D and E). In agreement with the in vitro results, the antimetastic activity of CBD was not affected by co-administration with SR14458 whereas the anti-metastatic activity of the O-1663 CBD analog was partially reversed by the antagonist. In addition, a combination treatment with CBD and THC was included. The combination of CBD with THC produced the same level of anti-metastatic activity as the O-1663 CBD analog.

O-1663 CBD analog produces a robust inhibition of more advanced stages of metastasis and increases survival. The activity of CBD and the O-1663 CBD analog to inhibit the formation of lung tumor foci in more advanced stages of metastasis was then compared. Mice were treated at a time point where visual lung metastatic foci were already formed. Mice were injected i.v. with 4T1 cells and kept for one week in order to allow for the formation of visible lung metastatic foci. The mice were then treated with CBD and the O-1663 CBD analog. As demonstrated in FIG. 28, panels A and B, both cannabinoids dose-dependently reduced the growth of established lung metastatic foci and reduced the formation of new metastatic foci. The O-1663 CBD analog was significantly more potent than CBD in reducing percent metastasis. Since the O-1663 CBD analog produced a robust inhibition of total metastasis and was highly active at reducing metastatic foci >2 mm, it was predicted that the O-1663 CBD analog would produce substantial increases in survival even when administered at more advanced stages of breast cancer metastasis. A survival study was then carried out where the activity of CBD to O-1663 CBD analog was compared (FIG. 28, panel C). Seven days after i.v. injection of 4T1 cells, mice were treated daily with vehicle, CBD (0.5 or 1 mg/kg, a dose producing maximum anti-metastatic activity) or O-1663 CBD analog (0.5 or 1 mg/kg). The mice were treated until they demonstrated signs of disease progression that necessitated euthanasia, as previously described. CBD produced a medium increase in survival of 4 days (p<0.02) whereas the O-1663 CBD analog produced a medium increase in survival of 30 days (p<0.006). In the group treated with the O-1663 CBD analog, 50% of the mice were still alive and demonstrated no signs of disease progression at time of euthanasia (2 months). More importantly, under a dissection microscope, visible lung metastatic foci were not present in 20% of the mice.

Quantitative western analysis of Id-1 expression in breast cancer 4T1 cells with CBD or O-1663 CBD analog. To examine whether CBD or O-1663 CBD analog would inhibit Id-1 protein expression in cells proposed for the in-vivo metastic cancer model, quantitative Western analysis was performed with 4T1 cells. 4T1 cells were treated with 1.0 μM of cannabinoid for two days and then analyzed for Id-1 protein expression. It was determined that 4T1 cells treated with the O-1663 CBD analog downregulated Id-1 protein expression to a far greater extent than CBD (FIG. 29, panel A).

In-vivo studies of breast cancer metastases with CBD or O-1663 CBD analog. 4T1 cells were injected into the tail vein of syngeneic BALB/c mice and then were intraperitoneal injected 2 days later with either vehicle, CBD (1 mg/kg), or O-1663 CBD analog (1 mg/kg). Treatment with CBD and CBD 1663 analog resulted in a reduction of the total amount of metastatic foci. As with the in-vitro data, the in-vivo data demonstrates that the O-1663 CBD analog is a more potent inhibitor than CBD for cancer proliferation (FIG. 29, panels B and C).

In-vivo advanced stage metastasis survivability studies in a mouse model with CBD or O-1663 CBD analog. To determine whether cannabinoids could inhibit the formation of lung tumor foci in more advanced stages of metastasis, we treated mice at a time point where visual lung metastatic foci were already formed (FIG. 30, panel A). Mice injected tail vein with 4T1 cell were kept for one week in order to allow for the formation of visual lung metastatic foci measuring up to 1 mm. The mice where then treated with drug for two months. During this time period, mice were removed from the study when they demonstrated signs of disease progression that necessitated euthanasia. As demonstrated in FIG. 30, panel B, the O-1663 CBD analog was significantly more active than CBD at increasing overall survival. In this highly aggressive syngeneic mouse model of breast cancer, the O-1663 CBD analog produced a significant increase in survival (p<0.006, Log-rank (Mantel-Cox) Test). Whereas the average median survival for the control group and CBD was 32 and 38 days, respectively, 50% of the animals treated with the O-1663 CBD analog were still alive at the completion of the study.

The examples set forth above are provided to give those of ordinary skill in the art a complete disclosure and description of how to make and use the embodiments of the apparatus, systems and methods of the disclosure, and are not intended to limit the scope of what the inventors regard as their disclosure. Modifications of the above-described modes for carrying out the disclosure that are obvious to persons of skill in the art are intended to be within the scope of the following claims.

A number of embodiments of the disclosure have been described. Nevertheless, it will be understood that various modifications may be made without departing from the spirit and scope of the disclosure. Accordingly, other embodiments are within the scope of the following claims.

What is claimed is:

1. A compound comprising the structure of:

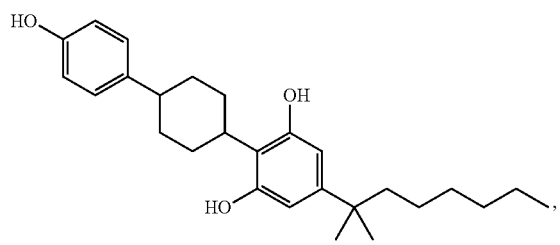 [SMILES: CCCCCCC(C)(C)c1cc(O)c(C2CCC(c3ccc(O)cc3)CC2)c(O)c1]

or a pharmaceutically acceptable salt, or prodrug thereof.

2. A pharmaceutical composition comprising a pharmaceutically acceptable carrier together with a compound of claim 1.

3. The pharmaceutical composition of claim 2, wherein the composition further comprises an additional therapeutic agent.

4. The pharmaceutical composition of claim 3, wherein the additional therapeutic agent is $\Delta^9$-tetrahydrocannabinol ("THC") or a THC derivative.

5. The pharmaceutical composition of claim 4, wherein the THC derivative is selected from the group consisting of $\Delta^9$-tetrahydrocannabinol-$C_4$, $\Delta^9$-tetrahydrocannabivarin, tetrahydrocannabiorcol, $\Delta^9$-tetrahydro-cannabinolic acid A, $\Delta^9$-tetrahydro-cannabinolic acid B, $\Delta^9$-tetrahydro-cannabinolic acid-$C_4$A, $\Delta^9$-tetrahydro-cannabinolic acid-$C_4$B, $\Delta^9$-tetrahydro-cannabivarinic acid A, $\Delta^9$-tetrahydro-cannabiorcolic acid A, $\Delta^9$-tetrahydro-cannabiorcolic acid B, (−)- $\Delta^8$-trans -(6aR,10aR)-$\Delta^8$-tetrahydrocannabinol, (−)- $\Delta^8$-trans-(6aR,10aR) -tetrahydrocannabinolic acid A, and (−)-(6aS,10aR)- $\Delta^9$-tetrahydrocannabinol.

6. The pharmaceutical composition of claim 3, wherein the additional therapeutic agent is selected from the group consisting of alkylating agents, cancer immunotherapy monoclonal antibodies, anti-metabolites, mitotic inhibitors, anti-tumor antibiotics, topoisomerase inhibitors, photosensitizers, tyrosine kinase inhibitors, anti-cancer agents, chemotherapeutic agents, anti-migraine treatments, anti-tussives, mucolytics, decongestants, anti-allergic non-steroidals, expectorants, anti-histamine treatments, anti-retroviral agents, CYP3A inhibitors, CYP3A inducers, protease inhibitors, adrenergic agonists, anti-cholinergics, mast cell stabilizers, xanthines, leukotriene antagonists, glucocorticoid treatments, antibacterial agents, antifungal agents, sepsis treatments, steroidals, local or general anesthetics, NSAIDS, NRIs, DARIs, SNRIs, sedatives, NDRIs, SNDRIs, monoamine oxidase inhibitors, hypothalamic phosphpholipids, anti-emetics, ECE inhibitors, opioids, thromboxane receptor antagonists, potassium channel openers, thrombin inhibitors, growth factor inhibitors, anti-platelet agents, P2Y(AC) antagonists, anti-coagulants, low molecular weight heparins, Factor Vla inhibitors, Factor Xa inhibitors, renin inhibitors, NEP inhibitors, vasopepsidase inhibitors, squalene synthetase inhibitors, anti-atherosclerotic agents, MTP inhibitors, calcium channel blockers, potassium channel activators, alpha-muscarinic agents, beta-muscarinic agents, anti-arrhythmic agents, diuretics, thrombolytic agents, anti-diabetic agents, mineralocorticoid receptor antagonists, growth hormone secretagogues, aP2inhibitors, phophodiesterase inhibitors, anti-inflammatories, anti-proliferatives, antibiotics, farnesyl-protein transferase inhibitors, hormonal agents, plant-derived products, epipodophyllotoxins, taxanes, prenyl-protein transferase inhibitors, anti-TNF antibodies and soluble TNF receptors, and Cyclooxygenase-2inhibitors.

7. The pharmaceutical composition of claim 6, wherein the additional therapeutic agent is selected from the group consisting of alkylating agents, cancer immunotherapy monoclonal antibodies, anti-metabolites, mitotic inhibitors, anti-tumor antibiotics, topisomerase inhibitors, photosensitizers, tyrosine kinase inhibitors, anti-cancer agents, and chemotherapeutic agents.

8. The pharmaceutical composition of claim 7, wherein the additional therapeutic agent is an anti-cancer agent.

9. The pharmaceutical composition of claim 8, wherein the anti-cancer agent is paclitaxel and/or temozolomide.

10. A method for modulating helix-loop-helix Id protein expression, cell proliferation, cell invasion, metastasis or a combination thereof in vivo and/or in vitro by administering a compound of claim 1.

11. A method for treating a disease or disorder in a subject, comprising administering to a subject a therapeutically effective amount of a compound of claim 1, wherein the disease or disorder can be ameliorated by inhibiting the expression of an Id polypeptide, by activating cannabinoid type 2 ("$CB_2$") receptors or a combination thereof.

12. The method of claim 11, wherein the disease or disorder is selected from the group consisting of cancer, chronic pancreatitis, psoriasis, neoplasms, angiomas, endometriosis, obesity, age-related macular degeneration, retinopathies, restenosis, scaring, fibrogenesis, fibrosis, cardiac remodeling, pulmonary fibrosis, scleroderma, failure associated with myocardial infarction, keloids, fibroid tumors, stenting, Alzheimer's Disease, Parkinson's Disease, age related dementia, Huntington's Disease, and amyotrophic lateral sclerosis.

13. The method of claim 12, wherein cancer is selected from the group consisting of leukemia, melanoma, squamous cell carcinoma (SCC), hepatocellular carcinoma, colorectal adenocarcinoma, pancreatic cancer, lung cancer, kidney cancer, medullary thyroid cancer, papillary thyroid cancer, astrocytic tumor, neuroblastoma, Ewing's sarcoma, ovarian tumor, cervical cancer, endometrial carcinoma, breast cancer, prostate cancer, and malignant seminoma.

14. The method of claim 13, wherein the cancer is breast cancer.

15. The method of claim 13, wherein the cancer is brain cancer.

16. The method of claim 15, wherein the brain cancer is glioblastoma multiforme.

17. A method of treating a disease or disorder in a subject, comprising administering to a subject a therapeutically effective amount of a compound having the structure of:

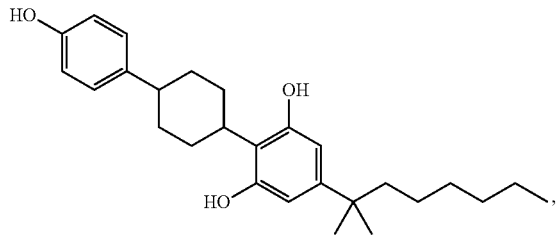 [SMILES: CCCCCCC(C)(C)c1cc(O)c(C2CCC(c3ccc(O)cc3)CC2)c(O)c1]

or a pharmaceutically acceptable salt, or prodrug thereof, wherein the disease or disorder can be ameliorated by inhibiting the expression of an Id polypeptide, by activating $CB_2$ receptors or a combination thereof.

18. The method of claim 17, wherein the disease or disorder is selected from the group consisting of leukemia, melanoma, SCC, hepatocellular carcinoma, colorectal adenocarcinoma, pancreatic cancer, lung cancer, kidney cancer, medullary thyroid cancer, papillary thyroid cancer, astrocytic tumor, neuroblastoma, Ewing's sarcoma, ovarian tumor, cervical cancer, endometrial carcinoma, breast cancer, prostate cancer, and malignant seminoma.

19. The method of claim 18, wherein the disease or disorder is breast cancer or brain cancer.

20. The method of claim 19, wherein the brain cancer is glioblastoma multiforme.

21. The method of claim 17, wherein the method further comprises administering to the subject one or more alkylating agents, cancer immunotherapy monoclonal antibodies, anti-metabolites, mitotic inhibitors, anti-tumor antibiotics, topoisomerase inhibitors, photosensitizers, tyrosine kinase inhibitors, anti-cancer agents, chemotherapeutic agents, or a combination thereof.

* * * * *